US006204435B1

(12) United States Patent
Feitelson et al.

(10) Patent No.: US 6,204,435 B1
(45) Date of Patent: Mar. 20, 2001

(54) PESTICIDAL TOXINS AND NUCLEOTIDE SEQUENCES WHICH ENCODE THESE TOXINS

(75) Inventors: Jerald S. Feitelson; H. Ernest Schnepf; Kenneth E. Narva; Brian A. Stockhoff; James Schmeits; David Loewer; Charles Joseph Dullum, all of San Diego; Judy Muller-Cohn, Del Mar; Lisa M. Stamp, San Diego, all of CA (US)

(73) Assignee: Mycogen Corporation, Indianapolis, IN (US)

( * ) Notice: Subject to any disclaimer, the term of this patent is extended or adjusted under 35 U.S.C. 154(b) by 0 days.

(21) Appl. No.: 08/960,780

(22) Filed: Oct. 30, 1997

Related U.S. Application Data

(60) Provisional application No. 60/029,848, filed on Oct. 30, 1996.

(51) Int. Cl.[7] .............................. H01H 5/00; C12N 1/00; C12N 5/10; C12N 15/63
(52) U.S. Cl. ......................... 800/295; 800/298; 800/302; 536/23.71; 435/320.1; 435/418; 435/419; 435/252.3; 435/254.11; 435/69.1
(58) Field of Search ................................ 536/23.71, 23.7; 435/69.1, 320.1, 252.3, 325, 254.11, 410, 252.31, 252.33, 418, 419; 800/205, 295, 298, 302, 13, FOR 102

(56) References Cited

U.S. PATENT DOCUMENTS

| | | | |
|---|---|---|---|
| 4,448,885 | 5/1984 | Schnepf et al. | 435/252.33 |
| 4,467,036 | 8/1984 | Schnepf et al. | 435/320.1 |
| 4,797,276 | 1/1989 | Herrnstadt et al. | 424/84 |
| 4,853,331 | 8/1989 | Herrnstadt et al. | 435/252.3 |
| 4,918,006 | 4/1990 | Ellar et al. | 435/69.1 |
| 4,948,734 | 8/1990 | Edwards et al. | 514/2 |
| 4,990,332 | 2/1991 | Payne et al. | 424/93.461 |
| 5,039,523 | 8/1991 | Payne et al. | 424/93.461 |
| 5,093,120 | 3/1992 | Edwards et al. | 514/2 |
| 5,126,133 | 6/1992 | Payne et al. | 424/93.461 |
| 5,151,363 | 9/1992 | Payne | 435/252.5 |
| 5,164,180 | 11/1992 | Payne et al. | 424/93.461 |
| 5,169,629 | 12/1992 | Payne et al. | 424/93.461 |
| 5,204,237 | 4/1993 | Gaertner et al. | 435/6 |
| 5,236,843 | 8/1993 | Narva et al. | 435/252.3 |
| 5,262,399 | 11/1993 | Hickle et al. | 435/252.3 |
| 5,270,448 | 12/1993 | Payne | 514/2 |
| 5,281,530 | 1/1994 | Sick et al. | 435/252.3 |
| 5,322,932 | 6/1994 | Narva et al. | 530/350 |
| 5,350,577 | 9/1994 | Payne | 424/93.461 |
| 5,426,049 | 6/1995 | Sick et al. | 435/252.3 |
| 5,439,881 | 8/1995 | Narva et al. | 514/2 |
| 5,667,993 | 9/1997 | Feitelson et al. | 435/91.2 |
| 5,670,365 | 9/1997 | Feitelson | 435/252.3 |
| 5,770,696 | 6/1998 | Warren et al. | 530/350 |
| 5,840,868 | 11/1998 | Warren et al. | 536/23.1 |
| 5,849,870 | 12/1998 | Warren et al. | 530/350 |
| 5,866,326 | 2/1999 | Warren et al. | 435/6 |
| 5,872,212 | 2/1999 | Warren et al. | 530/350 |
| 5,877,012 | 3/1999 | Estruch et al. | 435/252.3 |
| 5,888,801 | 3/1999 | Warren et al. | 435/252.5 |
| 5,889,174 | 3/1999 | Warren et al. | 536/23.71 |

FOREIGN PATENT DOCUMENTS

| | | |
|---|---|---|
| 0359472 | 3/1990 | (EP) . |
| 9405771 | 3/1994 | (WO) . |
| 9421795 | 9/1994 | (WO) . |
| 9424264 | 10/1994 | (WO) . |
| 9605314 | 2/1996 | (WO) . |
| 9610083 | 4/1996 | (WO) . |

OTHER PUBLICATIONS

Li, Jade (1992) "Bacterial Toxins" Current Opinion in Structural Biology 2:545–556.
Asano, Shoji, Hidetaka Hori, Yunlong Cui (1994) "A Unique Insecticidal Activity in *Bacillus thuringiensis* Growth Meduim" Appl. Entomol. Zool. 29(1):39–45.
Gaertner, F. H., Leo Kim (1988) "Current Applied Recombinant DNA Projects" TIBTECH 6(4):54–57.
Gaertner, F.H. (1990) "Cellular Delivery Systems for Insecticidal Proteins: Living and Non–Living Microorganisms" in Controlled Delivery of Crop Protection Agnents, R.M. Wilkins, ed., Taylor and Francis, New York and London, pp. 245–255.
Couch, T.L. (1980) "Mosquito Pathogenicity of *Bacillus thuringiensis* var. *israelensis*" in Developments in Industrial Microbiology 22:61–76.
Beegle, C.C. (1978) "Use of Entomogenous Bacteria in Agroccosystems" in *Developments in Industrial Microbiology* 20:97–104.
Krieg, V.A., et al. (1983) "*Bacillus thuringiensis* var. *tenebrionis*, a new pathotype effective against larvaeof Coleoptera" Z. Ang. Ent. 96:500–508. Abstract.
Hofte, H., H.R. Whiteley (1989) "Insecticidal Crystal Proteins of *Bacillus thuringiensis*" Microbiological Reviews 53(2): 242–255.
Feitelson, J.S., Jewel Payne, Leo Kim (1992) *Bacillus thuringiensis*: Insects and Beyond Bio/Technolgy 10:271–275.
Lambert, B., et al. (1966) "A *Bacillus thuringiensis* Insecticidal Crystal Protein with a High Activity against Members of the Family Noctuidae" Applied and Environmental MicroBiology 62(1): 80–86.

(List continued on next page.)

Primary Examiner—Christopher S. F. Low
Assistant Examiner—Gabrielee Bugaisky
(74) Attorney, Agent, or Firm—Saliwanchik, Lloyd & Saliwanchik

(57) ABSTRACT

Disclosed and claimed are novel *Bacillus thuringiensis* isolates, pesticidal toxins, genes, and nucleotide probes and primers for the identification of genes encoding toxins active against pests. The primers are useful in PCR techniques to produce gene fragments which are characteristic of genes encoding these toxins. The subject invention provides entirely new families of toxins from Bacillus isolates.

48 Claims, No Drawings

OTHER PUBLICATIONS

Gleave, A.P., et al. (1992) "Identification of an Insecticidal Crystal Protein from *Bacillus thuringiensis* DSIR517 with Significant Sequence Differences from Previously Described Toxins" Journal of General Microbiology 138:55–62.

Shevelev, A.B., et al. (1993) "Primary Structure of cryX**, the Novel δ–endotoxin–related gene from *Bacillus thuringiensis* spp. *galleriae*" FEBS 336(1): 79–82.

Smulevitch, S.V., et al. (1991) "Nucleotide Sequence of a Novel δ–Endotoxin Gene crylg of *Bacillus thuringiensis* ssp. *galleriae*" FEBS 293(1–2):25–28.

Schnepf, H.E., H.R. Whiteley (1981) "Cloning and Expression of the *Bacillus thuringiensis* Crystal Protein Gene in *Escheria coli*" Proc. Natl. Acad. Sci. USA 78(5): 2893–2897.

Estruch, J.J., et al. (1996) "Vip3A, A Novel *Bacillus thuringiensis* Vegetative Insecticidal Protein with a Wide Spectrum of Activities Against Lepidoptern Insects" Proc. Natl. Acad. Sci. USA 93: 5389–5394.

Carozzi, N.B., et al., (1991) "Prediction of Insectcidial Activity of *Bacillus thuringiensis* Strains by Polymerase Chain Reaction Product Profiles" Applied and Enviromental Microbiology 57(11):3057–3061.

SEQUENCE LISTING (1) GENERAL INFORMATION:

(iii) NUMBER OF SEQUENCES: 134

(2) INFORMATION FOR SEQ ID NO:1:

(i) SEQUENCE CHARACTERISTICS:
       (A) LENGTH: 29 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

GARCCRTGGA AAGCAAATAA TAARAATGC                                          29

(2) INFORMATION FOR SEQ ID NO:2:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

AAARTTATCT CCCCAWGCTT CATCTCCATT TTG                                     33

(2) INFORMATION FOR SEQ ID NO:3:

(i) SEQUENCE CHARACTERISTICS:
       (A) LENGTH: 2375 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
       (C) INDIVIDUAL ISOLATE: 36a (xi) SEQUENCE DESCRIPTION: SEQ ID NO:3:

ATGAACAAGA ATAATACTAA ATTAAGCACA AGAGCCTTAC CAAGTTTTAT TGATTATTTT          60

AATGGCATTT ATGGATTTGC CACTGGTATC AAAGACATTA TGAACATGAT TTTTAAAACG        120

GATACAGGTG GTGATCTAAC CCTAGACGAA ATTTTAAAGA ATCAGCAGTT ACTAAATGAT        180

ATTTCTGGTA AATTGGATGG GGTGAATGGA AGCTTAAATG ATCTTATCGC ACAGGGAAAC        240

TTAAATACAG AATTATCTAA GGAAATATTA AAAATTGCAA ATGAACAAAA TCAAGTTTTA        300

AATGATGTTA ATAACAAACT CGATGCGATA AATACGATGC TTCGGGTATA TCTACCTAAA        360

ATTACCTCTA TGTTGAGTGA TGTAATGAAA CAAAATTATG CGCTAAGTCT GCAAATAGAA        420

TACTTAAGTA AACAATTGCA AGAGATTTCT GATAAGTTGG ATATTATTAA TGTAAATGTA        480

CTTATTAACT CTACACTTAC TGAAATTACA CCTGCGTATC AAAGGATTAA ATATGTGAAC        540

GAAAAATTTG AGGAATTAAC TTTTGCTACA GAAACTAGTT CAAAAGTAAA AAAGGATGGC        600

TCTCCTGCAA ATATTCTTGA TGAGTTAACT GAGTTAACTG AACTAGCGAA AAGTGTAACA        660

AAAAATGATG TGGATGGTTT TGAATTTTAC CTTAATACAT TCCACGATGT AATGGTAGGA        720

AATAATTTAT TCGGGCGTTC AGCTTTAAAA ACTGCATCGG AATTAATTAC TAAAGAAAAT        780

```
GTGAAAACAA GTGGCAGTGA GGTCGGAAAT GTTTATAACT TCTTAATTGT ATTAACAGCT      840

CTGCAAGCAA AAGCTTTTCT TACTTTAACA ACATGCCGAA AATTATTAGG CTTAGCAGAT      900

ATTGATTATA CTTCTATTAT GAATGAACAT TTAAATAAGG AAAAAGAGGA ATTTAGAGTA      960

AACATCCTCC CTACACTTTC TAATACTTTT TCTAATCCTA ATTATGCAAA AGTTAAAGGA     1020

AGTGATGAAG ATGCAAAGAT GATTGTGGAA GCTAAACCAG ACATGCATT GATTGGGTTT      1080

GAAATTAGTA ATGATTCAAT TACAGTATTA AAAGTATATG AGGCTAAGCT AAAACAAAAT    1140

TATCAAGTCG ATAAGGATTC CTTATCGGAA GTTATTTATG GTGATATGGA TAAATTATTG    1200

TGCCCAGATC AATCTGAACA AATCTATTAT ACAAATAACA TAGTATTTCC AAATGAATAT    1260

GTAATTACTA AAATTGATTT CACTAAAAAA ATGAAAACTT TAAGATATGA GGTAACAGCG    1320

AATTTTTATG ATTCTTCTAC AGGAGAAATT GACTTAAATA AGAAAAAGT AGAATCAAGT     1380

GAAGCGGAGT ATAAAACGTT AAGTGCTAAT GATGATGGGG TGTATATGCC GTTAGGTGTC    1440

ATCAGTGAAA CATTTTTGAC TCCGATTAAT GGGTTTGGCC TCCAAGCTGA TGAAAATTCA    1500

AGATTAATTA CTTTAACATG TAAATCATAT TTAAGAGAAC TACTGCTAGC AACAGACTTA    1560

AGCAATAAAG AAACTAAATT GATCGTCCCG CCAAGTGGTT TTATTAGCAA TATTGTAGAG    1620

AACGGGTCCA TAGAAGAGGA CAATTTAGAG CCGTGGAAAG CAAATAATAA GAATGCGTAT    1680

GTAGATCATA CAGGCGGAGT GAATGGAACT AAAGCTTTAT ATGTTCATAA GGACGGAGGA    1740

ATTTCACAAT TTATTGGAGA TAATTTAAAA CCGAAAACTG AGTATGTAAT CCAATATACT    1800

GTTAAAGGAA AACCTTCTAT TCATTTAATA GATGAAAATA CTGGATATAT TCATTATGAA    1860

GATACAAATA ATAATTTAGA AGATTATCAA ACTATTAATA AACGTTTTAC TACAGGAACT    1920

GATTTAAAGG GAGTGTATTT AATTTTAAAA AGTCAAAATG GAGATGAAGC TTGGGGAGAT    1980

AACTTTATTA TTTTGGAAAT TAGTCCTTCT GAAAAGTTAT TAAGTCCAGA ATTAATTAAT    2040

ACAAATAATT GGACGAGTAC GGGATCAACT AATATTAGCG GTAATACACT CACTCTTTAT    2100

CAGGGAGGAC GAGGGATTCT AAAACAAAAC CTTCAATTAG ATAGTTTTTC AACTTATAGA    2160

GTGTATTTTT CTGTGTCCGG AGATGCTAAT GTAAGGATTA GAAATTCTAG GGAAGTGTTA    2220

TTTGAAAAAA GATATATGAG CGGTGCTAAA GATGTTTCTG AAATGTTCAC TACAAAATTT    2280

GAGAAAGATA ACTTTTATAT AGAGCTTTCT CAAGGGAATA ATTTATATGG TGGTCCTATT    2340

GTACATTTTT ACGATGTCTC TATTAAGTAA CCCAA                                2375

(2) INFORMATION FOR SEQ ID NO:4:

(i) SEQUENCE CHARACTERISTICS:
        (A) LENGTH: 790 amino acids
        (B) TYPE: amino acid
        (C) STRANDEDNESS: single
        (D) TOPOLOGY: linear (ii) MOLECULE TYPE: protein (vi) ORIGINAL SOURCE:
        (C) INDIVIDUAL ISOLATE: 36a (xi) SEQUENCE DESCRIPTION: SEQ ID NO:4:

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
                20                  25                  30

Ile Met Asn Met Ile Phe Lys Thr Asp Thr Gly Gly Asp Leu Thr Leu
        35                  40                  45
```

-continued

```
Asp Glu Ile Leu Lys Asn Gln Gln Leu Leu Asn Asp Ile Ser Gly Lys
 50                  55                  60

Leu Asp Gly Val Asn Gly Ser Leu Asn Asp Leu Ile Ala Gln Gly Asn
 65                  70                  75                  80

Leu Asn Thr Glu Leu Ser Lys Glu Ile Leu Lys Ile Ala Asn Glu Gln
                 85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
            115                 120                 125

Met Lys Gln Asn Tyr Ala Leu Ser Leu Gln Ile Glu Tyr Leu Ser Lys
            130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asn Ile Leu Asp Glu
            195                 200                 205

Leu Thr Glu Leu Thr Glu Leu Ala Lys Ser Val Thr Lys Asn Asp Val
            210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
            275                 280                 285

Leu Thr Thr Cys Arg Lys Leu Leu Gly Leu Ala Asp Ile Asp Tyr Thr
            290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
            355                 360                 365

Val Leu Lys Val Tyr Glu Ala Lys Leu Lys Gln Asn Tyr Gln Val Asp
            370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
            435                 440                 445

Glu Ile Asp Leu Asn Lys Lys Lys Val Glu Ser Ser Glu Ala Glu Tyr
450                 455                 460

Lys Thr Leu Ser Ala Asn Asp Asp Gly Val Tyr Met Pro Leu Gly Val
```

```
465                 470                 475                 480
Ile Ser Glu Thr Phe Leu Thr Pro Ile Asn Gly Phe Gly Leu Gln Ala
                485                 490                 495
Asp Glu Asn Ser Arg Leu Ile Thr Leu Thr Cys Lys Ser Tyr Leu Arg
                500                 505                 510
Glu Leu Leu Leu Ala Thr Asp Leu Ser Asn Lys Glu Thr Lys Leu Ile
                515                 520                 525
Val Pro Pro Ser Gly Phe Ile Ser Asn Ile Val Glu Asn Gly Ser Ile
            530                 535                 540
Glu Glu Asp Asn Leu Glu Pro Trp Lys Ala Asn Asn Lys Asn Ala Tyr
545                 550                 555                 560
Val Asp His Thr Gly Gly Val Asn Gly Thr Lys Ala Leu Tyr Val His
                565                 570                 575
Lys Asp Gly Gly Ile Ser Gln Phe Ile Gly Asp Asn Leu Lys Pro Lys
                580                 585                 590
Thr Glu Tyr Val Ile Gln Tyr Thr Val Lys Gly Lys Pro Ser Ile His
                595                 600                 605
Leu Ile Asp Glu Asn Thr Gly Tyr Ile His Tyr Glu Asp Thr Asn Asn
            610                 615                 620
Asn Leu Glu Asp Tyr Gln Thr Ile Asn Lys Arg Phe Thr Thr Gly Thr
625                 630                 635                 640
Asp Leu Lys Gly Val Tyr Leu Ile Leu Lys Ser Gln Asn Gly Asp Glu
                645                 650                 655
Ala Trp Gly Asp Asn Phe Ile Ile Leu Glu Ile Ser Pro Ser Glu Lys
                660                 665                 670
Leu Leu Ser Pro Glu Leu Ile Asn Thr Asn Asn Trp Thr Ser Thr Gly
                675                 680                 685
Ser Thr Asn Ile Ser Gly Asn Thr Leu Thr Leu Tyr Gln Gly Gly Arg
            690                 695                 700
Gly Ile Leu Lys Gln Asn Leu Gln Leu Asp Ser Phe Ser Thr Tyr Arg
705                 710                 715                 720
Val Tyr Phe Ser Val Ser Gly Asp Ala Asn Val Arg Ile Arg Asn Ser
                725                 730                 735
Arg Glu Val Leu Phe Glu Lys Arg Tyr Met Ser Gly Ala Lys Asp Val
                740                 745                 750
Ser Glu Met Phe Thr Thr Lys Phe Glu Lys Asp Asn Phe Tyr Ile Glu
                755                 760                 765
Leu Ser Gln Gly Asn Asn Leu Tyr Gly Gly Pro Ile Val His Phe Tyr
            770                 775                 780
Asp Val Ser Ile Lys Pro
785                 790

(2) INFORMATION FOR SEQ ID NO:5:

(i) SEQUENCE CHARACTERISTICS:
        (A) LENGTH: 2370 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 81Fd (xi) SEQUENCE DESCRIPTION: SEQ ID NO:5:

ATGAACAAGA ATAATACTAA ATTAAGCACA AGAGCCTTAC CAAGTTTTAT TGATTATTTT     60
```

-continued

```
AATGGCATTT ATGGATTTGC CACTGGTATC AAAGACATTA TGAACATGAT TTTTAAAACG      120
GATACAGGTG GTGATCTAAC CCTAGACGAA ATTTTAAAGA ATCAGCAGTT ACTAAATGAT      180
ATTTCTGGTA AATTGGATGG GGTGAATGGA AGCTTAAATG ATCTTATCGC ACAGGGAAAC      240
TTAAATACAG AATTATCTAA AGAAATATTA AAAATTGCAA ATGAACAAAA TCAAGTTTTA      300
AATGATGTTG ATAACAAACT CGATGCGATA AATACGATGC TTCGGGTATA TCTACCTAAA      360
ATTACCTCTA TGTTGAGTGA TGTAATGAAA CAAAATTATG CGCTAAGTCT GCAAATAGAA      420
TACTTAAGTA AACAATTGCA AGAGATTTCT GATAAGTTGG ATATTATTAA TGTAAATGTA      480
CTTATTAACT CTACACTTAC TGAAATTACA CCTGCGTATC AAAGGATTAA ATATGTGAAC      540
GAAAAATTTG AGGAATTAAC TTTTGCTACA GAAACTAGTT CAAAAGTAAA AAAGGATGGC      600
TCTCCTGCAG ATATTCTTGA TGAGTTAACT GAGTTAACTG AACTAGCGAA AAGTGTAACA      660
AAAAATGATG TGGATGGTTT TGAATTTTAC CTTAATACAT TCCACGATGT AATGGTAGGA      720
AATAATTTAT TCGGGCGTTC AGCTTTAAAA ACTGCATCGG AATTAATTAC TAAAGAAAAT      780
GTGAAAACAA GTGGCAGTGA GGTCGGAAAT GTTTATAACT TCTTAATTGT ATTAACAGCT      840
CTGCAAGCAA AAGCTTTTCT TACTTTAACA ACATGCCGAA AATTATTAGG CTTAGCAGAT      900
ATTGATTATA CTTCTATTAT GAATGAACAT TTAAATAAGG AAAAAGAGGA ATTTAGAGTA      960
AACATCCTCC CTACACTTTC TAATACTTTT TCTAATCCTA ATTATGCAAA AGTTAAAGGA     1020
AGTGATGAAG ATGCAAAGAT GATTGTGGAA GCTAAACCAG GACATGCATT GGTTGGGTTT     1080
GAAATTAGTA ATGATTCAAT TACAGTATTA AAAGTATATG AGGCTAAGCT AAAACAAAAT     1140
TATCAAGTTG ATAAGGATTC CTTATCGGAA GTTATTTATG GTGATATGGA TAAATTATTG     1200
TGCCCAGATC AATCTGAACA AATCTATTAT ACAAATAACA TAGTATTTCC AAATGAATAT     1260
GTAATTACTA AAATTGATTT TACTAAAAAA ATGAAAACTT TAAGATATGA GGTAACAGCG     1320
AATTTTTATG ATTCTTCTAC AGGAGAAATT GACTTAAATA AGAAAAAGT AGAATCAAGT      1380
GAAGCGGAGT ATAGAACGTT AAGTGCTAAT GATGATGGAG TGTATATGCC GTTAGGTGTC     1440
ATCAGTGAAA CATTTTTGAC TCCGATTAAT GGGTTTGGCC TCCAAGCTGA TGAAAATTCA     1500
AGATTAATTA CTTTAACATG TAAATCATAT TTAAGAGAAC TACTGCTAGC AACAGACTTA     1560
AGCAATAAAG AAACTAAATT GATCGTCCCG CCCAGTGGTT TTATTAAAAA TATTGTAGAG     1620
AACGGGTCCA TAGAAGAGGA CAATTTAGAG CCGTGGAAAG CAAATAATAA GAATGAGTAT     1680
GTAGATCATA CAGGCGGAGT GAATGGGRACT AAAGCTTTAT ATGTTCATAA GGACGGAGGA    1740
ATTTCACAAT TTATTGGAGA TAAGTTAAAA CCGAAAACTG AGTATGTAAT CCAATATACT     1800
GTTAAAGGAA AACCTTCTAT TCATTTAAAA GATGAAAATA CTGGATATAT TCATTATGAA     1860
GATACAAATA ATAATTTAGA AGATTATCAA ACTATTACTA AACGTTTTAC TACAGGAACT     1920
GATTTAAAGG GAGTGTATTT AATTTTAAAA AGTCAAAATG GAGATGAAGC TTGGGGAGAT     1980
AACTTTATTA TTTTGGAAAT TAGTCCTTCT GAAAAGTTAT TAAGTCCAGA ATTAATTAAT     2040
ACAAATAATT GGACGAGTAC GGGATCAACT AATATTAGCG GTAATACACT CACTCTTTAT     2100
CAGGGAGGAC GAGGAATTCT AAAACAAAAC CTTCAATTAG ATAGTTTTTC AACTTATAGA     2160
GTGTATTTTT CTGTGTCCGG AGATGCTAAT GTAAGGATTA GAAATTCTAG GGAAGTGTTA     2220
TTTGAAAAAA GATATATGAG CGGTGCTAAA GATGTTTCTG AAATTTTCAC TACAAAATTT     2280
GGGAAAGATA ACTTTTATAT AGAGCTTTCT CAAGGGAATA ATTTAAATGG TGGCCCTATT     2340
GTACAGTTTC CCGATGTCTC TATTAAGTAA                                     2370
```

(2) INFORMATION FOR SEQ ID NO:6:

(i) SEQUENCE CHARACTERISTICS:
        (A) LENGTH: 789 amino acids
        (B) TYPE: amino acid
        (C) STRANDEDNESS: single
        (D) TOPOLOGY: linear (ii) MOLECULE TYPE: protein (vi) ORIGINAL SOURCE:
        (C) INDIVIDUAL ISOLATE: 81Fd (xi) SEQUENCE DESCRIPTION: SEQ ID NO:6:

```
Met Asn Lys Asn Asn Thr Lys Leu Ser Thr Arg Ala Leu Pro Ser Phe
  1               5                  10                  15

Ile Asp Tyr Phe Asn Gly Ile Tyr Gly Phe Ala Thr Gly Ile Lys Asp
             20                  25                  30

Ile Met Asn Met Ile Phe Lys Thr Asp Thr Gly Gly Asp Leu Thr Leu
         35                  40                  45

Asp Glu Ile Leu Lys Asn Gln Gln Leu Leu Asn Asp Ile Ser Gly Lys
 50                  55                  60

Leu Asp Gly Val Asn Gly Ser Leu Asn Asp Leu Ile Ala Gln Gly Asn
 65                  70                  75                  80

Leu Asn Thr Glu Leu Ser Lys Glu Ile Leu Lys Ile Ala Asn Glu Gln
                 85                  90                  95

Asn Gln Val Leu Asn Asp Val Asp Asn Lys Leu Asp Ala Ile Asn Thr
                100                 105                 110

Met Leu Arg Val Tyr Leu Pro Lys Ile Thr Ser Met Leu Ser Asp Val
            115                 120                 125

Met Lys Gln Asn Tyr Ala Leu Ser Leu Gln Ile Glu Tyr Leu Ser Lys
130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
            195                 200                 205

Leu Thr Glu Leu Thr Glu Leu Ala Lys Ser Val Thr Lys Asn Asp Val
        210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
            275                 280                 285

Leu Thr Thr Cys Arg Lys Leu Leu Gly Leu Ala Asp Ile Asp Tyr Thr
        290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335
```

```
Lys Val Lys Gly Ser Asp Glu Asp Ala Lys Met Ile Val Glu Ala Lys
            340                 345                 350

Pro Gly His Ala Leu Val Gly Phe Glu Ile Ser Asn Asp Ser Ile Thr
            355                 360                 365

Val Leu Lys Val Tyr Glu Ala Lys Leu Lys Gln Asn Tyr Gln Val Asp
            370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
                420                 425                 430

Thr Leu Arg Tyr Glu Val Thr Ala Asn Phe Tyr Asp Ser Ser Thr Gly
            435                 440                 445

Glu Ile Asp Leu Asn Lys Lys Lys Val Glu Ser Ser Glu Ala Glu Tyr
            450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
                500                 505                 510

Glu Leu Leu Leu Ala Thr Asp Leu Ser Asn Lys Glu Thr Lys Leu Ile
            515                 520                 525

Val Pro Pro Ser Gly Phe Ile Lys Asn Ile Val Glu Asn Gly Ser Ile
            530                 535                 540

Glu Glu Asp Asn Leu Glu Pro Trp Lys Ala Asn Asn Lys Asn Glu Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
                580                 585                 590

Thr Glu Tyr Val Ile Gln Tyr Thr Val Lys Gly Lys Pro Ser Ile His
            595                 600                 605

Leu Lys Asp Glu Asn Thr Gly Tyr Ile His Tyr Glu Asp Thr Asn Asn
            610                 615                 620

Asn Leu Glu Asp Tyr Gln Thr Ile Thr Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
                660                 665                 670

Leu Leu Ser Pro Glu Leu Ile Asn Thr Asn Asn Trp Thr Ser Thr Gly
            675                 680                 685

Ser Thr Asn Ile Ser Gly Asn Thr Leu Thr Leu Tyr Gln Gly Gly Arg
            690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Ile Phe Thr Thr Lys Phe Gly Lys Asp Asn Phe Tyr Ile Glu
```

755        760        765
Leu Ser Gln Gly Asn Asn Leu Asn Gly Gly Pro Ile Val Gln Phe Pro
770            775            780

Asp Val Ser Ile Lys
785

(2) INFORMATION FOR SEQ ID NO:7:

(i) SEQUENCE CHARACTERISTICS:
        (A) LENGTH: 2375 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: Jav90

(xi) SEQUENCE DESCRIPTION: SEQ ID NO:7:

```
ATGAACAAGA ATAATACTAA ATTAAGCACA AGAGCCTTAC CAAGTTTTAT TGATTATTTT      60
AATGGCATTT ATGGATTTGC CACTGGTATC AAAGACATTA TGAACATGAT TTTTAAAACG     120
GATACAGGTG GTGATCTAAC CCTAGACGAA ATTTTAAAGA ATCAGCAGTT ACTAAATGAT     180
ATTTCTGGTA AATTGGATGG GGTGAATGGA AGCTTAAATG ATCTTATCGC ACAGGGAAAC     240
TTAAATACAG AATTATCTAA GGAAATATTA AAAATTGCAA ATGAACAAAA TCAAGTTTTA     300
AATGATGTTA ATAACAAACT CGATGCGATA AATACGATGC TTCGGGTATA TCTACCTAAA     360
ATTACCTCTA TGTTGAGTGA TGTAATGAAA CAAAATTATG CGCTAAGTCT GCAAATAGAA     420
TACTTAAGTA AACAATTGCA AGAGATTTCT GATAAGTTGG ATATTATTAA TGTAAATGTA     480
CTTATTAACT CTACACTTAC TGAAATTACA CCTGCGTATC AAAGGATTAA ATATGTGAAC     540
GAAAAATTTG AGGAATTAAC TTTTGCTACA GAAACTAGTT CAAAAGTAAA AAAGGATGGC     600
TCTCCTGCAG ATATTCTTGA TGAGTTAACT GAGTTAACTG AACTAGCGAA AAGTGTAACA     660
AAAAATGATG TGGATGGTTT TGAATTTTAC CTTAATACAT TCCACGATGT AATGGTAGGA     720
AATAATTTAT TCGGGCGTTC AGCTTTAAAA ACTGCATCGG AATTAATTAC TAAAGAAAAT     780
GTGAAAACAA GTGGCAGTGA GGTCGGAAAT GTTTATAACT TCTTAATTGT ATTAACAGCT     840
CTGCAAGCAA AAGCTTTTCT TACTTTAACA ACATGCCGAA AATTATTAGG CTTAGCAGAT     900
ATTGATTATA CTTCTATTAT GAATGAACAT TTAAATAAGG AAAAAGAGGA ATTTAGAGTA     960
AACATCCTCC CTACACTTTC TAATACTTTT TCTAATCCTA ATTATGCAAA AGTTAAAGGA    1020
AGTGATGAAG ATGCAAAGAT GATTGTGGAA GCTAAACCAG GACATGCATT GATTGGGTTT    1080
GAAATTAGTA ATGATTCAAT TACAGTATTA AAAGTATATG AGGCTAAGCT AAAACAAAAT    1140
TATCAAGTCG ATAAGGATTC CTTATCGGAA GTTATTTATG GTGATATGGA TAAATTATTG    1200
TGCCCAGATC AATCTGAACA AATCTATTAT ACAAATAACA TAGTATTTCC AAATGAATAT    1260
GTAATTACTA AAATTGATTT CACTAAAAAA ATGAAAACTT TAAGATATGA GGTAACAGCG    1320
AATTTTTATG ATTCTTCTAC AGGAGAAATT GACTTAAATA GAAAAAAGT AGAATCAAGT    1380
GAAGCGGAGT ATAGAACGTT AAGTGCTAAT GATGATGGGG TGTATATGCC GTTAGGTGTC    1440
ATCAGTGAAA CATTTTTGAC TCCGATTAAT GGGTTTGGCC TCCAAGCTGA TGAAAATTCA    1500
AGATTAATTA CTTTAACATG TAAATCATAT TTAAGAGAAC TACTGCTAGC AACAGACTTA    1560
AGCAATAAAG AAACTAAATT GATYGTCCCG CCAAGTGGTT TTATTAGCAA TATTGTAGAG    1620
AACGGGTCCA TAGAAGAGGA CAATTTAGAG CCGTGGAAAG CAAATAATAA GAATGCGTAT    1680
```

-continued

```
GTAGATCATA CAGGCGGAGT GAATGGAACT AAAGCTTTAT ATGTTCATAA GGACGGAGGA    1740

ATTTCACAAT TTATTGGAGA TAAGTTAAAA CCGAAAACTG AGTATGTAAT CCAATATACT    1800

GTTAAAGGAA AACCTTCTAT TCATTTAAAA GATGAAAATA CTGGATATAT TCATTATGAA    1860

GATACAAATA ATAATTTAGA AGATTATCAA ACTATTAATA AACGTTTTAC TACAGGAACT    1920

GATTTAAAGG GAGTGTATTT AATTTTAAAA AGTCAAAATG GAGATGAAGC TTGGGGAGAT    1980

AACTTTATTA TTTTGGAAAT TAGTCCTTCT GAAAAGTTAT TAAGTCCAGA ATTAATTAAT    2040

ACAAATAATT GGACGAGTAC GGGATCAACT AATATTAGCG GTAATACACT CACTCTTTAT    2100

CAGGGAGGAC GAGGGATTCT AAAACAAAAC CTTCAATTAG ATAGTTTTTC AACTTATAGA    2160

GTGTATTTTT CTGTGTCCGG AGATGCTAAT GTAAGGATTA GAAATTCTAG GGAAGTGTTA    2220

TTTGAAAAAA GATATATGAG CGGTGCTAAA GATGTTTCTG AAATGTTCAC TACAAAATTT    2280

GAGAAAGATA ACTTTTATAT AGAGCTTTCT CAAGGGAATA ATTTATATGG TGGTCCTATT    2340

GTACATTTTT ACGATGTCTC TATTAAGTAA CCCAA                               2375
```

(2) INFORMATION FOR SEQ ID NO:8:

(i) SEQUENCE CHARACTERISTICS:
        (A) LENGTH: 790 amino acids
        (B) TYPE: amino acid
        (C) STRANDEDNESS: single
        (D) TOPOLOGY: linear (ii) MOLECULE TYPE: protein (vi) ORIGINAL SOURCE:
        (C) INDIVIDUAL ISOLATE: Jav90

(xi) SEQUENCE DESCRIPTION: SEQ ID NO:8:

```
Met Asn Lys Asn Asn Thr Lys Leu Ser Thr Arg Ala Leu Pro Ser Phe
 1               5                  10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205
```

-continued

```
Leu Thr Glu Leu Thr Glu Leu Ala Lys Ser Val Thr Lys Asn Asp Val
210                 215                 220
Asp Gly Phe Glu Phe Tyr Leu Asn Thr Phe His Asp Val Met Val Gly
225                 230                 235                 240
Asn Asn Leu Phe Gly Arg Ser Ala Leu Lys Thr Ala Ser Glu Leu Ile
            245                 250                 255
Thr Lys Glu Asn Val Lys Thr Ser Ser Glu Val Gly Asn Val Tyr
                260                 265                 270
Asn Phe Leu Ile Val Leu Thr Ala Leu Gln Ala Lys Ala Phe Leu Thr
            275                 280                 285
Leu Thr Thr Cys Arg Lys Leu Leu Gly Leu Ala Asp Ile Asp Tyr Thr
290                 295                 300
Ser Ile Met Asn Glu His Leu Asn Lys Glu Lys Glu Phe Arg Val
305                 310                 315                 320
Asn Ile Leu Pro Thr Leu Ser Asn Thr Phe Ser Asn Pro Asn Tyr Ala
                325                 330                 335
Lys Val Lys Gly Ser Asp Glu Asp Ala Lys Met Ile Val Glu Ala Lys
            340                 345                 350
Pro Gly His Ala Leu Ile Gly Phe Glu Ile Ser Asn Asp Ser Ile Thr
                355                 360                 365
Val Leu Lys Val Tyr Glu Ala Lys Leu Lys Gln Asn Tyr Gln Val Asp
370                 375                 380
Lys Asp Ser Leu Ser Glu Val Ile Tyr Gly Asp Met Asp Lys Leu Leu
385                 390                 395                 400
Cys Pro Asp Gln Ser Glu Gln Ile Tyr Tyr Thr Asn Asn Ile Val Phe
                405                 410                 415
Pro Asn Glu Tyr Val Ile Thr Lys Ile Asp Phe Thr Lys Lys Met Lys
            420                 425                 430
Thr Leu Arg Tyr Glu Val Thr Ala Asn Phe Tyr Asp Ser Ser Thr Gly
            435                 440                 445
Glu Ile Asp Leu Asn Lys Lys Val Glu Ser Ser Glu Ala Glu Tyr
450                 455                 460
Arg Thr Leu Ser Ala Asn Asp Asp Gly Val Tyr Met Pro Leu Gly Val
465                 470                 475                 480
Ile Ser Glu Thr Phe Leu Thr Pro Ile Asn Gly Phe Gly Leu Gln Ala
                485                 490                 495
Asp Glu Asn Ser Arg Leu Ile Thr Leu Thr Cys Lys Ser Tyr Leu Arg
            500                 505                 510
Glu Leu Leu Leu Ala Thr Asp Leu Ser Asn Lys Glu Thr Lys Leu Ile
            515                 520                 525
Val Pro Pro Ser Gly Phe Ile Ser Asn Ile Val Glu Asn Gly Ser Ile
530                 535                 540
Glu Glu Asp Asn Leu Glu Pro Trp Lys Ala Asn Asn Lys Asn Ala Tyr
545                 550                 555                 560
Val Asp His Thr Gly Gly Val Asn Gly Thr Lys Ala Leu Tyr Val His
                565                 570                 575
Lys Asp Gly Gly Ile Ser Gln Phe Ile Gly Asp Lys Leu Lys Pro Lys
            580                 585                 590
Thr Glu Tyr Val Ile Gln Tyr Thr Val Lys Gly Lys Pro Ser Ile His
            595                 600                 605
Leu Lys Asp Glu Asn Thr Gly Tyr Ile His Tyr Glu Asp Thr Asn Asn
610                 615                 620
```

```
Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
                660                 665                 670

Leu Leu Ser Pro Glu Leu Ile Asn Thr Asn Asn Trp Thr Ser Thr Gly
                675                 680                 685

Ser Thr Asn Ile Ser Gly Asn Thr Leu Thr Leu Tyr Gln Gly Gly Arg
                690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
                740                 745                 750

Ser Glu Met Phe Thr Thr Lys Phe Glu Lys Asp Asn Phe Tyr Ile Glu
                755                 760                 765

Leu Ser Gln Gly Asn Asn Leu Tyr Gly Gly Pro Ile Val His Phe Tyr
770                 775                 780

Asp Val Ser Ile Lys Pro
785                 790

(2) INFORMATION FOR SEQ ID NO:9:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GCTCTAGAAG GAGGTAACTT ATGAACAAGA ATAATACTAA ATTAAGC                47

(2) INFORMATION FOR SEQ ID NO:10:

(i) SEQUENCE CHARACTERISTICS:
        (A) LENGTH: 2035 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 158C2-ptl (xi) SEQUENCE DESCRIPTION: SEQ ID NO:10:

ATGAACAAGA ATAATACTAA ATTAAGCGCA AGGGCCTACC GAGTTTTATT GATTATTTTA      60

ATGGCATTTA TGGATTTGCC ACTGGTATCA AAGACATTAT GAATATGATT TTTAAAACGG     120

ATACAGGTGG TAATCTAACC TTAGACGAAA TCCTAAAGAA TCAGCAGTTA CTAAATGAGA     180

TTTCTGGTAA ATTGGATGGG GTAAATGGGA GCTTAAATGA TCTTATCGCA CAGGGAAACT     240

TAAATACAGA ATTAGCTAAG CAAATCTTAA AAGTTGCAAA TGAACAAAAT CAAGTTTTAA     300

ATGATGTTAA TAACAAACTA GACTGCGATA ATACGATGC TTAAAATATA TCTACCTAAA     360

ATTCACATCT ATGTTAAGTG ATGTACTGAA GCCAAAATTA TGTGCTTAAG TCTTGCAAAT     420

TGGAATTACC TTTAAGTAAC ATCTGCACCT TGGCAAGAAA TCTCCGACAA GCTAGATATT     480
```

```
ATTAACGTAA ATGTGCTTAT TAACTCTACG CTTACTGAAA TTACACCTGC GTATCAACGA      540

ATTAAATATG TGAATGAAAA ATTTGACGAT TTAACTTTTG CTACAGAAAA CACTTTAAAA      600

GTAAAAAAGG ATAGCTCTCC TGCTGATATT CTTGACGAGT TAACTGAATT AACTGAACTA      660

GCGAAAAGTG TTACAAAAAA TGACGTGGAT GGTTTTGAAT TTTACCTTAA TACATTCCAT      720

GATGTAATGG TGGGAAATAA TTTATTCGGT CGTTCAGCTT TAAAAACTGC TTCGGAATTA      780

ATTGCTAAAG AAAATGTGAA AACAAGTGGC AGTGAAGTAG GAAATGTTTA TAATTTCTTA      840

ATTGTATTAA CAGCTCTACA AGCAAAAGCT TTTCTTACTT TAACAACATG CCGAAAATTA      900

TTAGGCTTAG CAGATATTGA TTATACTTCT ATCATGAATG AGCATTTAAA TAAGGAAAAA      960

GAGGAATTTA GAGTAAACAT CCTTCCCACA CTTTCTAATA CCTTTTCTAA TCCTAATTAT     1020

GCAAAAGCTA AGGGAAGTAA TGAAGATACA AAGATGATTG TGGAAGCTAA ACCAGGATAT     1080

GTTTTGGTTG GATTTGAAAT GAGCAATAAT TCAATTACAG TATTAAAAGC ATATCAAGCT     1140

AAGCTAAAAA AAGATTATCA AATTGATAAG GATTCGTTAT CAGAAATAAT ATATAGTACG     1200

TGATACGGAT AAATTATTAT GTCCGGATCA ATCTGAACAA TATATTATAC AAAGAACATA     1260

GCATTTCCAA ATGAATATGT TATTACTAAA ATTGCTTTTA CTAAAAAAAT GAACAGTTTA     1320

AGGTATGAGG CGACAGCGAA TTTTTATGAT TCTTCTACAG GGGATATTGA TCTAAATAAG     1380

ACAAAAGTAG AATCAAGTGA AGCGGAGTAT AGTATGCTAA AAGCTAGTGA TGATGAAGTT     1440

TACATGCCGC TAGGTCTTAT CAGTGAAACA TTTTTAAATC CAATTAATGG ATTTAGGCTT     1500

GCAGTCGATG AAAATTCCAG ACTAGTAACT TTAACATGTA GATCATATTT AAGAGAGACA     1560

TTGTTAGCGA CAGATTTAAA TAATAAAGAA ACTAAATTGA TTGTCCCACC TAATGTTTTT     1620

ATTAGCAATA TTGTAGAGAA TGGAAATATA GAAATGGACA CCTTAGAACC ATGGAAGGCA     1680

AATAATGAGA ATGCGAATGT AGATTATTCA GGCGGAGTGA ATGGAACTAG AGCTTTATAT     1740

GTTCATAAGG ATGGTGAATT CTCACATTTT ATTGGAGACA AGTTGAAATC TAAAACAGAA     1800

TACTTGATTC GATATATTGT AAAAGGAAAA GCTTCTATTT TTTTAAAAGA TGAAAGAAAT     1860

GAAAATTACA TTTACGAGGA TACAAATAAT AATTTAGAAG ATTATCAAAC TATTACTAAA     1920

CGTTTTACTA CAGGAACTGA TTCGACAGGA TTTTATTTAT TTTTTACTAC TCAAGATGGA     1980

AATGAAGCTT GGGGAGACAC TTTTTTTCTC TAGAAAGAGG TAACTTATGA ACAAG         2035
```

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
CATCCTCCCT ACACTTTCTA A                                                 21
```

(2) INFORMATION FOR SEQ ID NO:12:

(i) SEQUENCE CHARACTERISTICS:
        (A) LENGTH: 950 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
             (C) INDIVIDUAL ISOLATE: 49C3-pt1

(xi) SEQUENCE DESCRIPTION: SEQ ID NO:12:

AAACTAGAGG GAGTGATAAG GATGCGAAAA TCATTATGGA AGCTAAACCT GGATATGCTT      60

TAGTTGGATT TGAAATAAGT AAGGATTCAA TTGCAGTATT AAAAGTTTAT CAGGCAAAGC     120

TAAAACACAA CTATCAAATT GATAAGGATT CGTTATCAGA AATTGTTTAT GGTGATATAG     180

ATAAATTATT ATGTCCGGAT CAATCTGAAC AAATGTATTA TACAAATAAA ATAGCATTTC     240

CAAATGAATA TGTTATCACT AAAATTGCTT TTACTAAAAA ACTGAACAGT TTAAGATATG     300

AGGTCACAGC GAATTTTTAT GACTCTTCTA CAGGAGATAT TGATCTAAAT AAGAAAAAAA     360

TAGAATCAAG TGAAGCGGAG TTTAGTATGC TAAATGCTAA TAATGATGGT GTTTATATGC     420

CGATAGGTAC TATAAGTGAA ACATTTTTGA CTCCAATTAA TGGATTTGGC CTCGTAGTCG     480

ATGAAAATTC AAGACTAGTA ACTTTGACAT GTAAATCATA TTTAAGAGAG ACATTGTTAG     540

CAACAGACTT AAGTAATAAA GAAACTAAAC TGATTGTCCC ACCTAATGGT TTTATTAGCA     600

ATATTGTAGA AAATGGGAAC TTAGAGGGAG AAAACTTAGA GCCGTGGGAA AGCAAATAAC     660

AAAAATGCGT ATGTAGATCA TACCGGAGGT GTAAATGGAA CTAAAGTTTT ATATGTTCAT     720

GAGGATGGTG AGTTCTCACA ATTTATTGGG GATAAATTGA AATTGAAAAC AGAATATGTA     780

ATTCCATATA TTGTAAAGGG GAAAGCTGCT ATTTATTTAA AAGATGAAAA AAATGGGGAT     840

TACATATCAT GAAGAAACAT CATAATGCAA TTGAAGATTT TTCCAGCTGT AACTTCAATA     900

ATGATTTTCG CATCCTTATC ATCCCTCTAG CTTTTTCATA ATAGGATAGA                950

(2) INFORMATION FOR SEQ ID NO:13:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:13:

AAATTATGCG CTAAGTCTGC                                                  20

(2) INFORMATION FOR SEQ ID NO:14:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:14:

TTGATCCGGA CATAATAAT                                                   19

(2) INFORMATION FOR SEQ ID NO:15:

(i) SEQUENCE CHARACTERISTICS:
         (A) LENGTH: 176 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:

(C) INDIVIDUAL ISOLATE: 49C8-pt1

(xi) SEQUENCE DESCRIPTION: SEQ ID NO:15:

| | | | | | |
|---|---|---|---|---|---|
| GTAAATTATG | CGCTAAGTCT | GCACCTTTTT | TCACTGTTAC | TAAACATCAC | TTTTCCTATA | 60
| TCCCCTTAGC | TCTTATGGAT | TATTGAGCAA | ACTTATCTTG | TTAATTACTA | CTCCCCATCA | 120
| TATGCTAAAC | AAAAACCAAA | CAAACATTAT | CTATTATATG | TCCGGATCAA | AATGTA | 176

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GGRTTAMTTG GRTAYTATTT                                                  20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

ATATCKWAYA TTKGCATTTA                                                  20

(2) INFORMATION FOR SEQ ID NO:18:

(i) SEQUENCE CHARACTERISTICS:
        (A) LENGTH: 1076 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 10E1

(xi) SEQUENCE DESCRIPTION: SEQ ID NO:18:

| | | | | | |
|---|---|---|---|---|---|
| TGGGATTACT | TGGATATTAT | TTCCAGGATC | AAAAGTTTCA | GCAACTTGCT | TTGATGGCAC | 60
| ATAGACAAGC | TTCTGATTTG | GAAATCCCGA | AAGATGACGT | GAAACAGTTA | CTATCCAAGG | 120
| AGCAGCAACA | CATTCAATCT | GTTAGATGGC | TTGGCTATAT | TCAGCCACCT | CAAACAGGAG | 180
| ACTATGTATT | GTCAACCTCA | TCCGACCAAC | AGGTCGTGAT | TGAACTCGAT | GGAAAAACCA | 240
| TTGTCAATCA | AACTTCTATG | ACAGAACCGA | TTCAACTCGA | AAAAGATAAG | CTCTATAAAA | 300
| TTAGAATTGA | ATATGTCCCA | GAAGATACAA | AGAACAAGA | GAACCTCCTT | GACTTTCAGC | 360
| TCAACTGGTC | GATTTCAGGA | TCAGAGATAG | AACCAATTCC | GGAGAATGCT | TTCCATTTAC | 420
| CAAATTTTTC | TCGTAAACAA | GATCAAGAGA | AAATCATCCC | TGAAACCAGT | TTGTTTCAGG | 480
| AACAAGGAGA | TGAGAAAAAA | GTATCTCGCA | GTAAGAGATC | TTTAGCTACA | AATCCTATCC | 540
| GTGATACAGA | TGATGATAGT | ATTTATGATG | AATGGGAAAC | GGAAGGATAC | ACGATACGGG | 600
| AACAAATAGC | AGTGAAATGG | GACGATTCTA | TGAAGGATAG | AGGTTATACC | AAATATGTGT | 660
| CAAACCCCTA | TAAGTCTCAT | ACAGTAGGAG | ATCCATACAC | AGATTGGGAA | AAAGCGGCTG | 720

-continued

```
GCCGTATCGA TAACGGTGTC AAAGCAGAAG CCAGAAATCC TTTAGTCGCG GCCTATCCAA      780

CTGTTGGTGT ACATATGGAA AGATTAATTG TCTCCGAAAA ACAAAATATA TCAACAGGGC      840

TTGGAAAAAC TGTATCTGCG TCTATGTCCG CAAGCAATAC CGCAGCGATT ACGGCAGGTA      900

TTGATGCAAC AGCCGGTGCC TCTTTACTCG GGCCATCTGG AAGTGTCACG GCTCATTTTT      960

CTTATACAGG ATCTAGTACA TCCACCGTTG AAGATAGCTC CAGCCGGAAT GGAGTCAAG     1020

ACCTTGGGAT CGATACGGGA CAATCTGCAT ATTTAAATGC CAAATGTACG ATATAA        1076
```

(2) INFORMATION FOR SEQ ID NO:19:

(i) SEQUENCE CHARACTERISTICS:
        (A) LENGTH: 357 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: 10E1

(xi) SEQUENCE DESCRIPTION: SEQ ID NO:19:

```
Gly Leu Leu Gly Tyr Tyr Phe Gln Asp Gln Lys Phe Gln Gln Leu Ala
1               5                   10                  15

Leu Met Ala His Arg Gln Ala Ser Asp Leu Glu Ile Pro Lys Asp Asp
            20                  25                  30

Val Lys Gln Leu Leu Ser Lys Glu Gln Gln His Ile Gln Ser Val Arg
        35                  40                  45

Trp Leu Gly Tyr Ile Gln Pro Pro Gln Thr Gly Asp Tyr Val Leu Ser
    50                  55                  60

Thr Ser Asp Gln Gln Val Val Ile Glu Leu Asp Gly Lys Thr Ile
65                  70                  75                  80

Val Asn Gln Thr Ser Met Thr Glu Pro Ile Gln Leu Glu Lys Asp Lys
                85                  90                  95

Leu Tyr Lys Ile Arg Ile Glu Tyr Val Pro Glu Asp Thr Lys Glu Gln
            100                 105                 110

Glu Asn Leu Leu Asp Phe Gln Leu Asn Trp Ser Ile Ser Gly Ser Glu
        115                 120                 125

Ile Glu Pro Ile Pro Glu Asn Ala Phe His Leu Pro Asn Phe Ser Arg
    130                 135                 140

Lys Gln Asp Gln Glu Lys Ile Ile Pro Glu Thr Ser Leu Phe Gln Glu
145                 150                 155                 160

Gln Gly Asp Glu Lys Lys Val Ser Arg Ser Lys Arg Ser Leu Ala Thr
                165                 170                 175

Asn Pro Ile Arg Asp Thr Asp Asp Ser Ile Tyr Asp Glu Trp Glu
            180                 185                 190

Thr Glu Gly Tyr Thr Ile Arg Glu Gln Ile Ala Val Lys Trp Asp Asp
        195                 200                 205

Ser Met Lys Asp Arg Gly Tyr Thr Lys Tyr Val Ser Asn Pro Tyr Lys
    210                 215                 220

Ser His Thr Val Gly Asp Pro Tyr Thr Asp Trp Glu Lys Ala Ala Gly
225                 230                 235                 240

Arg Ile Asp Asn Gly Val Lys Ala Glu Ala Arg Asn Pro Leu Val Ala
                245                 250                 255

Ala Tyr Pro Thr Val Gly Val His Met Glu Arg Leu Ile Val Ser Glu
            260                 265                 270
```

```
Lys Gln Asn Ile Ser Thr Gly Leu Gly Lys Thr Val Ser Ala Ser Met
        275                 280                 285

Ser Ala Ser Asn Thr Ala Ala Ile Thr Ala Gly Ile Asp Ala Thr Ala
        290                 295                 300

Gly Ala Ser Leu Leu Gly Pro Ser Gly Ser Val Thr Ala His Phe Ser
305                 310                 315                 320

Tyr Thr Gly Ser Ser Thr Ser Thr Val Glu Asp Ser Ser Ser Arg Asn
                325                 330                 335

Trp Ser Gln Asp Leu Gly Ile Asp Thr Gly Gln Ser Ala Tyr Leu Asn
                340                 345                 350

Ala Lys Cys Thr Ile
        355

(2) INFORMATION FOR SEQ ID NO:20:

(i) SEQUENCE CHARACTERISTICS:
        (A) LENGTH: 1045 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 31J2

(xi) SEQUENCE DESCRIPTION: SEQ ID NO:20:

TGGGTTACTT GGGTATTATT TTAAAGGAAA AGATTTTAAT AATCTTACTA TATTTGCTCC      60

AACACGTGAG AATACTCTTA TTTATGATTT AGAAACAGCG AATTCTTTAT TAGATAAGCA    120

ACAACAAACC TATCAATCTA TTCGTTGGAT CGGTTTAATA AAAAGCAAAA AAGCTGGAGA    180

TTTTACCTTT CAATTATCGG ATGATGAGCA TGCTATTATA GAAATCGATG GGAAAGTTAT    240

TTCGCAAAAA GGCCAAAAGA AACAAGTTGT TCATTTAGAA AAAGATAAAT TAGTTCCCAT    300

CAAAATTGAA TATCAATCTG ATAAAGCGTT AAACCCAGAT AGTCAAATGT TTAAAGAATT    360

GAAATTATTT AAAATAAATA GTCAAAAACA ATCTCAGCAA GTGCAACAAG ACGAATTGAG    420

AAATCCTGAA TTTGGTAAAG AAAAAACTCA AACATATTTA AAGAAAGCAT CGAAAAGCAG    480

CTTGTTTAGC AATAAAAGTA AACGAGATAT AGATGAAGAT ATAGATGAGG ATACAGATAC    540

AGATGGAGAT GCCATTCCTG ATGTATGGGA AGAAAATGGG TATACCATCA AAGGAAGAGT    600

AGCTGTTAAA TGGGACGAAG GATTAGCTGA TAAGGGATAT AAAAAGTTTG TTTCCAATCC    660

TTTTAGACAG CACACTGCTG GTGACCCCTA TAGTGACTAT GAAAAGGCAT CAAAAGATTT    720

GGATTTATCT AATGCAAAAG AAACATTTAA TCCATTGGTG GCTGCTTTTC CAAGTGTCAA    780

TGTTAGCTTG GAAAATGTCA CCATATCAAA AGATGAAAAT AAAACTGCTG AAATTGCGTC    840

TACTTCATCG AATAATTGGT CCTATACAAA TACAGAGGGG GCATCTATTG AAGCTGGAAT    900

TGGACCAGAA GGTTTGTTGT CTTTTGGAGT AAGTGCCAAT TATCAACATT CTGAAACAGT    960

GGCCAAAGAG TGGGGTACAA CTAAGGGAGA CGCAACACAA TATAATACAG CTTCAGCAGG   1020

ATATCTAAAT GCCAATGTAC GATAT                                        1045

(2) INFORMATION FOR SEQ ID NO:21:

(i) SEQUENCE CHARACTERISTICS:
        (A) LENGTH: 348 amino acids
        (B) TYPE: amino acid
        (C) STRANDEDNESS: single
        (D) TOPOLOGY: linear
```

(ii) MOLECULE TYPE: peptide (vi) ORIGINAL SOURCE:
    (C) INDIVIDUAL ISOLATE: 31J2

(xi) SEQUENCE DESCRIPTION: SEQ ID NO:21:

```
Gly Leu Leu Gly Tyr Tyr Phe Lys Gly Lys Asp Phe Asn Asn Leu Thr
1               5                   10                  15

Ile Phe Ala Pro Thr Arg Glu Asn Thr Leu Ile Tyr Asp Leu Glu Thr
                20                  25                  30

Ala Asn Ser Leu Leu Asp Lys Gln Gln Gln Thr Tyr Gln Ser Ile Arg
            35                  40                  45

Trp Ile Gly Leu Ile Lys Ser Lys Lys Ala Gly Asp Phe Thr Phe Gln
50                      55                  60

Leu Ser Asp Asp Glu His Ala Ile Ile Glu Ile Asp Gly Lys Val Ile
65                  70                  75                  80

Ser Gln Lys Gly Gln Lys Gln Val Val His Leu Glu Lys Asp Lys
                85                  90                  95

Leu Val Pro Ile Lys Ile Glu Tyr Gln Ser Asp Lys Ala Leu Asn Pro
                100                 105                 110

Asp Ser Gln Met Phe Lys Glu Leu Lys Leu Phe Lys Ile Asn Ser Gln
            115                 120                 125

Lys Gln Ser Gln Gln Val Gln Gln Asp Glu Leu Arg Asn Pro Glu Phe
130                     135                 140

Gly Lys Glu Lys Thr Gln Thr Tyr Leu Lys Lys Ala Ser Lys Ser Ser
145                 150                 155                 160

Leu Phe Ser Asn Lys Ser Lys Arg Asp Ile Asp Glu Asp Ile Asp Glu
                165                 170                 175

Asp Thr Asp Thr Asp Gly Asp Ala Ile Pro Asp Val Trp Glu Glu Asn
            180                 185                 190

Gly Tyr Thr Ile Lys Gly Arg Val Ala Val Lys Trp Asp Glu Gly Leu
                195                 200                 205

Ala Asp Lys Gly Tyr Lys Lys Phe Val Ser Asn Pro Phe Arg Gln His
210                 215                 220

Thr Ala Gly Asp Pro Tyr Ser Asp Tyr Glu Lys Ala Ser Lys Asp Leu
225                 230                 235                 240

Asp Leu Ser Asn Ala Lys Glu Thr Phe Asn Pro Leu Val Ala Ala Phe
                245                 250                 255

Pro Ser Val Asn Val Ser Leu Glu Asn Val Thr Ile Ser Lys Asp Glu
                260                 265                 270

Asn Lys Thr Ala Glu Ile Ala Ser Thr Ser Ser Asn Asn Trp Ser Tyr
            275                 280                 285

Thr Asn Thr Glu Gly Ala Ser Ile Glu Ala Gly Ile Gly Pro Glu Gly
            290                 295                 300

Leu Leu Ser Phe Gly Val Ser Ala Asn Tyr Gln His Ser Glu Thr Val
305                 310                 315                 320

Ala Lys Glu Trp Gly Thr Thr Lys Gly Asp Ala Thr Gln Tyr Asn Thr
                325                 330                 335

Ala Ser Ala Gly Tyr Leu Asn Ala Asn Val Arg Tyr
            340                 345
```

(2) INFORMATION FOR SEQ ID NO:22:

(i) SEQUENCE CHARACTERISTICS:
        (A) LENGTH: 1641 base pairs (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 33D2

(xi) SEQUENCE DESCRIPTION: SEQ ID NO:22:

| | | | | | |
|---|---|---|---|---|---|
| CCAAAGGGGG | NTTAAACCNG | GANGGTTNNN | TNNTTNNTTN | TNGAANCCCA | NTTGGAAACC | 60 |
| CNATNAAATT | CNTGGTTANT | GGTNGTGAGT | GNNTNTTTTA | NCNGAGNTTG | CCCNTTTGNN | 120 |
| TACCNGGATT | TNAAGGCAGA | ANTTNTTNNT | NGCTNNTTAA | AGGTTNTGNT | TNTNANTGAA | 180 |
| TTTTTTNGGN | TTTGCCCAAA | AAACAAGGAT | GAATCCTGTT | ATTCCNCCCT | NGAAAAAATN | 240 |
| GAAACGGAAC | AACGTGAGTA | TGATAAACAT | CTTTTACAAA | CTGCGACATC | TTGTTGAAAA | 300 |
| TGCCTTTTTT | GAAAANNTAA | AAGGTTTCGT | GGCATTGCCA | CACGTTATAC | AAAAACCACG | 360 |
| TCTGCTTTTA | GAGGGGCTGT | TACCTTGGCT | GCTATTTCTC | TGTGGTTGAA | TCTCGTATAG | 420 |
| ACACTATCTA | GTCTATACAT | CTTATCTTTT | CATCATGATT | CCAGTCGTAC | ATTTACTCAA | 480 |
| AAATAGAAAG | GATGACCCCT | ATGCAATTAA | AAAATGTATA | CAAATGTTTA | ACCATTACAG | 540 |
| CGCTTTTGGC | TCAAATCGCC | GCCTTCCCGT | CTTCCTCTTT | TGCGGAAGAC | GGGAAGAAAA | 600 |
| AAGAAGAAAA | TACAGCTAAA | ACAGAACATC | AACAGAAAAA | AGAAACAAAA | CCAGTTGTGG | 660 |
| GATTAATTGG | TCACTATTTT | ACTGATGATC | AGTTTACTAA | CACAGCATTT | ATTCAAGTAG | 720 |
| GAGAAAAAAG | TAAATTACTA | GATTCAAAAA | TAGTAAAGCA | AGATATGTCC | AATTTGAAAT | 780 |
| CCATTCGATG | GGAAGGAAAT | GTGAAACCTC | CTGAAACAGG | AGAATATCTA | CTTTCCACGT | 840 |
| CCTCTAATGA | AAATGTTACA | GTAAAAGTAG | ATGGAGAAAC | TGTTATTAAC | AAAGCTAACA | 900 |
| TGGAAAAAGC | AATGAAACTC | GAAAAGATA | AACCACACTC | TATTGAAATT | GAATATCATG | 960 |
| TTCCTGAGAA | CGGGAAGGAA | CTACAATTAT | TTTGGCAAAT | AAATGACCAG | AAAGCTGTTA | 1020 |
| AAATCCCAGA | AAAAAACATA | CTATCACCAA | ATCTTTCTGA | ACAGATACAA | CCGCAACAGC | 1080 |
| GTTCAACTCA | ATCTCAACAA | AATCAAAATG | ATAGGGATGG | GGATAAAATC | CCTGATAGTT | 1140 |
| TAGAAGAAAA | TGGCTATACA | TTTAAAGACG | GTGCGATTGT | TGCCTGGAAC | GATTCCTATG | 1200 |
| CAGCACTAGG | CTATAAAAAA | TACATATCCA | ATTCTAATAA | GGCTAAAACA | GCTGCTGACC | 1260 |
| CCTATACGGA | CTTTGAAAAA | GTAACAGGAC | ACATGCCGGA | GGCAACTAAA | GATGAAGTAA | 1320 |
| AAGATCCACT | AGTAGCCGCT | TATCCCTCGG | TAGGTGTTGC | TATGGAAAAA | TTTCATTTTT | 1380 |
| CTAGAAATGA | AACGGTCACT | GAAGGAGACT | CAGGTACTGT | TTCAAAAACC | GTAACCAATA | 1440 |
| CAAGCACAAC | AACAAATAGC | ATCGATGTTG | GGGGATCCAT | TGGATGGGGA | GAAAAAGGAT | 1500 |
| TTTCTTTTTC | ATTCTCTCCC | AAATATACGC | ATTCTTGGAG | TAATAGTACC | GCTGTTGCTG | 1560 |
| ATACTGAAAG | TAGCACATGG | TCTTCACAAT | TAGCGTATAA | TCCTTCAGAA | CGTGCTTTCT | 1620 |
| TAAATGCCAA | TATACGATAT | A | | | | 1641 |

(2) INFORMATION FOR SEQ ID NO:23:

(i) SEQUENCE CHARACTERISTICS:
        (A) LENGTH: 327 amino acids
        (B) TYPE: amino acid
        (C) STRANDEDNESS: single
        (D) TOPOLOGY: linear (ii) MOLECULE TYPE: peptide (vi) ORIGINAL SOURCE:

(C) INDIVIDUAL ISOLATE: 33D2

(xi) SEQUENCE DESCRIPTION: SEQ ID NO:23:

```
Gly Leu Ile Gly His Tyr Phe Thr Asp Asp Gln Phe Thr Asn Thr Ala
1               5                   10                  15

Phe Ile Gln Val Gly Glu Lys Ser Lys Leu Asp Ser Lys Ile Val
            20                  25                  30

Lys Gln Asp Met Ser Asn Leu Lys Ser Ile Arg Trp Glu Gly Asn Val
            35                  40                  45

Lys Pro Pro Glu Thr Gly Glu Tyr Leu Leu Ser Thr Ser Ser Asn Glu
50                          55                  60

Asn Val Thr Val Lys Val Asp Gly Glu Thr Val Ile Asn Lys Ala Asn
65                  70                  75                  80

Met Glu Lys Ala Met Lys Leu Glu Lys Asp Lys Pro His Ser Ile Glu
                85                  90                  95

Ile Glu Tyr His Val Pro Glu Asn Gly Lys Glu Leu Gln Leu Phe Trp
                100                 105                 110

Gln Ile Asn Asp Gln Lys Ala Val Lys Ile Pro Glu Lys Asn Ile Leu
            115                 120                 125

Ser Pro Asn Leu Ser Glu Gln Ile Gln Pro Gln Gln Arg Ser Thr Gln
130                 135                 140

Ser Gln Gln Asn Gln Asn Asp Arg Asp Gly Asp Lys Ile Pro Asp Ser
145                 150                 155                 160

Leu Glu Glu Asn Gly Tyr Thr Phe Lys Asp Gly Ala Ile Val Ala Trp
                165                 170                 175

Asn Asp Ser Tyr Ala Ala Leu Gly Tyr Lys Lys Tyr Ile Ser Asn Ser
            180                 185                 190

Asn Lys Ala Lys Thr Ala Ala Asp Pro Tyr Thr Asp Phe Glu Lys Val
            195                 200                 205

Thr Gly His Met Pro Glu Ala Thr Lys Asp Glu Val Lys Asp Pro Leu
            210                 215                 220

Val Ala Ala Tyr Pro Ser Val Gly Val Ala Met Glu Lys Phe His Phe
225                 230                 235                 240

Ser Arg Asn Glu Thr Val Thr Glu Gly Asp Ser Gly Thr Val Ser Lys
                245                 250                 255

Thr Val Thr Asn Thr Ser Thr Thr Thr Asn Ser Ile Asp Val Gly Gly
                260                 265                 270

Ser Ile Gly Trp Gly Glu Lys Gly Phe Ser Phe Ser Phe Ser Pro Lys
            275                 280                 285

Tyr Thr His Ser Trp Ser Asn Ser Thr Ala Val Ala Asp Thr Glu Ser
            290                 295                 300

Ser Thr Trp Ser Ser Gln Leu Ala Tyr Asn Pro Ser Glu Arg Ala Phe
305                 310                 315                 320

Leu Asn Ala Asn Ile Arg Tyr
                325
```

(2) INFORMATION FOR SEQ ID NO:24:

(i) SEQUENCE CHARACTERISTICS:
  (A) LENGTH: 1042 base pairs
  (B) TYPE: nucleic acid
  (C) STRANDEDNESS: single
  (D) TOPOLOGY: linear (ii) MOLECULE TYPE: DNA (genomic)

(vi) ORIGINAL SOURCE:

(C) INDIVIDUAL ISOLATE: 66D3

(xi) SEQUENCE DESCRIPTION: SEQ ID NO:24:

| | | | | | |
|---|---|---|---|---|---|
| TTAATTGGGT | ACTATTTTAA | AGGAAAAGAT | TTTAATAATC | TTACTATATT | TGCTCCAACA | 60 |
| CGTGAGAATA | CTCTTATTTA | TGATTTAGAA | ACAGCGAATT | CTTTATTAGA | TAAGCAACAA | 120 |
| CAAACCTATC | AATCTATTCG | TTGGATCGGT | TTAATAAAAA | GCAAAAAAGC | TGGAGATTTT | 180 |
| ACCTTTCAAT | TATCGGATGA | TGAGCATGCT | ATTATAGAAA | TCGATGGGAA | AGTTATTTCG | 240 |
| CAAAAAGGCC | AAAAGAAACA | AGTTGTTCAT | TTAGAAAAAG | ATAAATTAGT | TCCCATCAAA | 300 |
| ATTGAATATC | AATCTGATAA | AGCGTTAAAC | CCAGATAGTC | AAATGTTTAA | AGAATTGAAA | 360 |
| TTATTTAAAA | TAAATAGTCA | AAAACAATCT | CAGCAAGTGC | AACAAGACGA | ATTGAGAAAT | 420 |
| CCTGAATTTG | GTAAAGAAAA | AACTCAAACA | TATTTAAAGA | AAGCATCGAA | AAGCAGCCTG | 480 |
| TTTAGCAATA | AAAGTAAACG | AGATATAGAT | GAAGATATAG | ATGAGGATAC | AGATACAGAT | 540 |
| GGAGATGCCA | TTCCTGATGT | ATGGGAAGAA | ATGGGTATA | CCATCAAAGG | AAGAGTAGCT | 600 |
| GTTAAATGGG | ACGAAGGATT | AGCTGATAAG | GGATATAAAA | AGTTTGTTTC | CAATCCTTTT | 660 |
| AGACAGCACA | CTGCTGGTGA | CCCCTATAGT | GACTATGAAA | AGGCATCAAA | AGATTTGGAT | 720 |
| TTATCTAATG | CAAAAGAAAC | ATTTAATCCA | TTGGTGGCTG | CTTTTCCAAG | TGTCAATGTT | 780 |
| AGCTTGGAAA | ATGTCACCAT | ATCAAAAGAT | GAAAATAAAA | CTGCTGAAAT | TGCGTCTACT | 840 |
| TCATCGAATA | ATTGGTCCTA | TACAAATACA | GAGGGGGCAT | CTATTGAAGC | TGGAATTGGA | 900 |
| CCAGAAGGTT | TGTTGTCTTT | TGGAGTAAGT | GCCAATTATC | AACATTCTGA | AACAGTGGCC | 960 |
| AAAGAGTGGG | GTACAACTAA | GGGAGACGCA | ACACAATATA | ATACAGCTTC | AGCAGGATAT | 1020 |
| CTAAATGCCA | ATGTACGATA | TA | | | | 1042 |

(2) INFORMATION FOR SEQ ID NO:25:

(i) SEQUENCE CHARACTERISTICS:
      (A) LENGTH: 347 amino acids
      (B) TYPE: amino acid
      (C) STRANDEDNESS: single
      (D) TOPOLOGY: linear (ii) MOLECULE TYPE: peptide (vi) ORIGINAL SOURCE:
      (C) INDIVIDUAL ISOLATE: 66D3

(xi) SEQUENCE DESCRIPTION: SEQ ID NO:25:

```
Leu Ile Gly Tyr Tyr Phe Lys Gly Lys Asp Phe Asn Asn Leu Thr Ile
1               5                   10                  15

Phe Ala Pro Thr Arg Glu Asn Thr Leu Ile Tyr Asp Leu Glu Thr Ala
            20                  25                  30

Asn Ser Leu Leu Asp Lys Gln Gln Gln Thr Tyr Gln Ser Ile Arg Trp
        35                  40                  45

Ile Gly Leu Ile Lys Ser Lys Lys Ala Gly Asp Phe Thr Phe Gln Leu
    50                  55                  60

Ser Asp Asp Glu His Ala Ile Ile Glu Ile Asp Gly Lys Val Ile Ser
65                  70                  75                  80

Gln Lys Gly Gln Lys Lys Gln Val Val His Leu Glu Lys Asp Lys Leu
                85                  90                  95

Val Pro Ile Lys Ile Glu Tyr Gln Ser Asp Lys Ala Leu Asn Pro Asp
            100                 105                 110

Ser Gln Met Phe Lys Glu Leu Lys Leu Phe Lys Ile Asn Ser Gln Lys
        115                 120                 125
```

```
Gln Ser Gln Gln Val Gln Gln Asp Glu Leu Arg Asn Pro Glu Phe Gly
    130                 135                 140
Lys Glu Lys Thr Gln Thr Tyr Leu Lys Lys Ala Ser Lys Ser Ser Leu
145                 150                 155                 160
Phe Ser Asn Lys Ser Lys Arg Asp Ile Asp Glu Asp Ile Asp Glu Asp
                165                 170                 175
Thr Asp Thr Asp Gly Asp Ala Ile Pro Asp Val Trp Glu Glu Asn Gly
            180                 185                 190
Tyr Thr Ile Lys Gly Arg Val Ala Val Lys Trp Asp Glu Gly Leu Ala
        195                 200                 205
Asp Lys Gly Tyr Lys Lys Phe Val Ser Asn Pro Phe Arg Gln His Thr
    210                 215                 220
Ala Gly Asp Pro Tyr Ser Asp Tyr Glu Lys Ala Ser Lys Asp Leu Asp
225                 230                 235                 240
Leu Ser Asn Ala Lys Glu Thr Phe Asn Pro Leu Val Ala Ala Phe Pro
                245                 250                 255
Ser Val Asn Val Ser Leu Glu Asn Val Thr Ile Ser Lys Asp Glu Asn
            260                 265                 270
Lys Thr Ala Glu Ile Ala Ser Thr Ser Ser Asn Asn Trp Ser Tyr Thr
        275                 280                 285
Asn Thr Glu Gly Ala Ser Ile Glu Ala Gly Ile Gly Pro Glu Gly Leu
    290                 295                 300
Leu Ser Phe Gly Val Ser Ala Asn Tyr Gln His Ser Glu Thr Val Ala
305                 310                 315                 320
Lys Glu Trp Gly Thr Thr Lys Gly Asp Ala Thr Gln Tyr Asn Thr Ala
                325                 330                 335
Ser Ala Gly Tyr Leu Asn Ala Asn Val Arg Tyr
            340                 345
```

(2) INFORMATION FOR SEQ ID NO:26:

(i) SEQUENCE CHARACTERISTICS:
        (A) LENGTH: 1278 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 68F (xi) SEQUENCE DESCRIPTION: SEQ ID NO:26:

```
TGGATTACTT GGGTACTATT TTAAAGGGAA AGATTTTAAT GATCTTACTG TATTTGCACC      60

AACGCGTGGG AATACTCTTG TATATGATCA ACAAACAGCA AATACATTAC TAAATCAAAA     120

ACAACAAGAC TTTCAGTCTA TTCGTTGGGT TGGTTTAATT CAAAGTAAAG AAGCAGGCGA     180

TTTTACATTT AACTTATCAG ATGATGAACA TACGATGATA GAAATCGATG GAAAGTTAT      240

TTCTAATAAA GGGAAAGAAA AACAAGTTGT CCATTTAGAA AAAGGACAGT TCGTTTCTAT     300

CAAAATAGAA TATCAAGCTG ATGAACCATT TAATGCGGAT AGTCAAACCT TAAAAATTT      360

GAAACTCTTT AAAGTAGATA CTAAGCAACA GTCCCAGCAA ATTCAACTAG ATGAATTAAG     420

AAACCCTGAA TTTAATAAAA AGAAACACA AGAATTTCTA ACAAAAGCAA CAAAAACAAA      480

CCTTATTACT CAAAAAGTGA AGAGTACTAG GGATGAAGAC ACGGATACAG ATGGAGATTC     540

TATTCCAGAC ATTTGGGAAG AAAATGGGTA TACCATCCAA AATAAGATTG CCGTCAAATG     600
```

```
GGATGATTCA TTAGCAAGTA AAGGATATAC GAAATTTGTT TCAAACCCAC TAGATACTCA      660

CACGGTTGGA GATCCTTATA CAGATTATGA AAAAGCAGCA AGGGATTTAG ATTTGTCAAA      720

TGCAAAAGAA ACATTTAACC CATTAGTTGC GGCTTTTCCA AGTGTGAATG TGAGTATGGA      780

AAAAGTGATA TTGTCTCCAG ATGAGAACTT ATCAAATAGT ATCGAGTCTC ATTCATCTAC      840

GAATTGGTCG TATACGAATA CAGAAGGGGC TTCTATTGAA GCTGGTGGGG GAGCATTAGG      900

CCTATCTTTT GGTGTAAGTG CAAACTATCA ACATTCTGAA ACAGTTGGGT ATGAATGGGG      960

AACATCTACG GGAAATACTT CGCAATTTAA TACAGCTTCA GCGGGGTATT TAAATGCGAA     1020

TGTTCGCTAC AATAACGTGG GAACGGGTGC AATCTATGAT GTAAAGCCAA CAACGAGTTT     1080

TGTATTAAAT AAAGATACCA TCGCAACGAT AACAGCAAAA TCGAATACGA CTGCATTAAG     1140

TATCTCACCA GGACAAAGTT ATCCGAAACA AGGTCAAAAT GGAATCGCGA TCACATCGAT     1200

GGATGATTTT AACTCACATC CGATTACATT GAATAAGCAA CAGGTAGGTC AACTGTTAAA     1260

TAATACCCAA TTAATCCA                                                   1278
```

(2) INFORMATION FOR SEQ ID NO:27:

(i) SEQUENCE CHARACTERISTICS:
        (A) LENGTH: 425 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: 68F (xi) SEQUENCE DESCRIPTION: SEQ ID NO:27:

```
Gly Leu Leu Gly Tyr Tyr Phe Lys Gly Lys Asp Phe Asn Asp Leu Thr
1               5                   10                  15

Val Phe Ala Pro Thr Arg Gly Asn Thr Leu Val Tyr Asp Gln Gln Thr
            20                  25                  30

Ala Asn Thr Leu Leu Asn Gln Lys Gln Gln Asp Phe Gln Ser Ile Arg
        35                  40                  45

Trp Val Gly Leu Ile Gln Ser Lys Glu Ala Gly Asp Phe Thr Phe Asn
    50                  55                  60

Leu Ser Asp Asp Glu His Thr Met Ile Glu Ile Asp Gly Lys Val Ile
65                  70                  75                  80

Ser Asn Lys Gly Lys Glu Lys Gln Val Val His Leu Glu Lys Gly Gln
                85                  90                  95

Phe Val Ser Ile Lys Ile Glu Tyr Gln Ala Asp Glu Pro Phe Asn Ala
            100                 105                 110

Asp Ser Gln Thr Phe Lys Asn Leu Lys Leu Phe Lys Val Asp Thr Lys
        115                 120                 125

Gln Gln Ser Gln Gln Ile Gln Leu Asp Glu Leu Arg Asn Pro Glu Phe
    130                 135                 140

Asn Lys Lys Glu Thr Gln Glu Phe Leu Thr Lys Ala Thr Lys Thr Asn
145                 150                 155                 160

Leu Ile Thr Gln Lys Val Lys Ser Thr Arg Asp Glu Asp Thr Asp Thr
                165                 170                 175

Asp Gly Asp Ser Ile Pro Asp Ile Trp Glu Glu Asn Gly Tyr Thr Ile
            180                 185                 190

Gln Asn Lys Ile Ala Val Lys Trp Asp Asp Ser Leu Ala Ser Lys Gly
        195                 200                 205
```

Tyr Thr Lys Phe Val Ser Asn Pro Leu Asp Thr His Thr Val Gly Asp
    210                 215                 220

Pro Tyr Thr Asp Tyr Glu Lys Ala Ala Arg Asp Leu Asp Leu Ser Asn
225                 230                 235                 240

Ala Lys Glu Thr Phe Asn Pro Leu Val Ala Ala Phe Pro Ser Val Asn
                245                 250                 255

Val Ser Met Glu Lys Val Ile Leu Ser Pro Asp Glu Asn Leu Ser Asn
            260                 265                 270

Ser Ile Glu Ser His Ser Ser Thr Asn Trp Ser Tyr Thr Asn Thr Glu
        275                 280                 285

Gly Ala Ser Ile Glu Ala Gly Gly Ala Leu Gly Leu Ser Phe Gly
    290                 295                 300

Val Ser Ala Asn Tyr Gln His Ser Glu Thr Val Gly Tyr Glu Trp Gly
305                 310                 315                 320

Thr Ser Thr Gly Asn Thr Ser Gln Phe Asn Thr Ala Ser Ala Gly Tyr
                325                 330                 335

Leu Asn Ala Asn Val Arg Tyr Asn Asn Val Gly Thr Gly Ala Ile Tyr
            340                 345                 350

Asp Val Lys Pro Thr Thr Ser Phe Val Leu Asn Lys Asp Thr Ile Ala
        355                 360                 365

Thr Ile Thr Ala Lys Ser Asn Thr Ala Leu Ser Ile Ser Pro Gly
    370                 375                 380

Gln Ser Tyr Pro Lys Gln Gly Gln Asn Gly Ile Ala Ile Thr Ser Met
385                 390                 395                 400

Asp Asp Phe Asn Ser His Pro Ile Thr Leu Asn Lys Gln Gln Val Gly
                405                 410                 415

Gln Leu Leu Asn Asn Thr Gln Leu Ile
            420                 425

(2) INFORMATION FOR SEQ ID NO:28:

(i) SEQUENCE CHARACTERISTICS:
        (A) LENGTH: 983 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 69AA2

(xi) SEQUENCE DESCRIPTION: SEQ ID NO:28:

TGGATTACTT GGGTACTATT TTACTGATGA TCAGTTTACT AACACAGCAT TTATTCAAGT      60

AGGAGAAAAA AGTAAATTAC TAGATTCAAA AATAGTAAAA CAAGATATGT CCAATTTGAA     120

ATCCATTCGA TGGGAAGGAA ATGTGAAACC TCCTGAAACA GGAGAATATC TACTTTCCAC     180

GTCCTCTAAT GAAATGTTA CAGTAAAAGT AGATGGAGAA ACTGTTATTA CAAAGCTAA      240

CATGGAAAAA GCAATGAAAC TCGAAAAAGA TAAACCACAC TCTATTGAAA TTGAATATCA     300

TGTTCCTGAG AACGGGAAGG AACTACAATT ATTTTGGCAA ATAAATGACC AGAAAGCTGT     360

TAAAATCCCA GAAAAAAACA TACTATCACC AAATCTTTCT GAACAGATAC AACCGCAACA     420

GCGTTCAACT CAATCTCAAC AAAATCAAAA TGATAGGGAT GGGGATAAAA TCCCTGATAG     480

TTTAGAAGAA AATGGCTATA CATTTAAAGA CGGTGCGATT GTTGCCTGGA ACGATTCCTA     540

TGCAGCACTA GGCTATAAAA AATACATATC CAATTCTAAT AAGGCTAAAA CAGCTGCTGA     600

CCCCTATACG GACTTTGAAA AGTAACAGG ACACATGCCG GAGGCAACTA AAGATGAAGT     660

```
AAAAGATCCA CTAGTAGCCG CTTATCCCTC GGTAGGTGTT GCTATGGAAA AATTTCATTT      720

TTCTAGAAAT GAAACGGTCA CTGAAGGAGA CTCAGGTACT GTTTCAAAAA CCGTAACCAA      780

TACAAGCACA ACAACAAATA GCATCGATGT TGGGGATCC ATTGGATGGG GAGAAAAAGG       840

ATTTTCTTTT TCATTCTCTC CCAAATATAC GCATTCTTGG AGTAATAGTA CCGCTGTTGC      900

TGATACTGAA AGTAGCACAT GGTCTTCACA ATTAGCGTAT AATCCTTCAG AACGTGCTNT      960

CTTAAATGCC AATAKACGAT NTA                                              983
```

(2) INFORMATION FOR SEQ ID NO:29:

(i) SEQUENCE CHARACTERISTICS:
        (A) LENGTH: 327 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: 69AA2

(xi) SEQUENCE DESCRIPTION: SEQ ID NO:29:

```
Gly Leu Leu Gly Tyr Tyr Phe Thr Asp Asp Gln Phe Thr Asn Thr Ala
1               5                   10                  15

Phe Ile Gln Val Gly Glu Lys Ser Lys Leu Leu Asp Ser Lys Ile Val
            20                  25                  30

Lys Gln Asp Met Ser Asn Leu Lys Ser Ile Arg Trp Glu Gly Asn Val
        35                  40                  45

Lys Pro Pro Glu Thr Gly Glu Tyr Leu Leu Ser Thr Ser Ser Asn Glu
    50                  55                  60

Asn Val Thr Val Lys Val Asp Gly Glu Thr Val Ile Asn Lys Ala Asn
65                  70                  75                  80

Met Glu Lys Ala Met Lys Leu Glu Lys Asp Lys Pro His Ser Ile Glu
                85                  90                  95

Ile Glu Tyr His Val Pro Glu Asn Gly Lys Glu Leu Gln Leu Phe Trp
            100                 105                 110

Gln Ile Asn Asp Gln Lys Ala Val Lys Ile Pro Glu Lys Asn Ile Leu
        115                 120                 125

Ser Pro Asn Leu Ser Glu Gln Ile Gln Pro Gln Gln Arg Ser Thr Gln
    130                 135                 140

Ser Gln Gln Asn Gln Asn Asp Arg Asp Gly Asp Lys Ile Pro Asp Ser
145                 150                 155                 160

Leu Glu Glu Asn Gly Tyr Thr Phe Lys Asp Gly Ala Ile Val Ala Trp
                165                 170                 175

Asn Asp Ser Tyr Ala Ala Leu Gly Tyr Lys Lys Tyr Ile Ser Asn Ser
            180                 185                 190

Asn Lys Ala Lys Thr Ala Ala Asp Pro Tyr Thr Asp Phe Glu Lys Val
        195                 200                 205

Thr Gly His Met Pro Glu Ala Thr Lys Asp Glu Val Lys Asp Pro Leu
    210                 215                 220

Val Ala Ala Tyr Pro Ser Val Gly Val Ala Met Glu Lys Phe His Phe
225                 230                 235                 240

Ser Arg Asn Glu Thr Val Thr Glu Gly Asp Ser Gly Thr Val Ser Lys
                245                 250                 255

Thr Val Thr Asn Thr Ser Thr Thr Asn Ser Ile Asp Val Gly Gly
            260                 265                 270
```

Ser Ile Gly Trp Gly Glu Lys Gly Phe Ser Phe Ser Phe Ser Pro Lys
        275                 280                 285

Tyr Thr His Ser Trp Ser Asn Ser Thr Ala Val Ala Asp Thr Glu Ser
        290                 295                 300

Ser Thr Trp Ser Ser Gln Leu Ala Tyr Asn Pro Ser Glu Arg Ala Xaa
305                 310                 315                 320

Leu Asn Ala Asn Xaa Arg Xaa
                325

(2) INFORMATION FOR SEQ ID NO:30:

(i) SEQUENCE CHARACTERISTICS:
        (A) LENGTH: 1075 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 168G1

(xi) SEQUENCE DESCRIPTION: SEQ ID NO:30:

```
TGGGTTAATT GGATATTATT TCCAGGATCA AAAATTTCAA CAACTCGCTT TAATGGTACA      60
TAGGCAAGCT TCTGATTTAA AAATACTGAA AGATGACGTG AAACATTTAC TATCCGAAGA     120
TCAACAACAC ATTCAATCAG TAAGGTGGAT AGGCTATATT AAGCCACCTA AAACAGGAGA     180
CTACGTATTG TCAACCTCAT CCGACCAACA GGTCATGATT GAACTAGATG GTAAAGTCAT     240
TCTCAATCAG GCTTCTATGA CAGAACCTGT TCAACTTGAA AAAGATAAAC CGTATAAAAT     300
TAAAATTGAA TATGTTCCGG AACAAACAGA AACACAAGAT ACGCTTCTTG ATTTTAAACT     360
GAACTGGTCT TTTTCAGGCG GAAAAACAGA AACGATTCCA GAAAATGCAT TTCTATTACC     420
AGACCTTTCT CGTAAACAAG ATCAAGAAAA GCTTATTCCT GAGGCAAGTT TATTTCAGAA     480
ACCTGGAGAC GAGAAAAAAA TATCTCGAAG TAAACGGTCC TTTAACTACA GATTCTCTAT     540
ATGATACAAG ATGATGATGG GATTTCGGAT GCGTGGGAAA CAGAAGGATA CACGATACAA     600
AGACAACTGG CAGTGAAATG GGACGATTCT ATGAAGGATC GAGGGTATAC CAAATATGTA     660
TCTAATCCCT ATAATTCCCA TACAGTAGGG GATCCATACA CAGATTGGGA AAAAGCGGCT     720
GGACGTATTG ATAAGGCGAT CAAAGGAGAA GCTAGGAATC CTTTAGTCGC GGCCTATCCA     780
ACCGTTGGTG TACATATGGA AAAACTGATT GTCTCCGAGA AACAAAACAT ATCAACTGGA     840
CTCGGAAAAA CAATATCTGC GTCAATGTCT GCAAGTAATA CCGCAGCGAT TACAGCGGGC     900
ATTGATACGA CGGCTGGTGC TTCTTTACTT GGACCGTCTG GAAGCGTCAC GGCTCATTTT     960
TCTGATACAG GATCCAGTAC ATCCACTGTT GAAAATAGCT CAAGTAATAA TTGGAGTCAA    1020
GATCTTGGAA TCGATACGGG ACAATCTGCA TATTTAAATG CCAATGTACG ATATA         1075
```

(2) INFORMATION FOR SEQ ID NO:31:

(i) SEQUENCE CHARACTERISTICS:
        (A) LENGTH: 2645 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 177c8

-continued (xi) SEQUENCE DESCRIPTION: SEQ ID NO:31:

```
ATGAAGAAGA AGTTAGCAAG TGTTGTAACG TGTACGTTAT TAGCTCCTAT GTTTTTGAAT      60
GGAAATGTGA ATGCTGTTTA CGCAGACAGC AAAACAAATC AAATTTCTAC AACACAGAAA     120
AATCAACAGA AAGAGATGGA CCGAAAAGGA TTACTTGGGT ATTATTTCAA AGGAAAAGAT     180
TTTAGTAATC TTACTATGTT TGCACCGACA CGTGATAGTA CTCTTATTTA TGATCAACAA     240
ACAGCAAATA AACTATTAGA TAAAAAACAA CAAGAATATC AGTCTATTCG TTGGATTGGT     300
TTGATTCAGA GTAAAGAAAC GGGAGATTTC ACATTTAACT TATCTGAGGA TGAACAGGCA     360
ATTATAGAAA TCAATGGGAA AATTATTTCT AATAAAGGGA AGAAAAGCA AGTTGTCCAT      420
TTAGAAAAAG GAAAATTAGT TCCAATCAAA ATAGAGTATC AATCAGATAC AAAATTTAAT     480
ATTGACAGTA AAACATTTAA AGAACTTAAA TTATTTAAAA TAGATAGTCA AAACCAACCC     540
CAGCAAGTCC AGCAAGATGA ACTGAGAAAT CCTGAATTTA ACAAGAAAGA ATCACAGGAA     600
TTCTTAGCGA AACCATCGAA AATAAATCTT TTCACTCAAA AAATGAAAAG GAAATTGAT      660
GAAGACACGG ATACGGATGG GGACTCTATT CCTGACCTTT GGGAAGAAAA TGGGTATACG     720
ATTCAAAATA GAATCGCTGT AAAGTGGGAC GATTCTYTAG CAAGTAAAGG GTATACGAAA     780
TTTGTTTCAA ATCCGCTAGA AAGTCACACA GTTGGTGATC CTTATACAGA TTATGAAAAG     840
GCAGCAAGAG ACCTAGATTT GTCAAATGCA AAGGAAACGT TAACCCATT GGTAGCTGCT      900
TTTCCAAGTG TGAATGTTAG TATGGAAAAG GTGATATTAT CACCAAATGA AAATTTATCC     960
AATAGTGTAG AGTCTCATTC ATCCACGAAT TGGTCTTATA CAAATACAGA AGGTGCTTCT    1020
GTTGAAGCGG GGATTGGACC AAAAGGTATT TCGTTCGGAG TTAGCGTAAA CTATCAACAC    1080
TCTGAAACAG TTGCACAAGA ATGGGAACA TCTACAGGAA ATACTTCGCA ATTCAATACG     1140
GCTTCAGCGG ATATTTAAA TGCAAATGTT CGATATAACA ATGTAGGAAC TGGTGCCATC     1200
TACGATGTAA AACCTACAAC AAGTTTTGTA TTAAATAACG ATACTATCGC AACTATTACG    1260
GCGAAATCTA ATTCTACAGC CTTAAATATA TCTCCTGGAG AAAGTTACCC GAAAAAAGGA    1320
CAAAATGGAA TCGCAATAAC ATCAATGGAT GATTTTAATT CCCATCCGAT TACATTAAAT    1380
AAAAAACAAG TAGATAATCT GCTAAATAAT AAACCTATGA TGTTGGAAAC AAACCAAACA    1440
GATGGTGTTT ATAAGATAAA AGATACACAT GGAAATATAG TAACTGGCGG AGAATGGAAT    1500
GGTGTCATAC AACAAATCAA GGCTAAAACA GCGTCTATTA TTGTGGATGA TGGGGAACGT    1560
GTAGCAGAAA AACGTGTAGC GGCAAAAGAT TATGAAAATC AGAAGATAA AACACCGTCT     1620
TTAACTTTAA AAGATGCCCT GAAGCTTTCA TATCCAGATG AAATAAAAGA AATAGAGGGA    1680
TTATTATATT ATAAAAACAA ACCGATATAC GAATCGAGCG TTATGACTTA CTTAGATGAA    1740
AATACAGCAA AGAAGTGAC CAAACAATTA AATGATACCA CTGGGAAATT TAAAGATGTA     1800
AGTCATTTAT ATGATGTAAA ACTGACTCCA AAAATGAATG TTACAATCAA ATTGTCTATA    1860
CTTTATGATA ATGCTGAGTC TAATGATAAC TCAATTGGTA AATGGACAAA CACAAATATT    1920
GTTTCAGGTG AAATAACGG AAAAAAACAA TATTCTTCTA ATAATCCGGA TGCTAATTTG     1980
ACATTAAATA CAGATGCTCA AGAAAAATTA AATAAAAATC GTACTATTAT ATAAGTTTAT    2040
ATATGAAGTC AGAAAAAAAC ACACAATGTG AGATTACTAT AGATGGGGAG ATTTATCCGA    2100
TCACTACAAA AACAGTGAAT GTGAATAAAG ACAATTACAA AAGATTAGAT ATTATAGCTC    2160
ATAATATAAA AAGTAATCCA ATTTCTTCAA TTCATATTAA AACGAATGAT GAAATAACTT    2220
TATTTTGGGA TGATATTTCT ATAACAGATG TAGCATCAAT AAAACCGGAA AATTTAACAG    2280
ATTCAGAAAT TAAACAGATT TATAGTAGGT ATGGTATTAA GTTAGAAGAT GGAATCCTTA    2340
```

-continued

```
TTGATAAAAA AGGTGGGATT CATTATGGTG AATTTATTAA TGAAGCTAGT TTTAATATTG      2400

AACCATTGCA AAATTATGTG ACAAAATATA AAGTTACTTA TAGTAGTGAG TTAGGACAAA      2460

ACGTGAGTGA CACACTTGAA AGTGATAAAA TTTACAAGGA TGGGACAATT AAATTTGATT      2520

TTACAAAATA TAGTRAAAAT GAACAAGGAT TATTTTATGA CAGTGGATTA AATTGGGACT      2580

TTAAAATTAA TGCTATTACT TATGATGGTA AAGAGATGAA TGTTTTTCAT AGATATAATA      2640

AATAG                                                                 2645
```

(2) INFORMATION FOR SEQ ID NO:32:

(i) SEQUENCE CHARACTERISTICS:
        (A) LENGTH: 881 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: 177C8

(xi) SEQUENCE DESCRIPTION: SEQ ID NO:32:

```
Met Lys Lys Lys Leu Ala Ser Val Val Thr Cys Thr Leu Leu Ala Pro
1               5                   10                  15

Met Phe Leu Asn Gly Asn Val Asn Ala Val Tyr Ala Asp Ser Lys Thr
            20                  25                  30

Asn Gln Ile Ser Thr Thr Gln Lys Asn Gln Gln Lys Glu Met Asp Arg
        35                  40                  45

Lys Gly Leu Leu Gly Tyr Tyr Phe Lys Gly Lys Asp Phe Ser Asn Leu
    50                  55                  60

Thr Met Phe Ala Pro Thr Arg Asp Ser Thr Leu Ile Tyr Asp Gln Gln
65                  70                  75                  80

Thr Ala Asn Lys Leu Leu Asp Lys Lys Gln Gln Glu Tyr Gln Ser Ile
                85                  90                  95

Arg Trp Ile Gly Leu Ile Gln Ser Lys Glu Thr Gly Asp Phe Thr Phe
            100                 105                 110

Asn Leu Ser Glu Asp Glu Gln Ala Ile Ile Glu Ile Asn Gly Lys Ile
        115                 120                 125

Ile Ser Asn Lys Gly Lys Glu Lys Gln Val Val His Leu Glu Lys Gly
    130                 135                 140

Lys Leu Val Pro Ile Lys Ile Glu Tyr Gln Ser Asp Thr Lys Phe Asn
145                 150                 155                 160

Ile Asp Ser Lys Thr Phe Lys Glu Leu Lys Leu Phe Lys Ile Asp Ser
                165                 170                 175

Gln Asn Gln Pro Gln Gln Val Gln Gln Asp Glu Leu Arg Asn Pro Glu
            180                 185                 190

Phe Asn Lys Lys Glu Ser Gln Glu Phe Leu Ala Lys Pro Ser Lys Ile
        195                 200                 205

Asn Leu Phe Thr Gln Lys Met Lys Arg Glu Ile Asp Glu Asp Thr Asp
    210                 215                 220

Thr Asp Gly Asp Ser Ile Pro Asp Leu Trp Glu Asn Gly Tyr Thr
225                 230                 235                 240

Ile Gln Asn Arg Ile Ala Val Lys Trp Asp Asp Ser Leu Ala Ser Lys
                245                 250                 255

Gly Tyr Thr Lys Phe Val Ser Asn Pro Leu Glu Ser His Thr Val Gly
            260                 265                 270
```

-continued

```
Asp Pro Tyr Thr Asp Tyr Glu Lys Ala Ala Arg Asp Leu Asp Leu Ser
        275                 280                 285
Asn Ala Lys Glu Thr Phe Asn Pro Leu Val Ala Ala Phe Pro Ser Val
    290                 295                 300
Asn Val Ser Met Glu Lys Val Ile Leu Ser Pro Asn Glu Asn Leu Ser
305                 310                 315                 320
Asn Ser Val Glu Ser His Ser Ser Thr Asn Trp Ser Tyr Thr Asn Thr
                325                 330                 335
Glu Gly Ala Ser Val Glu Ala Gly Ile Gly Pro Lys Gly Ile Ser Phe
                340                 345                 350
Gly Val Ser Val Asn Tyr Gln His Ser Glu Thr Val Ala Gln Glu Trp
                355                 360                 365
Gly Thr Ser Thr Gly Asn Thr Ser Gln Phe Asn Thr Ala Ser Ala Gly
        370                 375                 380
Tyr Leu Asn Ala Asn Val Arg Tyr Asn Asn Val Gly Thr Gly Ala Ile
385                 390                 395                 400
Tyr Asp Val Lys Pro Thr Thr Ser Phe Val Leu Asn Asn Asp Thr Ile
                405                 410                 415
Ala Thr Ile Thr Ala Lys Ser Asn Ser Thr Ala Leu Asn Ile Ser Pro
                420                 425                 430
Gly Glu Ser Tyr Pro Lys Lys Gly Gln Asn Gly Ile Ala Ile Thr Ser
            435                 440                 445
Met Asp Asp Phe Asn Ser His Pro Ile Thr Leu Asn Lys Lys Gln Val
        450                 455                 460
Asp Asn Leu Leu Asn Asn Lys Pro Met Met Leu Glu Thr Asn Gln Thr
465                 470                 475                 480
Asp Gly Val Tyr Lys Ile Lys Asp Thr His Gly Asn Ile Val Thr Gly
                485                 490                 495
Gly Glu Trp Asn Gly Val Ile Gln Gln Ile Lys Ala Lys Thr Ala Ser
                500                 505                 510
Ile Ile Val Asp Asp Gly Glu Arg Val Ala Glu Lys Arg Val Ala Ala
        515                 520                 525
Lys Asp Tyr Glu Asn Pro Glu Asp Lys Thr Pro Ser Leu Thr Leu Lys
        530                 535                 540
Asp Ala Leu Lys Leu Ser Tyr Pro Asp Glu Ile Lys Glu Ile Glu Gly
545                 550                 555                 560
Leu Leu Tyr Tyr Lys Asn Lys Pro Ile Tyr Glu Ser Ser Val Met Thr
                565                 570                 575
Tyr Leu Asp Glu Asn Thr Ala Lys Glu Val Thr Lys Gln Leu Asn Asp
            580                 585                 590
Thr Thr Gly Lys Phe Lys Asp Val Ser His Leu Tyr Asp Val Lys Leu
        595                 600                 605
Thr Pro Lys Met Asn Val Thr Ile Lys Leu Ser Ile Leu Tyr Asp Asn
        610                 615                 620
Ala Glu Ser Asn Asp Asn Ser Ile Gly Lys Trp Thr Asn Thr Asn Ile
625                 630                 635                 640
Val Ser Gly Gly Asn Asn Gly Lys Lys Gln Tyr Ser Ser Asn Asn Pro
                645                 650                 655
Asp Ala Asn Leu Thr Leu Asn Thr Asp Ala Gln Glu Lys Leu Asn Lys
            660                 665                 670
Asn Arg Asp Tyr Tyr Ile Ser Leu Tyr Met Lys Ser Glu Lys Asn Thr
        675                 680                 685
```

```
Gln Cys Glu Ile Thr Ile Asp Gly Glu Ile Tyr Pro Ile Thr Thr Lys
    690                 695                 700

Thr Val Asn Val Asn Lys Asp Asn Tyr Lys Arg Leu Asp Ile Ile Ala
705                 710                 715                 720

His Asn Ile Lys Ser Asn Pro Ile Ser Ser Ile His Ile Lys Thr Asn
                725                 730                 735

Asp Glu Ile Thr Leu Phe Trp Asp Asp Ile Ser Ile Thr Asp Val Ala
            740                 745                 750

Ser Ile Lys Pro Glu Asn Leu Thr Asp Ser Glu Ile Lys Gln Ile Tyr
            755                 760                 765

Ser Arg Tyr Gly Ile Lys Leu Glu Asp Gly Ile Leu Ile Asp Lys Lys
        770                 775                 780

Gly Gly Ile His Tyr Gly Glu Phe Ile Asn Glu Ala Ser Phe Asn Ile
785                 790                 795                 800

Glu Pro Leu Gln Asn Tyr Val Thr Lys Tyr Lys Val Thr Tyr Ser Ser
                805                 810                 815

Glu Leu Gly Gln Asn Val Ser Asp Thr Leu Glu Ser Asp Lys Ile Tyr
            820                 825                 830

Lys Asp Gly Thr Ile Lys Phe Asp Phe Thr Lys Tyr Ser Xaa Asn Glu
        835                 840                 845

Gln Gly Leu Phe Tyr Asp Ser Gly Leu Asn Trp Asp Phe Lys Ile Asn
    850                 855                 860

Ala Ile Thr Tyr Asp Gly Lys Glu Met Asn Val Phe His Arg Tyr Asn
865                 870                 875                 880

Lys (2) INFORMATION FOR SEQ ID NO:33:

(i) SEQUENCE CHARACTERISTICS:
        (A) LENGTH: 1022 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 177I8

(xi) SEQUENCE DESCRIPTION: SEQ ID NO:33:

TGGATTAATT GGGTATTATT TCAAAGGAAA AGATTTTAAT AATCTTACTA TGTTTGCACC      60

GACACGTGAT AATACCCTTA TGTATGACCA ACAAACAGCG AATGCATTAT TAGATAAAAA    120

ACAACAAGAA TATCAGTCCA TTCGTTGGAT TGGTTTGATT CAGAGTAAAG AAACGGGCGA    180

TTTCACATTT AACTTATCAA AGGATGAACA GGCAATTATA GAAATCGATG GAAAATCAT    240

TTCTAATAAA GGGAAAGAAA AGCAAGTTGT CCATTTAGAA AAAGAAAAAT TAGTTCCAAT    300

CAAAATAGAG TATCAATCAG ATACGAAATT TAATATTGAT AGTAAAACAT TTAAAGAACT    360

TAAATTATTT AAAATAGATA GTCAAAACCA ATCTCAACAA GTTCAACTGA GAAACCCTGA    420

ATTTAACAAA AAAGAATCAC AGGAATTTTT AGCAAAAGCA TCAAAAACAA ACCTTTTTAA    480

GCAAAAAATG AAAAGAGATA TTGATGAAGA TACGGATACA GATGGAGACT CCATTCCTGA    540

TCTTTGGGAA GAAAATGGGT ACACGATTCA AAATAAAGTT GCTGTCAAAT GGGATGATTC    600

GCTAGCAAGT AAGGGATATA CAAAATTTGT TTCGAATCCA TTAGACAGCC ACACAGTTGG    660

CGATCCCTAT ACTGATTATG AAAAGGCCGC AAGGGATTTA GATTTATCAA ATGCAAAGGA    720

AACGTTCAAC CCATTGGTAG CTGCTTTYCC AAGTGTGAAT GTTAGTATGG AAAAGGTGAT    780
```

```
ATTATCACCA AATGAAAATT TATCCAATAG TGTAGAGTCT CATTCATCCA CGAATTGGTC      840

TTATACGAAT ACAGAAGGAG CTTCCATTGA AGCTGGTGGC GGTCCATTAG GCCTTTCTTT      900

TGGAGTGAGT GTTAATTATC AACACTCTGA AACAGTTGCA CAAGAATGGG GAACATCTAC      960

AGGAAATACT TCACAATTCA ATACGGCTTC AGCGGGATAT TTAAATGCCA ATATACGATA     1020

TA                                                                    1022
```

(2) INFORMATION FOR SEQ ID NO:34:

(i) SEQUENCE CHARACTERISTICS:
        (A) LENGTH: 340 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: 177I8

(xi) SEQUENCE DESCRIPTION: SEQ ID NO:34:

```
Gly Leu Ile Gly Tyr Tyr Phe Lys Gly Lys Asp Phe Asn Asn Leu Thr
1               5                   10                  15

Met Phe Ala Pro Thr Arg Asp Asn Thr Leu Met Tyr Asp Gln Gln Thr
            20                  25                  30

Ala Asn Ala Leu Leu Asp Lys Lys Gln Gln Glu Tyr Gln Ser Ile Arg
        35                  40                  45

Trp Ile Gly Leu Ile Gln Ser Lys Glu Thr Gly Asp Phe Thr Phe Asn
50                  55                  60

Leu Ser Lys Asp Glu Gln Ala Ile Ile Glu Ile Asp Gly Lys Ile Ile
65                  70                  75                  80

Ser Asn Lys Gly Lys Glu Lys Gln Val Val His Leu Glu Lys Glu Lys
                85                  90                  95

Leu Val Pro Ile Lys Ile Glu Tyr Gln Ser Asp Thr Lys Phe Asn Ile
            100                 105                 110

Asp Ser Lys Thr Phe Lys Glu Leu Lys Leu Phe Lys Ile Asp Ser Gln
        115                 120                 125

Asn Gln Ser Gln Gln Val Gln Leu Arg Asn Pro Glu Phe Asn Lys Lys
    130                 135                 140

Glu Ser Gln Glu Phe Leu Ala Lys Ala Ser Lys Thr Asn Leu Phe Lys
145                 150                 155                 160

Gln Lys Met Lys Arg Asp Ile Asp Glu Asp Thr Asp Thr Asp Gly Asp
                165                 170                 175

Ser Ile Pro Asp Leu Trp Glu Glu Asn Gly Tyr Thr Ile Gln Asn Lys
            180                 185                 190

Val Ala Val Lys Trp Asp Asp Ser Leu Ala Ser Lys Gly Tyr Thr Lys
        195                 200                 205

Phe Val Ser Asn Pro Leu Asp Ser His Thr Val Gly Asp Pro Tyr Thr
    210                 215                 220

Asp Tyr Glu Lys Ala Ala Arg Asp Leu Asp Leu Ser Asn Ala Lys Glu
225                 230                 235                 240

Thr Phe Asn Pro Leu Val Ala Ala Xaa Pro Ser Val Asn Val Ser Met
                245                 250                 255

Glu Lys Val Ile Leu Ser Pro Asn Glu Asn Leu Ser Asn Ser Val Glu
            260                 265                 270

Ser His Ser Ser Thr Asn Trp Ser Tyr Thr Asn Thr Glu Gly Ala Ser
```

```
                  275                 280                 285
Ile Glu Ala Gly Gly Gly Pro Leu Gly Leu Ser Phe Gly Val Ser Val
        290                 295                 300

Asn Tyr Gln His Ser Glu Thr Val Ala Gln Glu Trp Gly Thr Ser Thr
305                 310                 315                 320

Gly Asn Thr Ser Gln Phe Asn Thr Ala Ser Ala Gly Tyr Leu Asn Ala
                325                 330                 335

Asn Ile Arg Tyr
            340
```

(2) INFORMATION FOR SEQ ID NO:35:

(i) SEQUENCE CHARACTERISTICS:
        (A) LENGTH: 1073 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 185AA2

(xi) SEQUENCE DESCRIPTION: SEQ ID NO:35:

```
TGGATTAATT GGGTATTATT TCCAGGAGCA AAACTTTGAG AAACCCGCTT TGATAGCAAA      60

TAGACAAGCT TCTGATTTGG AAATACCGAA AGATGACGTG AAAGAGTTAC TATCCAAAGA     120

ACAGCAACAC ATTCAATCTG TTAGATGGCT TGGCTATATT CAGCCACCTC AAACAGGAGA     180

CTATGTATTG TCAACCTCAT CCGACCAACA GGTCGTGATT GAACTCGATG GAAAAACCAT     240

TGTCAATCAA ACTTCTATGA CAGAACCGAT TCAACTAGAA AAAGATAAAC GCTATAAAAT     300

TAGAATTGAA TATGTCCCAG GAGATACACA AGGACAAGAG AACCTTCTGG ACTTTCAACT     360

GAAGTGGTCA ATTTCAGGAG CCGAGATAGA ACCAATTCCG GATCATGCTT TCCATTTACC     420

AGATTTTTCT CATAAACAAG ATCAAGAGAA AATCATCCCT GAAACCAATT TATTTCAGAA     480

ACAAGGAGAT GAGAAAAAAG TATCACGCAG TAAGAGATCT TCAGATAAAG ATCCTGACCG     540

TGATACAGAT GATGATAGTA TTTCTGATGA ATGGGAAACG AGTGGATATA CCATTCAAAG     600

ACAGGTGGCA GTGAAATGGG ACGATTCTAT GAAGGAGCTA GGTTATACCA AGTATGTGTC     660

TAACCCTTAT AAGTCTCGTA CAGTAGGAGA TCCATACACA GATTGGGAAA AAGCGGCTGG     720

CAGTATCGAT AATGCTGTCA AAGCAGAAGC CAGAAATCCT TTAGTCGCGG CCTATCCAAC     780

TGTTGGTGTA CATATGGAAA GATTAATTGT CTCCGAACAA CAAAATATAT CAACAGGGCT     840

TGGAAAAACC GTATCTGCGT CTACGTCCGC AAGCAATACC GCAGCGATTA CGGCAGGTAT     900

TGATGCAACA GCTGGTGCCT CTTTACTTGG GCCATCTGGA AGTGTCACGG CTCATTTTTC     960

TTACACGGGA TCTAGTACAG CCACCATTGA AGATAGCTCC AGCCGTAATT GGAGTCGAGA    1020

CCTTGGGATT GATACGGGAC AAGCTGCATA TTTAAATGCC AATATACGAT ATA          1073
```

(2) INFORMATION FOR SEQ ID NO:36:

(i) SEQUENCE CHARACTERISTICS:
        (A) LENGTH: 357 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: 185AA2

(xi) SEQUENCE DESCRIPTION: SEQ ID NO:36:

```
Gly Leu Ile Gly Tyr Tyr Phe Gln Glu Gln Asn Phe Glu Lys Pro Ala
1               5                   10                  15

Leu Ile Ala Asn Arg Gln Ala Ser Asp Leu Glu Ile Pro Lys Asp Asp
                20                  25                  30

Val Lys Glu Leu Leu Ser Lys Gln Gln His Ile Gln Ser Val Arg
        35                  40                  45

Trp Leu Gly Tyr Ile Gln Pro Pro Gln Thr Gly Asp Tyr Val Leu Ser
        50                  55                  60

Thr Ser Ser Asp Gln Gln Val Val Ile Glu Leu Asp Gly Lys Thr Ile
65                  70                  75                  80

Val Asn Gln Thr Ser Met Thr Glu Pro Ile Gln Leu Glu Lys Asp Lys
                85                  90                  95

Arg Tyr Lys Ile Arg Ile Glu Tyr Val Pro Gly Asp Thr Gln Gly Gln
                100                 105                 110

Glu Asn Leu Leu Asp Phe Gln Leu Lys Trp Ser Ile Ser Gly Ala Glu
            115                 120                 125

Ile Glu Pro Ile Pro Asp His Ala Phe His Leu Pro Asp Phe Ser His
        130                 135                 140

Lys Gln Asp Gln Glu Lys Ile Ile Pro Glu Thr Asn Leu Phe Gln Lys
145                 150                 155                 160

Gln Gly Asp Glu Lys Lys Val Ser Arg Ser Lys Arg Ser Ser Asp Lys
                165                 170                 175

Asp Pro Asp Arg Asp Thr Asp Asp Ser Ile Ser Asp Glu Trp Glu
            180                 185                 190

Thr Ser Gly Tyr Thr Ile Gln Arg Gln Val Ala Val Lys Trp Asp Asp
        195                 200                 205

Ser Met Lys Glu Leu Gly Tyr Thr Lys Tyr Val Ser Asn Pro Tyr Lys
        210                 215                 220

Ser Arg Thr Val Gly Asp Pro Tyr Thr Asp Trp Glu Lys Ala Ala Gly
225                 230                 235                 240

Ser Ile Asp Asn Ala Val Lys Ala Glu Ala Arg Asn Pro Leu Val Ala
                245                 250                 255

Ala Tyr Pro Thr Val Gly Val His Met Glu Arg Leu Ile Val Ser Glu
            260                 265                 270

Gln Gln Asn Ile Ser Thr Gly Leu Gly Lys Thr Val Ser Ala Ser Thr
        275                 280                 285

Ser Ala Ser Asn Thr Ala Ala Ile Thr Ala Gly Ile Asp Ala Thr Ala
        290                 295                 300

Gly Ala Ser Leu Leu Gly Pro Ser Gly Ser Val Thr Ala His Phe Ser
305                 310                 315                 320

Tyr Thr Gly Ser Ser Thr Ala Ser Thr Ile Glu Asp Ser Ser Arg Asn
                325                 330                 335

Trp Ser Arg Asp Leu Gly Ile Asp Thr Gly Gln Ala Ala Tyr Leu Asn
                340                 345                 350

Ala Asn Ile Arg Tyr
            355
```

(2) INFORMATION FOR SEQ ID NO:37:

(i) SEQUENCE CHARACTERISTICS:
        (A) LENGTH: 1073 base pairs
        (B) TYPE: nucleic acid
        (C) STRANDEDNESS: single (D) TOPOLOGY: linear (ii) MOLECULE TYPE: DNA (genomic)

(vi) ORIGINAL SOURCE:
         (C) INDIVIDUAL ISOLATE: 196F3

(xi) SEQUENCE DESCRIPTION: SEQ ID NO:37:

```
TGGGTTACNT GGGTATTAYT TTCAGGATAC TAAATTTCAA CAACTTGCTT TAATGGCACA      60

TAGACAAGCC TCAGATTTAG AAATAAACAA AAATGAMGTC AAGGATTTAC TATCAAAGGA     120

TCAACAACAC ATTCAAGCAG TGAGATGGAT GGGCTATATT CAGCCACCTC AAACAGGAGA     180

TTATGTATTG TCAACTTCAT CCGACCAACA GGTCTTCACC GAACTCNATG GAAAAATAAT     240

TCTCAATCAA TCTTCTATGA CCGAACCCAT TCGATTAGAA AAAGATAAAC AATATAMAAT     300

TAGAATTGAA TATGTATCAK AAAGTAAAAC AGAAAAAGAG ACGCTCCTAG ACTTTCAACT     360

CAACTGGTCG ATTTCAGGTG CTACGGTAGA ACCAATTCCA GATAATGCTT TTCAGTTACC     420

AGATCTTTCT CGGGAACAAG NTAAAGATAA AATCATCCCT GAAACAAGTT TATTGCAGGA     480

TCAAGGAGAA GGGAAACAAG TATCTCGAAG TAAAAGATCT CTAGCTGTGA ATCCTCTACA     540

CGATACAGAT GATGATGGGA TTTACGATGA ATGGGAAACA AGCGGCTATA CGATTCAAAG     600

ACAATTGGCA GTAAGATGGA ACGATTCTAT GAAGGATCAA GGCTATACCA AATATGTGTC     660

TAATCCTTAT AAGTCTCATA CTGTAGGAGA TCCATACACA GACTGGGAAA AAGCAGCTGG     720

ACGTATCGAC CAAGCTGTGA AAATAGAAGC CAGAAACCCA TTAGTTGCAG CATATCCAAC     780

AGTTGGCGTA CATATGGAAA GACTGATTGT CTCTGAAAAA CAAAATATAG CAACAGGACT     840

GGGAAAAACA GTATCTGCGT CTACATCTGC AAGTAATACA GCGGGGATTA CAGCGGGAAT     900

CGATGCAACG GTTGGTGCCT CTTTACTTGG ACCTTCGGGA AGTGTCACCG CCCATTTTTC     960

TTATACGGGT TCGAGTACAT CCACTGTTGA AAATAGCTCG AGTAATAATT GGAGTCAAGA    1020

TCTTGGTATT GATACCAGCC AATCTGCGTA CTTAAATGCC AATGTAAGAT ATA          1073
```

(2) INFORMATION FOR SEQ ID NO:38:

(i) SEQUENCE CHARACTERISTICS:
         (A) LENGTH: 357 amino acids
         (B) TYPE: amino acid
         (C) STRANDEDNESS: single
         (D) TOPOLOGY: linear (ii) MOLECULE TYPE: peptide (vi) ORIGINAL SOURCE:
         (C) INDIVIDUAL ISOLATE: 196F3

(xi) SEQUENCE DESCRIPTION: SEQ ID NO:38:

```
Gly Leu Xaa Gly Tyr Xaa Phe Gln Asp Thr Lys Phe Gln Gln Leu Ala
1               5                  10                  15

Leu Met Ala His Arg Gln Ala Ser Asp Leu Glu Ile Asn Lys Asn Xaa
                20                  25                  30

Val Lys Asp Leu Leu Ser Lys Asp Gln Gln His Ile Gln Ala Val Arg
            35                  40                  45

Trp Met Gly Tyr Ile Gln Pro Pro Gln Thr Gly Asp Tyr Val Leu Ser
        50                  55                  60

Thr Ser Ser Asp Gln Gln Val Phe Thr Glu Leu Xaa Gly Lys Ile Ile
65                  70                  75                  80

Leu Asn Gln Ser Ser Met Thr Glu Pro Ile Arg Leu Glu Lys Asp Lys
                85                  90                  95
```

```
Gln Tyr Xaa Ile Arg Ile Glu Tyr Val Ser Xaa Ser Lys Thr Glu Lys
            100                 105                 110

Glu Thr Leu Leu Asp Phe Gln Leu Asn Trp Ser Ile Ser Gly Ala Thr
        115                 120                 125

Val Glu Pro Ile Pro Asp Asn Ala Phe Gln Leu Pro Asp Leu Ser Arg
    130                 135                 140

Glu Gln Xaa Lys Asp Lys Ile Ile Pro Glu Thr Ser Leu Leu Gln Asp
145                 150                 155                 160

Gln Gly Glu Gly Lys Gln Val Ser Arg Ser Lys Arg Ser Leu Ala Val
                165                 170                 175

Asn Pro Leu His Asp Thr Asp Asp Gly Ile Tyr Asp Glu Trp Glu
            180                 185                 190

Thr Ser Gly Tyr Thr Ile Gln Arg Gln Leu Ala Val Arg Trp Asn Asp
        195                 200                 205

Ser Met Lys Asp Gln Gly Tyr Thr Lys Tyr Val Ser Asn Pro Tyr Lys
    210                 215                 220

Ser His Thr Val Gly Asp Pro Tyr Thr Asp Trp Glu Lys Ala Ala Gly
225                 230                 235                 240

Arg Ile Asp Gln Ala Val Lys Ile Glu Ala Arg Asn Pro Leu Val Ala
                245                 250                 255

Ala Tyr Pro Thr Val Gly Val His Met Glu Arg Leu Ile Val Ser Glu
            260                 265                 270

Lys Gln Asn Ile Ala Thr Gly Leu Gly Lys Thr Val Ser Ala Ser Thr
        275                 280                 285

Ser Ala Ser Asn Thr Ala Gly Ile Thr Ala Gly Ile Asp Ala Thr Val
    290                 295                 300

Gly Ala Ser Leu Leu Gly Pro Ser Gly Ser Val Thr Ala His Phe Ser
305                 310                 315                 320

Tyr Thr Gly Ser Ser Thr Ser Ser Val Glu Asn Ser Ser Ser Asn Asn
                325                 330                 335

Trp Ser Gln Asp Leu Gly Ile Asp Thr Ser Gln Ser Ala Tyr Leu Asn
            340                 345                 350

Ala Asn Val Arg Tyr
        355

(2) INFORMATION FOR SEQ ID NO:39:

(i) SEQUENCE CHARACTERISTICS:
        (A) LENGTH: 1073 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (C) INDIVIDUAL ISOLATE: 196J4

(xi) SEQUENCE DESCRIPTION: SEQ ID NO:39:

TGGGTTAATT GGGTATTATT TCCAGGATCA AAAGTTTCAA CAACTTGCTT TAATGGCACA      60

TAGACAAGCT TCTAATTTAA ACATACCAAA AAATGAAGTG AAACAGTTAT TATCCGAAGA    120

TCAACAACAT ATTCAATCCG TTAGGTGGAT CGGATATATC AAATCACCTC AAACGGGAGA    180

TTATATATTG TCAACTTCAG CCGATCGACA TGTCGTAATT GAACTTGACG GAAAAACCAT    240

TCTTAATCAA TCTTCTATGA CAGCACCCAT TCAATTAGAA AAAGATAAAC TTTATAAAAT    300

TAGAATTGAA TATGTCCCAG AAGATACAAA AGGACAGGAA AACCTCTTTG ACTTTCAACT    360
```

```
GAATTGGTCA ATTTCAGGAG ATAAGGTAGA ACCAATTCCG GAGAATGCAT TTCTGTTGCC      420

AGACTTTTCT CATAAACAAG ATCAAGAGAA AATCATCCCT GAAGCAAGTT TATTCCAGGA      480

ACAAGAAGAT GCAAACAAAG TCTCTCGAAA TAAACGATCC ATAGCTACAG GTTCTCTGTA      540

TGATACAGAT GATGATGCTA TTTATGATGA ATGGGAAACA GAAGGATACA CGATACAACG      600

TCAAATAGCG GTGAAATGGG ACGATTCTAT GAAGGAGCGA GGTTATACCA AGTATGTGTC      660

TAACCCCTAT AATTCGCATA CAGTAGGAGA TCCCTACACA GATTGGGAAA AAGCGGCTGG      720

ACGCATTGAT CAGGCAATCA AGTAGAAGC  TAGGAATCCA TTAGTTGCAG CCTATCCAAC      780

AGTTGGTGTA CATATGGAAA AACTGATTGT TTCTGAGAAA CAAAATATAT CAACTGGGGT      840

TGGAAAAACA GTATCTGCGG CTATGTCCAC TGGTAATACC GCAGCGATTA CGGCAGGAAT      900

TGATGCGACC GCCGGGGCAT CTTTACTTGG ACCTTCTGGA AGTGTGACGG CTCATTTTTC      960

TTATACAGGG TCTAGTACAT CTACAATTGA AAATAGTTCA AGCAATAATT GGAGTAAAGA     1020

TCTGGGAATC GATACGGGGC AATCTGCTTA TTTAAATGCC AATGTACGAT ATA           1073
```

(2) INFORMATION FOR SEQ ID NO:40:

(i) SEQUENCE CHARACTERISTICS:
        (A) LENGTH: 357 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: 196J4

(xi) SEQUENCE DESCRIPTION: SEQ ID NO:40:

```
Gly Leu Ile Gly Tyr Tyr Phe Gln Asp Gln Lys Phe Gln Gln Leu Ala
1               5                   10                  15

Leu Met Ala His Arg Gln Ala Ser Asn Leu Asn Ile Pro Lys Asn Glu
                20                  25                  30

Val Lys Gln Leu Leu Ser Glu Asp Gln Gln His Ile Gln Ser Val Arg
            35                  40                  45

Trp Ile Gly Tyr Ile Lys Ser Pro Gln Thr Gly Asp Tyr Ile Leu Ser
        50                  55                  60

Thr Ser Ala Asp Arg His Val Val Ile Glu Leu Asp Gly Lys Thr Ile
65                  70                  75                  80

Leu Asn Gln Ser Ser Met Thr Ala Pro Ile Gln Leu Glu Lys Asp Lys
                85                  90                  95

Leu Tyr Lys Ile Arg Ile Glu Tyr Val Pro Glu Asp Thr Lys Gly Gln
                100                 105                 110

Glu Asn Leu Phe Asp Phe Gln Leu Asn Trp Ser Ile Ser Gly Asp Lys
            115                 120                 125

Val Glu Pro Ile Pro Glu Asn Ala Phe Leu Leu Pro Asp Phe Ser His
        130                 135                 140

Lys Gln Asp Gln Glu Lys Ile Ile Pro Glu Ala Ser Leu Phe Gln Glu
145                 150                 155                 160

Gln Glu Asp Ala Asn Lys Val Ser Arg Asn Lys Arg Ser Ile Ala Thr
                165                 170                 175

Gly Ser Leu Tyr Asp Thr Asp Asp Ala Ile Tyr Asp Glu Trp Glu
                180                 185                 190

Thr Glu Gly Tyr Thr Ile Gln Arg Gln Ile Ala Val Lys Trp Asp Asp
            195                 200                 205
```

```
Ser Met Lys Glu Arg Gly Tyr Thr Lys Tyr Val Ser Asn Pro Tyr Asn
    210                 215                 220

Ser His Thr Val Gly Asp Pro Tyr Thr Asp Trp Glu Lys Ala Ala Gly
225                 230                 235                 240

Arg Ile Asp Gln Ala Ile Lys Val Glu Ala Arg Asn Pro Leu Val Ala
                245                 250                 255

Ala Tyr Pro Thr Val Gly Val His Met Glu Lys Leu Ile Val Ser Glu
            260                 265                 270

Lys Gln Asn Ile Ser Thr Gly Val Gly Lys Thr Val Ser Ala Ala Met
        275                 280                 285

Ser Thr Gly Asn Thr Ala Ala Ile Thr Ala Gly Ile Asp Ala Thr Ala
    290                 295                 300

Gly Ala Ser Leu Leu Gly Pro Ser Gly Ser Val Thr Ala His Phe Ser
305                 310                 315                 320

Tyr Thr Gly Ser Ser Thr Ser Ser Ile Glu Asn Ser Ser Ser Asn Asn
                325                 330                 335

Trp Ser Lys Asp Leu Gly Ile Asp Thr Gly Gln Ser Ala Tyr Leu Asn
            340                 345                 350

Ala Asn Val Arg Tyr
        355

(2) INFORMATION FOR SEQ ID NO:41:

(i) SEQUENCE CHARACTERISTICS:
        (A) LENGTH: 1046 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 197T1

(xi) SEQUENCE DESCRIPTION: SEQ ID NO:41:

TGGATTAATT GGGTATTATT TTAAAGGAAA AGATTTTAAT AATCTTACTA TATTTGCTCC      60

AACACGTGAG AATACTCTTA TTTATGATTT AGAAACAGCG AATTCTTTAT TAGATAAGCA    120

ACAACAAACC TATCAATCTA TTCGTTGGAT CGGTTTAATA AAAAGCAAAA AAGCTGGAGA    180

TTTTACCTTT CAATTATCGG ATGATGAGCA TGCTATTATA GAAATCGATG GGAAAGTTAT    240

TTCGCAAAAA GGCCAAAAGA AACAAGTTGT TCATTTAGAA AAAGATAAAT TAGTTCCCAT    300

CAAAATTGAA TATCAATCTG ATAAAGCGTT AAACCCAGAC AGTCAAATGT TTAAAGAATT    360

GAATTATTT AAAATAAATA GTCAAAAACA ATCTCAGCAA GTGCAACAAG ACGAATTGAG    420

AAATCCTGAA TTTGGTAAAG AAAAAACTCA AACATATTTA AAGAAAGCAT CGAAAAGCAG    480

CTTGTTTAGC AATAAAAGTA AACGAGATAT AGATGAAGAT ATAGATGAGG ATACAGATAC    540

AGATGGAGAT GCCATTCCTG ATGTATGGGA AGAAATGGG TATACCATCA AAGGAAGAGT    600

AGCTGTTAAA TGGGACGAAG GATTAGCTGA TAAGGGATAT AAAAAGTTTG TTTCCAATCC    660

TTTTAGACAG CACACTGCTG GTGACCCCTA TAGTGACTAT GAAAAGGCAT CAAAAGATTT    720

GGATTTATCT AATGCAAAAG AAACATTTAA TCCATTGGTG GCTGCTTTTC CAAGTGTCAA    780

TGTTAGCTTG GAAAATGTCA CCATATCAAA AGATGAAAAT AAAACTGCTG AAATTGCGTC    840

TACTTCATCG AATAATTGGT CCTATACAAA TACAGAGGGG GCATCTATTG AAGCTGGAAT    900

TGGACCAGAA GGTTTGTTGT CTTTTGGAGT AAGTGCCAAT TATCAACATT CTGAAACAGT    960

GGCCAAAGAG TGGGGTACAA CTAAGGGAGA CGCAACACAA TATAATACAG CTTCAGCAGG   1020
```

ATATCTAAAT GCCAATGTAC GATATA                                                          1046

(2) INFORMATION FOR SEQ ID NO:42:

(i) SEQUENCE CHARACTERISTICS:
        (A) LENGTH: 348 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: 197T1

(xi) SEQUENCE DESCRIPTION: SEQ ID NO:42:

```
Gly Leu Ile Gly Tyr Tyr Phe Lys Gly Lys Asp Phe Asn Asn Leu Thr
 1               5                  10                  15

Ile Phe Ala Pro Thr Arg Glu Asn Thr Leu Ile Tyr Asp Leu Glu Thr
             20                  25                  30

Ala Asn Ser Leu Leu Asp Lys Gln Gln Gln Thr Tyr Gln Ser Ile Arg
         35                  40                  45

Trp Ile Gly Leu Ile Lys Ser Lys Lys Ala Gly Asp Phe Thr Phe Gln
 50                  55                  60

Leu Ser Asp Asp Glu His Ala Ile Ile Glu Ile Asp Gly Lys Val Ile
 65                  70                  75                  80

Ser Gln Lys Gly Gln Lys Gln Val Val His Leu Glu Lys Asp Lys
                 85                  90                  95

Leu Val Pro Ile Lys Ile Glu Tyr Gln Ser Asp Lys Ala Leu Asn Pro
                100                 105                 110

Asp Ser Gln Met Phe Lys Glu Leu Lys Leu Phe Lys Ile Asn Ser Gln
            115                 120                 125

Lys Gln Ser Gln Gln Val Gln Gln Asp Glu Leu Arg Asn Pro Glu Phe
130                 135                 140

Gly Lys Glu Lys Thr Gln Thr Tyr Leu Lys Lys Ala Ser Lys Ser Ser
145                 150                 155                 160

Leu Phe Ser Asn Lys Ser Lys Arg Asp Ile Asp Glu Asp Ile Asp Glu
                165                 170                 175

Asp Thr Asp Thr Asp Gly Asp Ala Ile Pro Asp Val Trp Glu Glu Asn
            180                 185                 190

Gly Tyr Thr Ile Lys Gly Arg Val Ala Val Lys Trp Asp Glu Gly Leu
        195                 200                 205

Ala Asp Lys Gly Tyr Lys Lys Phe Val Ser Asn Pro Phe Arg Gln His
    210                 215                 220

Thr Ala Gly Asp Pro Tyr Ser Asp Tyr Glu Lys Ala Ser Lys Asp Leu
225                 230                 235                 240

Asp Leu Ser Asn Ala Lys Glu Thr Phe Asn Pro Leu Val Ala Ala Phe
                245                 250                 255

Pro Ser Val Asn Val Ser Leu Glu Asn Val Thr Ile Ser Lys Asp Glu
            260                 265                 270

Asn Lys Thr Ala Glu Ile Ala Ser Thr Ser Ser Asn Asn Trp Ser Tyr
        275                 280                 285

Thr Asn Thr Glu Gly Ala Ser Ile Glu Ala Gly Ile Gly Pro Glu Gly
    290                 295                 300

Leu Leu Ser Phe Gly Val Ser Ala Asn Tyr Gln His Ser Glu Thr Val
305                 310                 315                 320
```

Ala Lys Glu Trp Gly Thr Thr Lys Gly Asp Ala Thr Gln Tyr Asn Thr
            325                 330                 335

Ala Ser Ala Gly Tyr Leu Asn Ala Asn Val Arg Tyr
            340                 345

(2) INFORMATION FOR SEQ ID NO:43:

(i) SEQUENCE CHARACTERISTICS:
        (A) LENGTH: 1002 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 197U2

(xi) SEQUENCE DESCRIPTION: SEQ ID NO:43:

TGGGTTAATT GGGTATTATT TTACGGATGA GCAGCATAAG GAAGTAGCTT TTAYTCAATT    60

AGGTGAAAAA AMTACATTAG CAGATTCAGC GAAAATGAAG AAAAACGACA AAAAGATTCT   120

TTCAGCGCAA TGGATTGGWA ATATACAGGT ACCTCAAACA GGGGAATATA CGTTTTCCAC   180

CTCTTCTGAT AAAGATACTA TTTTAAAACT CAATGGGGAA ACGATTATTC AAAAATCTAA   240

TATGGAGAAA CCCATATATT TAGAAAAAGA TAAAGTATAC GAAATTCAAA TCGAGCATAA   300

CAACCCGAAT AGTGAGAAAA CTTTACGATT ATCTTGGAAA ATGGGGGGCA CCAATTCAGA   360

GCTCATCCCA GAAAAATACA TTCTGTCTCC CGATTTTTCT AAAATAGCAG ATCAAGAAAA   420

TGARAAAAAA GACGCATCGA GACATTTATT ATTTACTAAG GATGAATTGA AAGATTCTGA   480

TAAGGACCTT ATCCCAGATG AATTTGAAAA AAATGGGTAT ACATTCAATG GGATTCAAAT   540

TGTTCCTTGG GATGAATCTC TTCAAGAACA GGGCTTTAAA AAATATATTT CCAATCCATA   600

TCAATCGCGT ACAGCGCAGG ATCCATATAC AGATTTTGAA AAAGTAACCG GATATATGCC   660

TGCCGAAACA CAACTGGAAA CGCGTGACCC TTTAGTTGCG GCTTATCCGG CTGTAGGGGT   720

TACGATGGAA CAGTTTATTT TCTCTAAAAA TGATAATGTG CAGGAATCTA ATGGTGGAGG   780

AACTTCAAAA AGTATGACAG AAAGTTCTGA AACGACTTAC TCTGTTGAGA TAGGAGGGAA   840

ATTTACATTG AATCCATTCG CACTGGCGGA AATTTCTCCT AAATATTCTC ACAGTTGGAA   900

AAATGGAGCA TCTACAACAG AGGGAGAAAG TACTTCCTGG AGCTCACAAA TTGGTATTAA   960

CACGGCTGAA CGCGCGTTTT TTAAATGCCA ATATTCGATA TA                    1002

(2) INFORMATION FOR SEQ ID NO:44:

(i) SEQUENCE CHARACTERISTICS:
        (A) LENGTH: 333 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: 197U2

(xi) SEQUENCE DESCRIPTION: SEQ ID NO:44:

Gly Leu Ile Gly Tyr Tyr Phe Thr Asp Glu Gln His Lys Glu Val Ala
1               5                   10                  15

Phe Xaa Gln Leu Gly Glu Lys Xaa Thr Leu Ala Asp Ser Ala Lys Met
            20                  25                  30

Lys Lys Asn Asp Lys Lys Ile Leu Ser Ala Gln Trp Ile Xaa Asn Ile

|   |   |   |   |   | 35 |   |   |   | 40 |   |   |   |   | 45 |   |
|---|---|---|---|---|---|---|---|---|---|---|---|---|---|---|---|

Gln Val Pro Gln Thr Gly Glu Tyr Thr Phe Ser Thr Ser Ser Asp Lys
 50                      55                      60

Asp Thr Ile Leu Lys Leu Asn Gly Glu Thr Ile Ile Gln Lys Ser Asn
65                       70                      75                       80

Met Glu Lys Pro Ile Tyr Leu Glu Lys Asp Lys Val Tyr Glu Ile Gln
                 85                      90                       95

Ile Glu His Asn Asn Pro Asn Ser Glu Lys Thr Leu Arg Leu Ser Trp
                 100                     105                     110

Lys Met Gly Gly Thr Asn Ser Glu Leu Ile Pro Glu Lys Tyr Ile Leu
                 115                     120                     125

Ser Pro Asp Phe Ser Lys Ile Ala Asp Gln Glu Asn Xaa Lys Lys Asp
130                     135                     140

Ala Ser Arg His Leu Leu Phe Thr Lys Asp Glu Leu Lys Asp Ser Asp
145                     150                     155                     160

Lys Asp Leu Ile Pro Asp Glu Phe Glu Lys Asn Gly Tyr Thr Phe Asn
                 165                     170                     175

Gly Ile Gln Ile Val Pro Trp Asp Glu Ser Leu Gln Glu Gln Gly Phe
                 180                     185                     190

Lys Lys Tyr Ile Ser Asn Pro Tyr Gln Ser Arg Thr Ala Gln Asp Pro
                 195                     200                     205

Tyr Thr Asp Phe Glu Lys Val Thr Gly Tyr Met Pro Ala Glu Thr Gln
210                     215                     220

Leu Glu Thr Arg Asp Pro Leu Val Ala Ala Tyr Pro Ala Val Gly Val
225                     230                     235                     240

Thr Met Glu Gln Phe Ile Phe Ser Lys Asn Asp Asn Val Gln Glu Ser
                 245                     250                     255

Asn Gly Gly Gly Thr Ser Lys Ser Met Thr Glu Ser Ser Glu Thr Thr
                 260                     265                     270

Tyr Ser Val Glu Ile Gly Gly Lys Phe Thr Leu Asn Pro Phe Ala Leu
                 275                     280                     285

Ala Glu Ile Ser Pro Lys Tyr Ser His Ser Trp Lys Asn Gly Ala Ser
                 290                     295                     300

Thr Thr Glu Gly Glu Ser Thr Ser Trp Ser Ser Gln Ile Gly Ile Asn
305                     310                     315                     320

Thr Ala Glu Arg Ala Phe Phe Lys Cys Gln Tyr Ser Ile
                 325                     330

(2) INFORMATION FOR SEQ ID NO:45:

(i) SEQUENCE CHARACTERISTICS:
        (A) LENGTH: 1073 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 202E1

(xi) SEQUENCE DESCRIPTION: SEQ ID NO:45:

```
TGGGTTAATT GGGTACTATT TTCAGGATCA AAAGTTTCAA CAACTCGCTT TGATGGCACA    60

TAGACAAGCT TCAGATTTAG AAATACCTAA AAATGAAGTG AAGGATATAT TATCTAAAGA   120

TCAACAACAT ATTCAATCAG TGAGATGGAG GGGGTATATT AAGCCACCTC AAACAGGAGA   180

CTATATATTG TCAACCTCAT CCGACCAACA GGTCGTGATT GAACTCGATG GAAAAAACAT   240
```

```
TGTCAATCAA ACTTCTATGA CAGAACCAAT TCAACTCGAA AAAGATAAAC TCTATAAAAT      300

TAGAATTGAA TATGTCCCAG GAGATACAAA AGGACAAGAG AGCCTCCTTG ACTTTCAACT      360

TAACTGGTCA ATTTCAGGAG ATACGGTGGA ACCAATTCCG GAGAATGCAT TTCTGTTACC      420

AGACTTTTCT CATCAACAAG ATCAAGAGAA ACTCATCCCT GAAATCAGTC TATTTCAGGA      480

ACAAGGAGAT GAGAAAAAAG TATCTCGTAG TAAGAGGTCT TTAGCTACAA ACCCTCTCCT      540

TGATACAGAT GATGATGGTA TTTATGATGA ATGGGAAACG GAAGGATACA CAATACAGGG      600

ACAACTAGCG GTGAAATGGG ACGATTCTAT GAAGGAGCGA GGTTATACTA AGTATGTGTC      660

TAACCCTTAC AAGGCTCATA CAGTAGGAGA TCCCTACACA GATTGGGAAA AAGCGGCTGG      720

CCGTATCGAT AACGCTGTCA AAGCAGAAGC TAGGAATCCT TTAGTCGCGG CCTATCCAAC      780

TGTTGGTGTA CATATGGAAA GACTAATTGT CTCCGAAAAA CAAAATATAT CAACAGGACT      840

TGGAAAAACC GTATCTGTGT CTATGTCCGC AAGCAATACC GCAGCGATTA CGGCAGGAAT      900

TAATGCAACA GCCGGTGCCT CTTTACTTGG GCCATCTGGA AACGTCACGG CTCATTTTTC      960

TTATACAGGA TCTAGTACAT CCACTGTTGA AAATAGCTCA AGTAATAATT GGAGTCAAGA     1020

TCTTGGAATC GATACGGGAC AATCTGCGTA TTTAAATGCC AATGTAAGAT ATA           1073
```

(2) INFORMATION FOR SEQ ID NO:46:

(i) SEQUENCE CHARACTERISTICS:
        (A) LENGTH: 357 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: 202E1

(xi) SEQUENCE DESCRIPTION: SEQ ID NO:46:

```
Gly Leu Ile Gly Tyr Tyr Phe Gln Asp Gln Lys Phe Gln Gln Leu Ala
1               5                   10                  15

Leu Met Ala His Arg Gln Ala Ser Asp Leu Glu Ile Pro Lys Asn Glu
            20                  25                  30

Val Lys Asp Ile Leu Ser Lys Asp Gln Gln His Ile Gln Ser Val Arg
        35                  40                  45

Trp Arg Gly Tyr Ile Lys Pro Pro Gln Thr Gly Asp Tyr Ile Leu Ser
    50                  55                  60

Thr Ser Asp Gln Gln Val Val Ile Glu Leu Asp Gly Lys Asn Ile
65                  70                  75                  80

Val Asn Gln Thr Ser Met Thr Glu Pro Ile Gln Leu Glu Lys Asp Lys
                85                  90                  95

Leu Tyr Lys Ile Arg Ile Glu Tyr Val Pro Gly Asp Thr Lys Gly Gln
            100                 105                 110

Glu Ser Leu Leu Asp Phe Gln Leu Asn Trp Ser Ile Ser Gly Asp Thr
        115                 120                 125

Val Glu Pro Ile Pro Glu Asn Ala Phe Leu Leu Pro Asp Phe Ser His
    130                 135                 140

Gln Gln Asp Gln Glu Lys Leu Ile Pro Glu Ile Ser Leu Phe Gln Glu
145                 150                 155                 160

Gln Gly Asp Glu Lys Lys Val Ser Arg Ser Lys Arg Ser Leu Ala Thr
                165                 170                 175

Asn Pro Leu Leu Asp Thr Asp Asp Asp Gly Ile Tyr Asp Glu Trp Glu
```

```
                 180                 185                 190
Thr Glu Gly Tyr Thr Ile Gln Gly Gln Leu Ala Val Lys Trp Asp Asp
        195                 200                 205

Ser Met Lys Glu Arg Gly Tyr Thr Lys Tyr Val Ser Asn Pro Tyr Lys
    210                 215                 220

Ala His Thr Val Gly Asp Pro Tyr Thr Asp Trp Glu Lys Ala Ala Gly
225                 230                 235                 240

Arg Ile Asp Asn Ala Val Lys Ala Glu Ala Arg Asn Pro Leu Val Ala
                245                 250                 255

Ala Tyr Pro Thr Val Gly Val His Met Glu Arg Leu Ile Val Ser Glu
            260                 265                 270

Lys Gln Asn Ile Ser Thr Gly Leu Gly Lys Thr Val Ser Val Ser Met
        275                 280                 285

Ser Ala Ser Asn Thr Ala Ala Ile Thr Ala Gly Ile Asn Ala Thr Ala
    290                 295                 300

Gly Ala Ser Leu Leu Gly Pro Ser Gly Asn Val Thr Ala His Phe Ser
305                 310                 315                 320

Tyr Thr Gly Ser Ser Thr Ser Thr Val Glu Asn Ser Ser Ser Asn Asn
                325                 330                 335

Trp Ser Gln Asp Leu Gly Ile Asp Thr Gly Gln Ser Ala Tyr Leu Asn
            340                 345                 350

Ala Asn Val Arg Tyr
        355
```

(2) INFORMATION FOR SEQ ID NO:47:

(i) SEQUENCE CHARACTERISTICS:
        (A) LENGTH: 967 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: KB33

(xi) SEQUENCE DESCRIPTION: SEQ ID NO:47:

```
TGGATTACTT GGGTACTATT TTGAAGAACC AAACTTTAAT GACCTTCTAT TAATCACACA    60

AAAAAACAAC AGTAATTTAT CTCTAGAAAA AGAACATATT TCATCGTTAT CTAGTATTAG   120

AAATAAAGGC ATTCAATCTG CTAGATGGTT AGGTTTTTTA AAACCAAAGC AAACGGATGA   180

ATATGTTTTT TTTAGTCCTT CCAACCATGA AATCATGATT CAAATCGATA ACAAAATTAT   240

TGTAATGGGT AGAAAAATTA TGTTAGAAGA AGGAAAGGTA TATCCAATTC GAATTGAATG   300

CCGCTTTGAA AAAACAAATA ATCTAGATAT AAACTGCGAA CTACTTTGGA CGCATTCTGA   360

TACAAAAGAA ATCATTTCTC AAAACTGTTT GCTGGCACCT GATTATCATA ATACAGAATT   420

TTACCCAAAA ACAAATTTAT TTGGGGATGT ATCTACTACG ACTAGTGATA CTGATAATGA   480

TGGAATACCA GATGACTGGG AAATTAATGG TTATACGTTT GATGGTACAA ATATAATTCA   540

ATGGAATCCT GCTTATGAAG GGTTATATAC TAAATATATT TCTAACCCTA ACAAGCAAG   600

TACAGTAGGT GATCCATATA CAGATTTAGA GAACGTMCAA AGCTAAAKGG ATCAAAGAAS   660

CARGAAAYCC TTKTAGCAGA AGCTWATCCG AAAAATTGGA BTTAGCATGG AAGAATTACT   720

CRTCTCTKTA WAARTGKTGA TKTWTTCAAA TGCTCAAGAA AATKACTACT TACTTCTAGT   780

AGRACAGAAG GCACTTCASG TAGYGCAGGC ATTGAGGGAG GAGCAGAAGG AAAAAAACCT   840
```

```
ACAGGATTGG TTTCAGCCTC CTTTTCGCAT TCATCTTCAA CAACAAACAC AACGGAACAA      900

ATGAATGGAA CAATGATTCA TCTTGATACA GGAGAATCAG CGTATTTAAA TGCCAATGTA      960

AGATATA                                                                967
```

(2) INFORMATION FOR SEQ ID NO:48:

(i) SEQUENCE CHARACTERISTICS:
        (A) LENGTH: 972 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: KB38

(xi) SEQUENCE DESCRIPTION: SEQ ID NO:48:

```
TGGATTACTT GGGTATTATT TTGAAGAACC AAACTTTAAT AACCTTCTAT TAATCACACA       60

AAAAAACAAC AGTAATTTAT CTCTAGAAAA AGAACATATT TCATCGTTAT CTAGTATTAG      120

AAATAAAGGC ATTCAATCTG CTAGATGGTT AGGTTTTTTA AAACCAGAGC AAACGGATGA      180

ATATGTTTTT TTTAGTCCTT CCAACCATGA AATTATGATT CAAATCGATA ACAAAATTAT      240

TGTAATGGGT AGAAAAATTA TGTTAGAAAA AGGAAAGGTA TATCCAATTC GAATTGAATG      300

CCGCTTTGAA AAAACAAATA ATATAGATAT AAACTGCGAA CTACTTTGGA CGCACTCTGA      360

TACAAAAGAA ATCATTTCTC AAAACTTTTT GCTGGCACCT GATTATAACA ATACAGAATT      420

TTATCCAAAA ACAAATTTAT TTGGAGATGT ATCTACTACG ACTWAGTGAT ACTGATAATG      480

ATGGAATACC AGATGACTGG GAAATTAATG GTTATACCTT TGATGGTACA AATATAATTC      540

AGTGGAATTC TGCTTATGAA GGGTTATATA CTAAATATGT TTCTAATCCT AAACAAGCAA      600

GTACAGTAGG TGATCCATAT ACAGATTTAG AGAAAGTAAC AGCTCAAATG GATCGAGCAA      660

CCTCTCTAGA AGCAAGGAAT CCTTTAGTAG CAGCTTATCC AAAAATTGGA GTTAGCATGG      720

AAGAATTACT CATCTCTTTA AATGTTGATT TTTCAAATGC TCAAGAAAAT ACTACTTCTT      780

CTAGTAGAAC AGAAGGCACT TCACGTAGCG CAGGCATTGA GGGAGGAGCA GAAGGAAAAA      840

AACCTACAGG ATTGGTTTCA GCCTCCTTTT CGCATTCATC TTCAACAACA ACACAACGG       900

AACAAATGAA TGGAACAATG ATTCATCTTG ATACAGGAGA ATCAGCGTAT TTAAATGCCA      960

ATGTAAGATA TA                                                          972
```

(2) INFORMATION FOR SEQ ID NO:49:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

```
CTTGAYTTTA AARATGATRT A                                                 21
```

(2) INFORMATION FOR SEQ ID NO:50:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

AATRGCSWAT AAATAMGCAC C                                              21

(2) INFORMATION FOR SEQ ID NO:51:

(i) SEQUENCE CHARACTERISTICS:
             (A) LENGTH: 1341 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (C) INDIVIDUAL ISOLATE: 177C8

(xi) SEQUENCE DESCRIPTION: SEQ ID NO:51:

ATGTTTATGG TTTCTAAAAA ATTACAAGTA GTTACTAAAA CTGTATTGCT TAGTACAGTT      60

TTCTCTATAT CTTTATTAAA TAATGAAGTG ATAAAAGCTG AACAATTAAA TATAAATTCT     120

CAAAGTAAAT ATACTAACTT GCAAAATCTA AAAATCACTG ACAAGGTAGA GGATTTTAAA     180

GAAGATAAGG AAAAAGCGAA AGAATGGGGG AAAGAAAAAG AAAAAGAGTG GAAACTAACT     240

GCTACTGAAA AAGGAAAAAT GAATAATTTT TTAGATAATA AAAATGATAT AAAGACAAAT     300

TATAAAGAAA TTACTTTTTC TATGGCAGGC TCATTTGAAG ATGAAATAAA AGATTTAAAA     360

GAAATTGATA AGATGTTTGA TAAAACCAAT CTATCAAATT CTATTATCAC CTATAAAAAT     420

GTGGAACCGA CAACAATTGG ATTTAATAAA TCTTTAACAG AAGGTAATAC GATTAATTCT     480

GATGCAATGG CACAGTTTAA AGAACAATTT TTAGATAGGG ATATTAAGTT TGATAGTTAT     540

CTAGATACGC ATTTAACTGC TCAACAAGTT TCCAGTAAAA AAAGAGTTAT TTTGAAGGTT     600

ACGGTTCCGA GTGGGAAAGG TTCTACTACT CCAACAAAAG CAGGTGTCAT TTTAAATAAT     660

AGTGAATACA AAATGCTCAT TGATAATGGG TATATGGTCC ATGTAGATAA GGTATCAAAA     720

GTGGTGAAAA AAGGGGTGGA GTGCTTACAA ATTGAAGGGA CTTTAAAAAA GAGTCTTGAC     780

TTTAAAAATG ATATAAATGC TGAAGCGCAT AGCTGGGGTA TGAAGAATTA TGAAGAGTGG     840

GCTAAAGATT TAACCGATTC GCAAAGGGAA GCTTTAGATG GGTATGCTAG GCAAGATTAT     900

AAAGAAATCA ATAATTATTT AAGAAATCAA GGCGGAAGTG GAAATGAAAA ACTAGATGCT     960

CAAATAAAAA ATATTTCTGA TGCTTTAGGG AAGAAACCAA TACCGGAAAA TATTACTGTG    1020

TATAGATGGT GTGGCATGCC GGAATTTGGT TATCAAATTA GTGATCCGTT ACCTTCTTTA    1080

AAAGATTTTG AAGAACAATT TTTAAATACA ATCAAAGAAG ACAAAGGATA TATGAGTACA    1140

AGCTTATCGA GTGAACGTCT TGCAGCTTTT GGATCTAGAA AAATTATATT ACGATTACAA    1200

GTTCCGAAAG GAAGTACGGG TGCGTATTTA AGTGCCATTG GTGGATTTGC AAGTGAAAAA    1260

GAGATCCTAC TTGATAAAGA TAGTAAATAT CATATTGATA AAGTAACAGA GGTAATTATT    1320

AAGGTGTTAA GCGATATGTA G                                             1341

(2) INFORMATION FOR SEQ ID NO:52:

(i) SEQUENCE CHARACTERISTICS:
             (A) LENGTH: 446 amino acids
             (B) TYPE: amino acid
             (C) STRANDEDNESS: single
             (D) TOPOLOGY: linear (ii) MOLECULE TYPE: peptide (vi) ORIGINAL SOURCE:
    (C) INDIVIDUAL ISOLATE: 177C8

(xi) SEQUENCE DESCRIPTION: SEQ ID NO:52:

```
Met Phe Met Val Ser Lys Lys Leu Gln Val Val Thr Lys Thr Val Leu
 1               5                  10                  15

Leu Ser Thr Val Phe Ser Ile Ser Leu Leu Asn Asn Glu Val Ile Lys
                20                  25                  30

Ala Glu Gln Leu Asn Ile Asn Ser Gln Ser Lys Tyr Thr Asn Leu Gln
            35                  40                  45

Asn Leu Lys Ile Thr Asp Lys Val Glu Asp Phe Lys Glu Asp Lys Glu
        50                  55                  60

Lys Ala Lys Glu Trp Gly Lys Glu Lys Glu Trp Lys Leu Thr
 65                 70                  75                  80

Ala Thr Glu Lys Gly Lys Met Asn Asn Phe Leu Asp Asn Lys Asn Asp
                85                  90                  95

Ile Lys Thr Asn Tyr Lys Glu Ile Thr Phe Ser Met Ala Gly Ser Phe
            100                 105                 110

Glu Asp Glu Ile Lys Asp Leu Lys Glu Ile Asp Lys Met Phe Asp Lys
        115                 120                 125

Thr Asn Leu Ser Asn Ser Ile Ile Thr Tyr Lys Asn Val Glu Pro Thr
    130                 135                 140

Thr Ile Gly Phe Asn Lys Ser Leu Thr Glu Gly Asn Thr Ile Asn Ser
145                 150                 155                 160

Asp Ala Met Ala Gln Phe Lys Glu Gln Phe Leu Asp Arg Asp Ile Lys
                165                 170                 175

Phe Asp Ser Tyr Leu Asp Thr His Leu Thr Ala Gln Gln Val Ser Ser
            180                 185                 190

Lys Glu Arg Val Ile Leu Lys Val Thr Val Pro Ser Gly Lys Gly Ser
        195                 200                 205

Thr Thr Pro Thr Lys Ala Gly Val Ile Leu Asn Asn Ser Glu Tyr Lys
    210                 215                 220

Met Leu Ile Asp Asn Gly Tyr Met Val His Val Asp Lys Val Ser Lys
225                 230                 235                 240

Val Val Lys Lys Gly Val Glu Cys Leu Gln Ile Glu Gly Thr Leu Lys
                245                 250                 255

Lys Ser Leu Asp Phe Lys Asn Asp Ile Asn Ala Glu Ala His Ser Trp
            260                 265                 270

Gly Met Lys Asn Tyr Glu Glu Trp Ala Lys Asp Leu Thr Asp Ser Gln
        275                 280                 285

Arg Glu Ala Leu Asp Gly Tyr Ala Arg Gln Asp Tyr Lys Glu Ile Asn
    290                 295                 300

Asn Tyr Leu Arg Asn Gln Gly Gly Ser Gly Asn Glu Lys Leu Asp Ala
305                 310                 315                 320

Gln Ile Lys Asn Ile Ser Asp Ala Leu Gly Lys Lys Pro Ile Pro Glu
                325                 330                 335

Asn Ile Thr Val Tyr Arg Trp Cys Gly Met Pro Glu Phe Gly Tyr Gln
            340                 345                 350

Ile Ser Asp Pro Leu Pro Ser Leu Lys Asp Phe Glu Gln Phe Leu
        355                 360                 365

Asn Thr Ile Lys Glu Asp Lys Gly Tyr Met Ser Thr Ser Leu Ser Ser
    370                 375                 380

Glu Arg Leu Ala Ala Phe Gly Ser Arg Lys Ile Ile Leu Arg Leu Gln
```

```
385                 390                 395                 400
Val Pro Lys Gly Ser Thr Gly Ala Tyr Leu Ser Ala Ile Gly Gly Phe
                405                 410                 415
Ala Ser Glu Lys Glu Ile Leu Leu Asp Lys Asp Ser Lys Tyr His Ile
                420                 425                 430
Asp Lys Val Thr Glu Val Ile Ile Lys Val Leu Ser Asp Met
                435                 440                 445
```

(2) INFORMATION FOR SEQ ID NO:53:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

GGATTCGTTA TCAGAAA                                                17

(2) INFORMATION FOR SEQ ID NO:54:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

CTGTYGCTAA CAATGTC                                                17

(2) INFORMATION FOR SEQ ID NO:55:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:55:

```
Ala Asp Glu Pro Phe Asn Ala Asp
1               5
```

(2) INFORMATION FOR SEQ ID NO:56:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

GCTGATGAAC CATTTAATGC C                                        21

(2) INFORMATION FOR SEQ ID NO:57:

(i) SEQUENCE CHARACTERISTICS:
        (A) LENGTH: 8 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO:57:

Leu Phe Lys Val Asp Thr Lys Gln
1               5

(2) INFORMATION FOR SEQ ID NO:58:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

CTCTTTAAAG TAGATACTAA GC                                              22

(2) INFORMATION FOR SEQ ID NO:59:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:59:

Pro Asp Glu Asn Leu Ser Asn Ile Glu
1               5

(2) INFORMATION FOR SEQ ID NO:60:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

GATGAGAACT TATCAAATAG TATC                                            24

(2) INFORMATION FOR SEQ ID NO:61:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:61:

Ala Asn Ser Leu Leu Asp Lys Gln Gln Gln Thr Tyr
1               5                   10

(2) INFORMATION FOR SEQ ID NO:62:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

CGAATTCTTT ATTAGATAAG CAACAACAAA CCT                             33

(2) INFORMATION FOR SEQ ID NO:63:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:63:

Val Ile Ser Gln Lys Gly Gln Lys
1               5

(2) INFORMATION FOR SEQ ID NO:64:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:64:

GTTATTTCGC AAAAAGGCCA AAAG                                       24

(2) INFORMATION FOR SEQ ID NO:65:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:65:

Glu Tyr Gln Ser Asp Lys Ala Leu Asn Pro Asp
1               5                   10

(2) INFORMATION FOR SEQ ID NO:66:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:66:

GAATATCAAT CTGATAAAGC GTTAAACCCA G                               31

(2) INFORMATION FOR SEQ ID NO:67:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide

```
    (xi) SEQUENCE DESCRIPTION: SEQ ID NO:67:

Ser Ser Leu Phe Ser Asn Lys Ser Lys
1               5

(2) INFORMATION FOR SEQ ID NO:68:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:68:

GCAGCYTGTT TAGCAATAAA AGT                                              23

(2) INFORMATION FOR SEQ ID NO:69:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:69:

Ile Lys Gly Arg Val Ala Val Lys
1               5

(2) INFORMATION FOR SEQ ID NO:70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:70:

CAAAGGAAGA GTAGCTGTTA                                                  20

(2) INFORMATION FOR SEQ ID NO:71:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:71:

Val Asn Val Ser Leu Glu Asn Val Thr
1               5

(2) INFORMATION FOR SEQ ID NO:72:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:72:
```

```
CAATGTTAGC TTGGAAAATG TCACC                                                  25

(2) INFORMATION FOR SEQ ID NO:73:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:73:

Thr Ala Phe Ile Gln Val Gly Glu
1               5

(2) INFORMATION FOR SEQ ID NO:74:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:74:

AGCATTTATT CAAGTAGGAG                                                        20

(2) INFORMATION FOR SEQ ID NO:75:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:75:

Tyr Leu Leu Ser Thr Ser Ser
1               5

(2) INFORMATION FOR SEQ ID NO:76:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:76:

TCTACTTTCC ACGTCCTCT                                                         19

(2) INFORMATION FOR SEQ ID NO:77:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:77:

Gln Ile Gln Pro Gln Gln Arg
```

(2) INFORMATION FOR SEQ ID NO:78:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:78:

CAGATACAAC CGCAACAGC                                    19

(2) INFORMATION FOR SEQ ID NO:79:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:79:

Pro Gln Gln Arg Ser Thr Gln Ser
1           5

(2) INFORMATION FOR SEQ ID NO:80:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:80:

CCGCAACAGC GTTCAACTCA ATC                              23

(2) INFORMATION FOR SEQ ID NO:81:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:81:

Asp Gly Ala Ile Val Ala Trp
1           5

(2) INFORMATION FOR SEQ ID NO:82:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:82:

GACGGTGCGA TTGTTGCCTG G                                  21

(2) INFORMATION FOR SEQ ID NO:83:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:83:

Glu Gly Asp Ser Gly Thr Val
1               5

(2) INFORMATION FOR SEQ ID NO:84:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:84:

GAAGGAGACT CAGGTACTG                                        19

(2) INFORMATION FOR SEQ ID NO:85:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:85:

Thr Val Thr Asn Thr Ser
1               5

(2) INFORMATION FOR SEQ ID NO:86:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:86:

CCGTAACCAA TACAAGCAC                                        19

(2) INFORMATION FOR SEQ ID NO:87:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:87:

Ser Ser Gln Leu Ala Tyr Asn Pro Ser
1               5

(2) INFORMATION FOR SEQ ID NO:88:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:88:

CTTCACAATT AGCGTATAAT CCTTC                                       25

(2) INFORMATION FOR SEQ ID NO:89:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:89:

Glu Gln His Lys Glu Val Ala
1            5

(2) INFORMATION FOR SEQ ID NO:90:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:90:

GAGCAGCATA AGGAAGTAG                                             19

(2) INFORMATION FOR SEQ ID NO:91:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:91:

Phe Asn Gly Ile Gln Ile Val Pro
1            5

(2) INFORMATION FOR SEQ ID NO:92:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:92:

CATTCAATGG GATTCAAATT GTTCC                                  25

(2) INFORMATION FOR SEQ ID NO:93:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:93:

Val Gln Glu Ser Asn Gly Gly Gly
1               5

(2) INFORMATION FOR SEQ ID NO:94:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:94:

GTGCAGGAAT CTAATGGTGG AGG                                              23

(2) INFORMATION FOR SEQ ID NO:95:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:95:

Glu Ile Gly Gly Lys Phe Thr Leu Asn
1               5

(2) INFORMATION FOR SEQ ID NO:96:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:96:

GATAGGAGGG AAATTTACAT TG                                               22

(2) INFORMATION FOR SEQ ID NO:97:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:97:

CGAATTGAAT GCCGCTTTG                                                   19

(2) INFORMATION FOR SEQ ID NO:98:

(i) SEQUENCE CHARACTERISTICS:
            (A) LENGTH: 22 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:98:

CTCAAAACTK TTTGCTGGCA CC         22

(2) INFORMATION FOR SEQ ID NO:99:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:99:

GGATCRAGCA ACCTCTCTAG         20

(2) INFORMATION FOR SEQ ID NO:100:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:100:

ACTACTTACT TCTAGTAG         18

(2) INFORMATION FOR SEQ ID NO:101:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:101:

Ser Asp Gln Gln Val Val Ile Glu
1               5

(2) INFORMATION FOR SEQ ID NO:102:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:102:

CCGAYCRACA KGTCRTRATT G         21

(2) INFORMATION FOR SEQ ID NO:103:

(i) SEQUENCE CHARACTERISTICS:
        (A) LENGTH: 7 amino acids
        (B) TYPE: amino acid
        (C) STRANDEDNESS: single
        (D) TOPOLOGY: linear

```
    (ii) MOLECULE TYPE: peptide (xi) SEQUENCE DESCRIPTION: SEQ ID NO:103:

Asn Gln Thr Ser Met Thr Glu
1               5

(2) INFORMATION FOR SEQ ID NO:104:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:104:

TCARDCTTCT ATGACAGMAC C                                              21

(2) INFORMATION FOR SEQ ID NO:105:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:105:

Gln Asp Gln Glu Lys Ile Ile Pro
1               5

(2) INFORMATION FOR SEQ ID NO:106:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:106:

CAAGATCAAG ARAARMTYAT YCCT                                           24

(2) INFORMATION FOR SEQ ID NO:107:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:107:

Ser His Lys Gln Asp Gln Glu
1               5

(2) INFORMATION FOR SEQ ID NO:108:

(i) SEQUENCE CHARACTERISTICS:
        (A) LENGTH: 18 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:108:

CTCRTMAACA AGATCAAG                                                    18

(2) INFORMATION FOR SEQ ID NO:109:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:109:

Ser Gly Ser Val Thr Ala His
1               5

(2) INFORMATION FOR SEQ ID NO:110:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:110:

CTGGAARYGT SACGGCTC                                                    18

(2) INFORMATION FOR SEQ ID NO:111:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:111:

GCTTAGTATC TACTTTAAAG AG                                               22

(2) INFORMATION FOR SEQ ID NO:112:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:112:

GATACTATTT GATAAGTTCT CATC                                             24

(2) INFORMATION FOR SEQ ID NO:113:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:113:

CTTTTGGCCT TTTTGCGAAA TAAC                                    24

(2) INFORMATION FOR SEQ ID NO:114:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:114:

CTGGGTTTAA CGCTTTATCA GATTGATATT C                            31

(2) INFORMATION FOR SEQ ID NO:115:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:115:

ACTTTTATTG CTAAACARGC TGC                                     23

(2) INFORMATION FOR SEQ ID NO:116:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:116:

TAACAGCTAC TCTTCCTTTG                                         20

(2) INFORMATION FOR SEQ ID NO:117:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:117:

GGTGACATTT TCCAAGCTAA CATTG                                   25

(2) INFORMATION FOR SEQ ID NO:118:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:118:

AGAGGACGTG GAAAGTAGA                                          19

(2) INFORMATION FOR SEQ ID NO:119:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:119:

GCTGTTGCGG TTGTATCTG                                           19

(2) INFORMATION FOR SEQ ID NO:120:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:120:

GATTGAGTTG AACGCTGTTG CGG                                      23

(2) INFORMATION FOR SEQ ID NO:121:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:121:

CCAGGCAACA ATCGCACCGT C                                        21

(2) INFORMATION FOR SEQ ID NO:122:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:122:

CAGTACCTGA GTCTCCTTC                                           19

(2) INFORMATION FOR SEQ ID NO:123:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:123:

GTGCTTGTAT TGGTTACGG                                           19

(2) INFORMATION FOR SEQ ID NO:124:

(i) SEQUENCE CHARACTERISTICS:
        (A) LENGTH: 25 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:124:

GAAGGATTAT ACGCTAATTG TGAAG                                              25

(2) INFORMATION FOR SEQ ID NO:125:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:125:

GGAACAATTT GAATCCCATT GAATG                                              25

(2) INFORMATION FOR SEQ ID NO:126:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:126:

CCTCCACCAT TAGATTCCTG CAC                                                23

(2) INFORMATION FOR SEQ ID NO:127:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:127:

CAATGTAAAT TTCCCTCCTA TC                                                 22

(2) INFORMATION FOR SEQ ID NO:128:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:128:

GGTGCCAGCA AAMAGTTTTG AG                                                 22

(2) INFORMATION FOR SEQ ID NO:129:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:129:

CTAGAGAGGT TGCTYGATCC                                              20

(2) INFORMATION FOR SEQ ID NO:130:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:130:

CTACTAGAAG TAAGTAGT                                                18

(2) INFORMATION FOR SEQ ID NO:131:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:131:

GGTKCTGTCA TAGAAGHYTG A                                            21

(2) INFORMATION FOR SEQ ID NO:132:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:132:

AGGRATRAKY TTYTCTTGAT CTTG                                         24

(2) INFORMATION FOR SEQ ID NO:133:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:133:

CTTGATCTTG TTKAYGAG                                                18

(2) INFORMATION FOR SEQ ID NO:134:

(i) SEQUENCE CHARACTERISTICS:
        (A) LENGTH: 18 base pairs
        (B) TYPE: nucleic acid
        (C) STRANDEDNESS: single
        (D) TOPOLOGY: linear -continued (ii) MOLECULE TYPE: DNA (genomic)

(xi) SEQUENCE DESCRIPTION: SEQ ID NO:134:

GAGCCGTSAC RYTTCCAG                                                             18

PESTICIDAL TOXINS AND NUCLEOTIDE SEQUENCES WHICH ENCODE THESE TOXINS

The subject application claims priority of Provisional Application No. 60/029,848, filed Oct. 30, 1996.

BACKGROUND OF THE INVENTION

The soil microbe *Bacillus thuringiensis* (B.t.) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain B.t. toxin genes have been isolated and sequenced, and recombinant DNA-based B.t. products have been produced and approved for use. In addition, with the use of genetic engineering techniques, new approaches for delivering these B.t. endotoxins to agricultural environments are under development, including the use of plants genetically engineered with endotoxin genes for insect resistance and the use of stabilized intact microbial cells as B.t. endotoxin delivery vehicles (Gaertner, F. H., L. Kim [1988] *TIBTECH* 6:S4-S7). Thus, isolated B.t. endotoxin genes are becoming commercially valuable.

Until the last fifteen years, commercial use of B.t. pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystalline δ-endotoxin which is toxic to the larvae of a number of lepidopteran insects.

In recent years, however, investigators have discovered B.t. pesticides with specificities for a much broader range of pests. For example, other species of B.t., namely *israelensis* and *morrisoni* (a.k.a. *tenebrionis*, a.k.a. B.t. M-7, a.k.a. B.t. san diego), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255.). See also Couch, T. L. (1980) "Mosquito Pathogenicity of *Bacillus thuringiensis* var. *israelensis*," *Developments in Industrial Microbiology* 22:61–76; and Beegle, C. C. (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508 describe *Bacillus thuringiensis* var. *tenebrionis*, which is reportedly active against two beetles in the order Coleoptera. These are the Colorado potato beetle, *Leptinotarsa decemlineata*, and *Agelastica alni*.

More recently, new subspecies of B.t. have been identified, and genes responsible for active δ-endotoxin proteins have been isolated (Höfte, H., H. R. Whiteley [1989] *Microbiological Reviews* 52(2):242–255). Höfte and Whiteley classified B.t. crystal protein genes into four major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported (Feitelson, J. S., J. Payne, L. Kim [1992] *Bio/Technology* 10:271–275). CryV has been proposed to designate a class of toxin genes that are nematode-specific. Lambert et al. (Lambert, B., L. Buysse, C. Decock, S. Jansens, C. Piens, B. Saey, J. Seurinck, K. van Audenhove, J. Van Rie, A. Van Vliet, M. Peferoen [1996] *Appl. Environ. Microbiol* 62(1):80–86) describe the characterization of a Cry9 toxin active against lepidopterans. Published PCT applications WO 94/05771 and WO 94/24264 also describe B.t. isolates active against lepidopteran pests. Gleave et al. ([1991] *JGM* 138:55–62), Shevelev et al. ([1993] *FEBSLett.* 336:79–82; and Smulevitch et al. ([1991] *FEBS Lett.* 293:25–26) also describe B.t. toxins. Many other classes of B.t. genes have now been identified.

The cloning and expression of a B.t. crystal protein gene in *Escherichia coli* has been described in the published literature (Schnepf, H. E., H. R. Whiteley [1981] *Proc. Natl. Acad. Sci. USA* 78:2893–2897.). U.S. Pat. No. 4,448,885 and U.S. Pat. No. 4,467,036 both disclose the expression of B.t. crystal protein in *E. coli*. U.S. Pat. Nos. 4,990,332; 5,039,523; 5,126,133; 5,164,180; and 5,169,629 are among those which disclose B.t. toxins having activity against lepidopterans. PCT application WO96/05314 discloses PS86W1, PS86W1, and other B.t. isolates active against lepidopteran pests. The PCT patent applications published as WO94/24264 and WO94/05771 describe B.t. isolates and toxins active against lepidopteran pests. B.t. proteins with activity against members of the family Noctuidae are described by Lambert et al., supra. U.S. Pat. Nos. 4,797,276 and 4,853,331 disclose *B. thuringiensis* strain *tenebrionis* which can be used to control coleopteran pests in various environments. U.S. Pat. No. 4,918,006 discloses B.t. toxins having activity against dipterans. U.S. Pat. No. 5,151,363 and U.S. Pat. No. 4,948,734 disclose certain isolates of B.t. which have activity against nematodes. Other U.S. patents which disclose activity against nematodes include U.S. Pat. Nos. 5,093,120; 5,236,843; 5,262,399; 5,270,448; 5,281,530; 5,322,932; 5,350,577; 5,426,049; 5,439,881; 5,667,993; and 5,670,365. As a result of extensive research and investment of resources, other patents have issued for new B.t. isolates and new uses of B.t. isolates. See Feitelson et al., supra, for a review. However, the discovery of new B.t. isolates and new uses of known B.t. isolates remains an empirical, unpredictable art.

Isolating responsible toxin genes has been a slow empirical process. Carozzi et al. (Carozzi, N. B., V. C. Kramer, G. W. Warren, S. Evola, G. Koziel (1991) *Appl. Env. Microbiol.* 57(11):3057–3061) describe methods for identifying toxin genes. U.S. Pat. No. 5,204,237 describes specific and universal probes for the isolation of B.t. toxin genes. That patent, however, does not describe the probes and primers of the subject invention.

WO 94/21795, WO 96/10083, and Estruch, J. J. et al. (1996) *PNAS* 93:5389–5394 describe toxins obtained from Bacillus microbes. These toxins are reported to be produced during vegetative cell growth and were thus termed vegetative insecticidal proteins (VIP). These toxins were reported to be distinct from crystal-forming δ-endotoxins. Activity of these toxins against lepidopteran and coleopteran pests was reported. These applications make specific reference to toxins designated Vip1A(a), Vip1A(b), Vip2A(a), Vip2A(b), Vip3A(a), and Vip3A(b). The toxins and genes of the current invention are distinct from those disclosed in the '795 and '083 applications and the Estruch article.

BRIEF SUMMARY OF THE INVENTION

The subject invention concerns materials and methods useful in the control of non-mammalian pests and, particularly, plant pests. In one embodiment, the subject invention provides novel B.t. isolates having advantageous activity against non-mammalian pests. In a further embodiment, the subject invention provides new toxins useful for the control of non-mammalian pests. In a preferred embodiment, these pests are lepidopterans and/or coleopterans. The toxins of the subject invention include δ-endotoxins as well as soluble toxins which can be obtained from the supernatant of Bacillus cultures.

The subject invention further provides nucleotide sequences which encode the toxins of the subject invention. The subject invention further provides nucleotide sequences and methods useful in the identification and characterization of genes which encode pesticidal toxins.

In one embodiment, the subject invention concerns unique nucleotide sequences which are useful as hybridization probes and/or primers in PCR techniques. The primers produce characteristic gene fragments which can be used in the identification, characterization, and/or isolation of specific toxin genes. The nucleotide sequences of the subject invention encode toxins which are distinct from previously-described toxins.

In a specific embodiment, the subject invention provides new classes of toxins having advantageous pesticidal activities. These classes of toxins can be encoded by polynucleotide sequences which are characterized by their ability to hybridize with certain exemplified sequences and/or by their ability to be amplified by PCR using certain exemplified primers.

One aspect of the subject invention pertains to the identification and characterization of entirely new families of *Bacillus thuringiensis* toxins having advantageous pesticidal properties. Specific new toxin families of the subject invention include MIS-1, MIS-2, MIS-3, MIS-4,MIS-5,MIS-6, WAR-1, and SUP-1. These families of toxins, and the genes which encode them, can be characterized in terms of, for example, the size of the toxin or gene, the DNA or amino acid sequence, pesticidal activity, and/or antibody reactivity. With regard to the genes encoding the novel toxin families of the subject invention, the current disclosure provides unique hybridization probes and PCR primers which can be used to identify and characterize DNA within each of the exemplified families.

In one embodiment of the subject invention, Bacillus isolates can be cultivated under conditions resulting in high multiplication of the microbe. After treating the microbe to provide single-stranded genomic nucleic acid, the DNA can be contacted with the primers of the invention and subjected to PCR amplification. Characteristic fragments of toxin-encoding genes will be amplified by the procedure, thus identifying the presence of the toxin-encoding gene(s).

A further aspect of the subject invention is the use of the disclosed nucleotide sequences as probes to detect genes encoding Bacillus toxins which are active against pests.

Further aspects of the subject invention include the genes and isolates identified using the methods and nucleotide sequences disclosed herein. The genes thus identified encode toxins active against pests. Similarly, the isolates will have activity against these pests. In a preferred embodiment, these pests are lepidopteran or coleopteran pests.

In a preferred embodiment, the subject invention concerns plants cells transformed with at least one polynucleotide sequence of the subject invention such that the transformed plant cells express pesticidal toxins in tissues consumed by target pests. As described herein, the toxins useful according to the subject invention may be chimeric toxins produced by combining portions of multiple toxins. In addition, mixtures and/or combinations of toxins can be used according to the subject invention.

Transformation of plants with the genetic constructs disclosed herein can be accomplished using techniques well known to those skilled in the art and would typically involve modification of the gene to optimize expression of the toxin in plants.

Alternatively, the Bacillus isolates of the subject invention, or recombinant microbes expressing the toxins described herein, can be used to control pests. In this regard, the invention includes the treatment of substantially intact Bacillus cells, and/or recombinant cells containing the expressed toxins of the invention, treated to prolong the pesticidal activity when the substantially intact cells are applied to the environment of a target pest. The treated cell acts as a protective coating for the pesticidal toxin. The toxin becomes active upon ingestion by a target insect.

BRIEF DESCRIPTION OF THE SEQUENCES

SEQ ID NO. 1 is a forward primer, designated "the 339 forward primer," used according to the subject invention.

SEQ ID NO. 2 is a reverse primer, designated "the 339 reverse primer," used according to the subject invention.

SEQ ID NO. 3 is a nucleotide sequence encoding a toxin from B.t. strain PS36A.

SEQ ID NO. 4 is an amino acid sequence for the 36A toxin.

SEQ ID NO. 5 is a nucleotide sequence encoding a toxin from B.t. strain PS81F.

SEQ ID NO. 6 is an amino acid sequence for the 81F toxin.

SEQ ID NO. 7 is a nucleotide sequence encoding a toxin from B.t. strain Javelin 1990.

SEQ ID NO. 8 is an amino acid sequence for the Javelin 1990 toxin

SEQ ID NO. 9 is a forward primer, designated "158C2-PRIMER A" used according to the subject invention.

SEQ ID NO. 10 is a nucleotide sequence encoding a portion of a soluble toxin from B.t. PS158C2.

SEQ ID NO. 11 is a forward primer, designated "49C PRIMER A," used according to the subject invention.

SEQ ID NO. 12 is a nucelotide sequence of a portion of a toxin gene from B.t. strain PS49C.

SEQ ID NO. 13 is a forward primer, designated "49C PRIMER B," used according to the subject invention.

SEQ ID NO. 14 is a reverse primer, designated "49C PRIMER C," used according to the subject invention.

SEQ ID NO. 15 is an additional nucleotide sequence of a portion of a toxin gene from PS49C.

SEQ ID NO. 16 is a forward primer used according to the subject invention.

SEQ ID NO. 17 is a reverse primer used according to the subject invention.

SEQ ID NO. 18 is a nucleotide sequence of a toxin gene from B.t. strain PS10E1.

SEQ ID NO. 19 is an amino acid sequence from the 10E1 toxin.

SEQ ID NO. 20 is a nucleotide sequence of a toxin gene from B.t. strain PS31J2.

SEQ ID NO. 21 is an amino acid sequence from the 31J2 toxin.

SEQ ID NO. 22 is a nucleotide sequence of a toxin gene from B.t. strain PS33D2.

SEQ ID NO. 23 is an amino acid sequence from the 33D2 toxin.

SEQ ID NO. 24 is a nucleotide sequence of a toxin gene from B.t. strain PS66D3.

SEQ ID NO. 25 is an amino acid sequence from the 66D3 toxin.

SEQ ID NO. 26 is a nucleotide sequence of a toxin gene from B.t. strain PS68F.

SEQ ID NO. 27 is an amino acid sequence from the 68F toxin.

SEQ ID NO. 28 is a nucleotide sequence of a toxin gene from B.t. strain PS69AA2.

SEQ ID NO. 29 is an amino acid sequence from the 69AA2 toxin.

SEQ ID NO. 30 is a nucleotide sequence of a toxin gene from B.t. strain PS168G1.

SEQ ID NO. 31 is a nucleotide sequence of a MIS toxin gene from B.t. strain PS77C8.

SEQ ID NO. 32 is an amino acid sequence from the 177C8-MIS toxin.

SEQ ID NO. 33 is a nucleotide sequence of a toxin gene from B.t. strain PS177I8.

SEQ ID NO. 34 is an amino acid sequence from the 177I8 toxin.

SEQ ID NO. 35 is a nucleotide sequence of a toxin gene from B.t. strain PS185AA2.

SEQ ID NO. 36 is an amino acid sequence from the 185AA2 toxin.

SEQ ID NO. 37 is a nucleotide sequence of a toxin gene from B.t. strain PS196F3.

SEQ ID NO. 38 is an amino acid sequence from the 196F3 toxin.

SEQ ID NO. 39 is a nucleotide sequence of a toxin gene from B.t. strain PS196J4.

SEQ ID NO. 40 is an amino acid sequence from the 196J4 toxin.

SEQ ID NO. 41 is a nucleotide sequence of a toxin gene from B.t. strain PS197T1.

SEQ ID NO. 42 is an amino acid sequence from the 197T1 toxin.

SEQ ID NO. 43 is a nucleotide sequence of a toxin gene from B.t. strain PS197U2.

SEQ ID NO. 44 is an amino acid sequence from the 197U2 toxin.

SEQ ID NO. 45 is a nucleotide sequence of a toxin gene from B.t. strain PS202E1.

SEQ ID NO. 46 is an amino acid sequence from the 202E1 toxin.

SEQ ID NO. 47 is a nucleotide sequence of a toxin gene from B.t. strain KB33.

SEQ ID NO. 48 is a nucleotide sequence of a toxin gene from B.t. strain KB38.

SEQ ID NO. 49 is a forward primer, designated "ICON-forward," used according to the subject invention.

SEQ ID NO. 50 is a reverse primer, designated "ICON-reverse," used according to the subject invention.

SEQ ID NO. 51 is a nucleotide sequence encoding a 177C8-WAR toxin gene from B.t. strain PS177C8.

SEQ ID NO. 52 is an amino acid sequence of a 177C8-WAR toxin from B.t. strain PS177C8.

SEQ ID NO. 53 is a forward primer, designated "SUP-1A," used according to the subject invention.

SEQ ID NO. 54 is a reverse primer, designated "SUP-1B," used according to the subject invention.

SEQ ID NOS. 55–110 are primers used according to the subject invention.

SEQ ID NO. 111 is the reverse complement of the primer of SEQ ID NO. 58.

SEQ ID NO. 112 is the reverse complement of the primer of SEQ ID NO. 60.

SEQ ID NO. 113 is the reverse complement of the primer of SEQ ID NO. 64.

SEQ ID NO. 114 is the reverse complement of the primer of SEQ ID NO. 66.

SEQ ID NO. 115 is the reverse complement of the primer of SEQ ID NO. 68.

SEQ ID NO. 116 is the reverse complement of the primer of SEQ ID NO. 70.

SEQ ID NO. 117 is the reverse complement of the primer of SEQ ID NO. 72.

SEQ ID NO. 118 is the reverse complement of the primer of SEQ ID NO. 76.

SEQ ID NO. 119 is the reverse complement of the primer of SEQ ID NO. 78.

SEQ ID NO. 120 is the reverse complement of the primer of SEQ ID NO. 80.

SEQ ID NO. 121 is the reverse complement of the primer of SEQ ID NO. 82.

SEQ ID NO. 122 is the reverse complement of the primer of SEQ ID NO. 84.

SEQ ID NO. 123 is the reverse complement of the primer of SEQ ID NO. 86.

SEQ ID NO. 124 is the reverse complement of the primer of SEQ ID NO. 88.

SEQ ID NO. 125 is the reverse complement of the primer of SEQ ID NO. 92.

SEQ ID NO. 126 is the reverse complement of the primer of SEQ ID NO. 94.

SEQ ID NO. 127 is the reverse complement of the primer of SEQ ID NO. 96.

SEQ ID NO. 128 is the reverse complement of the primer of SEQ ID NO. 98.

SEQ ID NO. 129 is the reverse complement of the primer of SEQ ID NO. 99.

SEQ ID NO. 130 is the reverse complement of the primer of SEQ ID NO. 100.

SEQ ID NO. 131 is the reverse complement of the primer of SEQ ID NO. 104.

SEQ ID NO. 132 is the reverse complement of the primer of SEQ ID NO. 106.

SEQ ID NO. 133 is the reverse complement of the primer of SEQ ID NO. 108.

SEQ ID NO. 134 is the reverse complement of the primer of SEQ ID NO. 108.

DETAILED DISCLOSURE OF THE INVENTION

The subject invention concerns materials and methods for the control of non-mammalian pests. In specific embodiments, the subject invention pertains to new *Bacillus thuringiensis* isolates and toxins which have activity against lepidopterans and/or coleopterans. The subject invention further concerns novel genes which encode pesticidal toxins and novel methods for identifying and characterizing Bacillus genes which encode toxins with useful properties. The subject invention concerns not only the polynucleotide sequences which encode these toxins, but also the use of these polynucleotide sequences to produce recombinanthosts which express the toxins. The proteins of the subject invention are distinct from protein toxins which have previously been isolated from *Bacillus thuringiensis*.

B.t. isolates useful according to the subject invention have been deposited in the permanent collection of the Agricultural Research Service Patent Culture Collection (NRRL), Northern Regional Research Center, 1815 North University Street, Peoria, Ill. 61604, U.S.A. The culture repository numbers of the B.t. strains are as follows:

| Culture | Repository No. | Deposit Date | Patent No. |
| --- | --- | --- | --- |
| B.t. PS11B (MT274) | NRRL B-21556 | April 18, 1996 | |
| B.t. PS24J | NRRL B-18881 | August 30, 1991 | |
| B.t. PS31G1 (MT278) | NRRL B-21560 | April 18, 1996 | |
| B.t. PS36A | NRRL B-18929 | December 27, 1991 | |
| B.t. PS33F2 | NRRL B-18244 | July 28, 1987 | 4,861,595 |
| B.t. PS40D1 | NRRL B-18300 | February 3, 1988 | 5,098,705 |
| B.t. PS43F | NRRL B-18298 | February 2, 1988 | 4,996,155 |
| B.t. PS45B1 | NRRL B-18396 | August 16, 1988 | 5,427,786 |
| B.t. PS49C | NRRL B-21532 | March 14, 1996 | |
| B.t. PS52A1 | NRRL B-18245 | July 28, 1987 | 4,861,595 |
| B.t. PS62B1 | NRRL B-18398 | August 16, 1988 | 4,849,217 |
| B.t. PS81A2 | NRRL B-18450 | March 7, 1989 | 5,164,180 |
| B.t. PS81F | NRRL B-18424 | October 7, 1988 | 5,045,469 |
| B.t. PS81GG | NRRL B-18425 | October 11, 1988 | 5,169,629 |
| B.t. PS81I | NRRL B-18484 | April 19, 1989 | 5,126,133 |
| B.t. PS85A1 | NRRL B-18426 | October 11, 1988 | |
| B.t. PS86A1 | NRRL B-18400 | August 16, 1988 | 4,849,217 |
| B.t. PS86B1 | NRRL B-18299 | February 2, 1988 | 4,966,765 |
| B.t. PS86BB1 (MT275) | NRRL B-21557 | April 18, 1996 | |
| B.t. PS86Q3 | NRRL B-18765 | February 6, 1991 | 5,208,017 |
| B.t. PS86V1 (MT276) | NRRL B-21558 | April 18, 1996 | |
| B.t. PS86W1 (MT277) | NRRL B-21559 | April 18, 1996 | |
| B.t. PS89J3 (MT279) | NRRL B-21561 | April 18, 1996 | |
| B.t. PS91C2 | NRRL B-18931 | February 6, 1991 | |
| B.t. PS92B | NRRL B-18889 | September 23, 1991 | 5,427,786 |
| B.t. PS101Z2 | NRRL B-18890 | October 1, 1991 | 5,427,786 |
| B.t. PS122D3 | NRRL B-18376 | June 9, 1988 | 5,006,336 |
| B.t. PS123D1 | NRRL B-21011 | October 13, 1992 | 5,508,032 |
| B.t. PS157C1 (MT104) | NRRL B-18240 | July 17, 1987 | 5,262,159 |
| B.t. PS158C2 | NRRL B-18872 | August 27, 1991 | 5,268,172 |
| B.t. PS169E | NRRL B-18682 | July 17, 1990 | 5,151,363 |
| B.t. PS177F1 | NRRL B-18683 | July 17, 1990 | 5,151,363 |
| B.t. PS177G | NRRL B-18684 | July 17, 1990 | 5,151,363 |
| B.t. PS185L2 | NRRL B-21535 | March 14, 1996 | |
| B.t. PS185U2 (MT280) | NRRL B-21562 | April 18, 1996 | |
| B.t. PS192M4 | NRRL B-18932 | December 27, 1991 | 5,273,746 |
| B.t. PS201L1 | NRRL B-18749 | January 9, 1991 | 5,298,245 |
| B.t. PS204C3 | NRRL B-21008 | October 6, 1992 | |
| B.t. PS204G4 | NRRL B-18685 | July 17, 1990 | 5,262,399 |
| B.t. PS242H10 | NRRL B-25439 | March 14, 1996 | |
| B.t. PS242K17 | NRRL B-21540 | March 14, 1996 | |
| B.t. PS244A2 | NRRL B-21541 | March 14, 1996 | |
| B.t. PS244D1 | NRRL B-21542 | March1 4, 1996 | |
| B.t. PS10E1 | NRRL B-21862 | October 24, 1997 | |
| B.t. PS31F2 | NRRL B-21876 | October 24, 1997 | |
| B.t. PS31J2 | NRRL B-21009 | October 13, 1992 | |
| B.t. PS33D2 | NRRL B-21870 | October 24, 1997 | |
| B.t. PS66D3 | NRRL B-21858 | October 24, 1997 | |
| B.t. PS68F | NRRL B-21857 | October 24, 1997 | |
| B.t. PS69AA2 | NRRL B-21859 | October 24, 1997 | |
| B.t. PS146D | NRRL B-21866 | October 24, 1997 | |
| B.t. PS168G1 | NRRL B-21873 | October 24, 1997 | |
| B.t. PS175I4 | NRRL B-21865 | October 24, 1997 | |
| B.t. PS177C8a | NRRL B-21867 | October 24, 1997 | |
| B.t. PS17718 | NRRL B-21868 | October 24, 1997 | |
| B.t. PS185AA2 | NRRL B-21861 | October 24, 1997 | |
| B.t. PS196J4 | NRRL B-21860 | October 24, 1997 | |
| B.t. PS196F3 | NRRL B-21872 | October 24, 1997 | |
| B.t. PS197T1 | NRRL B-21869 | October 24, 1997 | |
| B.t. PS197U2 | NRRL B-21871 | October 24, 1997 | |
| B.t. PS202E1 | NRRL B-21874 | October 24, 1997 | |
| B.t. PS217U2 | NRRL B-21864 | October 24, 1997 | |
| KB33 | NRRL B-21875 | October 24, 1997 | |
| KB38 | NRRL B-21863 | October 24, 1997 | |
| KB53A49-4 | NRRL B-21879 | October 24, 1997 | |
| KB68B46-2 | NRRL B-21877 | October 24, 1997 | |
| KB68B51-2 | NRRL B-21880 | October 24, 1997 | |
| KB68B55-2 | NRRL B-21878 | October 24, 1997 | |
| PS80JJ1 | NRRL B-18679 | July 17, 1990 | 5,151,363 |
| PS94R1 | NRRL B-21801 | July 1, 1997 | |
| PS101DD | NRRL B-21802 | July 1, 1997 | |
| PS202S | NRRL B-21803 | July 1, 1997 | |
| PS213E5 | NRRL B-21804 | July 1, 1997 | |
| PS218G2 | NRRL B-21805 | July 1, 1997 | |

Cultures which have been deposited for the purposes of this patent application were deposited under conditions that assure that access to the cultures is available during the pendency of this patent application to one determined by the Commissioner of Patents and Trademarks to be entitled thereto under 37 CFR 1.14 and 35 U.S.C. 122. The deposits will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the culture(s). The depositor acknowledges the duty to replace the deposit(s) should the depository be unable to furnish a sample when requested, due to the condition of a deposit. All restrictions on the availability to the public of the subjectculture deposits will be irrevocably removed upon the granting of a patent disclosing them.

Many of the strains useful according to the subject invention are readily available by virtue of the issuance of patents disclosing these strains or by their deposit in public collections or by their inclusion in commercial products. For example, the B.t. strain used in the commercial product, Javelin, and the HD isolates are all publicly available.

Mutants of the isolates referred to herein can be made by procedures well known in the art. For example, an asporogenous mutant can be obtained through ethylmethane sulfonate (EMS) mutagenesis of an isolate. The mutants can be made using ultraviolet light and nitrosoguanidine by procedures well known in the art.

In one embodiment, the subject invention concerns materials and methods including nucleotide primers and probes for isolating, characterizing, and identifying Bacillus genes encoding protein toxins which are active against nonmammalian pests. The nucleotide sequences described herein can also be used to identify new pesticidal Bacillus isolates. The invention further concerns the genes, isolates, and toxins identified using the methods and materials disclosed herein.

The new toxins and polynucleotide sequences provided here are defined according to several parameters. One characteristic of the toxins described herein is pesticidal activity. In a specific embodiment, these toxins have activity against coleopteran and/or lepidopteran pests. The toxins and genes of the subject invention can be further defined by their amino acid and nucleotide sequences. The sequences of the molecules can be defined in terms of homology to certain exemplified sequences as well as in terms of the ability to hybridize with, or be amplified by, certain exemplified-probes and primers. The toxins providedherein can also be identified based on their immunoreactivity with certain antibodies.

An important aspect of the subject invention is the identificationand characterization of new families of Bacillus toxins, and genes which encode these toxins. These families have been designated MIS-1, MIS-2, MIS-3, MIS-4, MIS-5, MIS-6, WAR-1, and SUP-1. Toxins within these families, as well as genes encoding toxins within these families, can readily be identified as described herein by, for example, size, amino acid or DNA sequence, and antibody reactivity. Amino acid and DNA sequence characteristics include homology with exemplified sequences, ability to hybridize with DNA probes, and ability to be amplified with specific primers.

The MIS-1 family of toxins includes toxins from isolate PS68F. Also provided are hybridization probes and PCR primers which specifically identify genes falling in the MIS-1 family.

A second family of toxins identified herein is the MIS-2 family. This family includes toxins which can be obtained from isolates PS66D3, PS197T1, and PS31J2. The subject invention further provides probes and primers for the identification of MIS-2 toxins and genes.

A third family of toxins identified herein is the MIS-3 family. This family includes toxins which can be obtained from B.t. isolates PS69AA2 and PS33D2. The subject invention further provides probes and primers for identification of the MIS-3 genes and toxins.

Polynucleotide sequences encoding MIS-4 toxins can be obtained from the B.t. isolate designated PS197U2. The subject invention further provides probes and primers for the identification of genes and toxins in this family.

A fifth family of toxins identified herein is the MIS-5 family. This family includes toxins which can be obtained from B.t. isolates KB33 and KB38. The subject invention further provides probes and primers for identification of the MIS-5 genes and toxins.

A sixth family of toxins identified herein is the MIS-6 family. This family includes toxins which can be obtained from B.t. isolates PS196F3, PS168G1, PS196J4, PS202E1, PS10E1, and PS185AA2. The subject invention further provides probes and primers for identification of the MIS-6 genes and toxins.

In a preferred embodiment, the genes of the MIS family encode toxins having a molecular weight of about 70 to about 100 kDa and, most preferably, the toxins have a size of about 80 kDa. Typically, these toxins are soluble and can be obtained from the supernatant of Bacillus cultures as described herein. These toxins have toxicity against non-mammalian pests. In a preferred embodiment, these toxins have activity against coleopteran pests. The MIS proteins are further useful due to their ability to form pores in cells. These proteins can be used with second entities including, for example, other proteins. When used with a second entity, the MIS protein will facilitate entry of the second agent into a target cell. In a preferred embodiment, the MIS protein interacts with MIS receptors in a target cell and causes pore formation in the target cell. The second entity may be a toxin or another molecule whose entry into the cell is desired.

The subject invention further concerns a family of toxins designated WAR-1. The WAR-1 toxins typically have a size of about 30–50 kDa and, most typically, have a size of about 40 kDa. Typically, these toxins are soluble and can be obtained from the supernatant of Bacillus cultures as described herein. The WAR-1 toxins can be identified with primers described herein as well as with antibodies. In a specific embodiment, the antibodies can be raised to, for example, toxin from isolate PS177C8.

An additional family of toxins provided according to the subject invention are the toxins designated SUP-1. Typically, these toxins are soluble and can be obtained from the supernatant of Bacillus cultures as described herein. In a preferred embodiment, the SUP-1 toxins are active against lepidopteran pests. The SUP-1 toxins typically have a size of about 70–100 kDa and, preferably, about 80 kDa. The SUP-1 family is exemplified herein by toxins from isolates PS49C and PS158C2. The subject invention provides probes and primers useful for the identification of toxins and genes in the SUP-1 family The subject invention further provides specific Bacillus toxins and genes which did not fall into any of the new families disclosed herein. These specific toxins and genes include toxins and genes which can be obtained from PS177C8 and PS177I8.

Toxins in the MIS, WAR, and SUP families are all soluble and can be obtained as described herein from the supernatant of Bacillus cultures. These toxins can be used alone or in combination with other toxins to control pests. For example, toxins from the MIS families may be used in conjunction with WAR-type toxins to achieve control of pests, particularly coleopteran pests. These toxins may be used, for example, with δ-endotoxins which are obtained from Bacillus isolates.

Table 1 provides a summary of the novel families of toxins and genes of the subject invention. Each of the six MIS families is specifically exemplified herein by toxins which can be obtained from particular B.t. isolates as shown in Table 1. Genes encoding toxins in each of these families can be identified by a variety of highly specific parameters, including the ability to hybridize with the particular probes set forth in Table 1. Sequence identity in excess of about 80% with the probes set forth in Table 1 can also be used to identify the genes of the various families. Also exemplified are particular primer pairs which can be used to amplify the genes of the subject invention. A portion of a gene within the indicated families would typically be amplifiable with at least one of the enumerated primer pairs. In a preferred embodiment, the amplified portion would be of approximately the indicated fragment size. Primers shown in Table 1 consist of polynucleotide sequences which encode peptides as shown in the sequence listing attached hereto. Additional primers and probes can readily be constructed by those skilled in the art such that alternate polynucleotide sequences encoding the same amino acid sequences can be used to identify and/or characterize additional genes encoding pesticidal toxins. In a preferred embodiment, these additional toxins, and their genes, could be obtained from Bacillus isolates.

TABLE 1

| Family | Isolates | Probes (SEQ ID NO.) | Primer Pairs (SEQ ID NOS.) | Fragment size (nt) |
|---|---|---|---|---|
| MIS-1 | PS68F | 26 | 56 and 111 | 69 |
|  |  |  | 56 and 112 | 506 |
|  |  |  | 58 and 112 | 458 |
| MIS-2 | PS66D3, PS197T1, PS31J2 | 24, 41, 20 | 62 and 113 | 160 |
|  |  |  | 62 and 114 | 239 |
|  |  |  | 62 and 115 | 400 |
|  |  |  | 62 and 116 | 509 |
|  |  |  | 62 and 117 | 703 |
|  |  |  | 64 and 114 | 102 |
|  |  |  | 64 and 115 | 263 |
|  |  |  | 64 and 116 | 372 |
|  |  |  | 64 and 117 | 566 |
|  |  |  | 66 and 115 | 191 |
|  |  |  | 66 and 116 | 300 |
|  |  |  | 66 and 117 | 494 |
|  |  |  | 68 and 116 | 131 |
|  |  |  | 68 and 117 | 325 |
|  |  |  | 70 and 117 | 213 |
| MIS-3 | PS69AA2, PS33D2 | 28, 22 | 74 and 118 | 141 |
|  |  |  | 74 and 119 | 376 |
|  |  |  | 74 and 120 | 389 |
|  |  |  | 74 and 121 | 483 |
|  |  |  | 74 and 122 | 715 |
|  |  |  | 74 and 123 | 743 |
|  |  |  | 74 and 124 | 902 |
|  |  |  | 76 and 119 | 253 |
|  |  |  | 76 and 120 | 266 |
|  |  |  | 76 and 121 | 360 |
|  |  |  | 76 and 122 | 592 |
|  |  |  | 76 and 123 | 620 |
|  |  |  | 76 and 124 | 779 |
|  |  |  | 78 and 120 | 31 |
|  |  |  | 78 and 121 | 125 |
|  |  |  | 78 and 122 | 357 |
|  |  |  | 78 and 123 | 385 |
|  |  |  | 78 and 124 | 544 |
|  |  |  | 80 and 121 | 116 |
|  |  |  | 80 and 122 | 348 |
|  |  |  | 80 and 123 | 376 |
|  |  |  | 80 and 124 | 535 |
|  |  |  | 82 and 122 | 252 |
|  |  |  | 82 and 123 | 280 |
|  |  |  | 82 and 124 | 439 |
|  |  |  | 84 and 123 | 46 |
|  |  |  | 84 and 124 | 205 |
|  |  |  | 86 and 124 | 177 |
| MIS-4 | PS197U2 | 43 | 90 and 125 | 517 |
|  |  |  | 90 and 126 | 751 |
|  |  |  | 90 and 127 | 821 |
|  |  |  | 92 and 126 | 258 |
|  |  |  | 92 and 127 | 328 |
|  |  |  | 94 and 127 | 92 |
| MIS-5 | KB33, KB38 | 47, 48 | 97 and 128 | 109 |
|  |  |  | 97 and 129 | 379 |
|  |  |  | 97 and 130 | 504 |
|  |  |  | 98 and 129 | 291 |
|  |  |  | 98 and 130 | 416 |
|  |  |  | 99 and 130 | 144 |
| MIS-6 | PS196F3, PS168G1, PS196J4, PS202E1, PS10E1, PS185AA2 | 18, 30, 35, 37, 39, 45 | 102 and 131 | 66 |
|  |  |  | 102 and 132 | 259 |
|  |  |  | 102 and 133 | 245 |
|  |  |  | 102 and 134 | 754 |
|  |  |  | 104 and 132 | 213 |
|  |  |  | 104 and 133 | 199 |
|  |  |  | 104 and 134 | 708 |
|  |  |  | 106 and 133 | 31 |
|  |  |  | 106 and 134 | 518 |
|  |  |  | 108 and 134 | 526 |
| SUP1 | PS49C, PS158C2 | 10, 12, 15 | 53 and 54 | 370 |

Furthermore, chimeric toxins may be used according to the subject invention. Methods have been developed for making useful chimeric toxins by combining portions of B.t. crystal proteins. The portions which are combined need not, themselves, be pesticidal so long as the combination of portions creates a chimeric protein which is pesticidal. This can be done using restriction enzymes, as described in, for example, European Patent 0 228 838; Ge, A. Z., N. L.

Shivarova, D. H. Dean (1989) *Proc. Natl. Acad Sci. USA* 86:4037–4041; Ge, A. Z., D. Rivers, R. Milne, D. H. Dean (1991) *J. Biol. Chem.* 266:17954–17958; Schnepf, H. E., K. Tomczak, J. P. Ortega, H. R. Whiteley (1990) *J. Biol. Chem.* 265:20923–20930; Honee, G., D. Convents, J. Van Rie, S. Jansens, M. Peferoen, B. Visser (1991) *Mol. Microbiol* 5:2799–2806. Alternatively, recombination using cellular recombination mechanisms can be used to achieve similar results. See, for example, Caramori, T., A. M. Albertini, A. Galizzi (1991) *Gene* 98:37–44; Widner, W. R., H. R. Whiteley (1990) *J. Bacteriol.* 172:2826–2832; Bosch, D., B. Schipper, H. van der Kliej, R. A. de Maagd, W. J. Stickema (1994) *Biotechnology* 12:915–918. A number of other methods are known in the art by which such chimeric DNAs can be made. The subject invention is meant to include chimeric proteins that utilize the novel sequences identified in the subject application.

With the teachings provided herein, one skilled in the art could readily produce and use the various toxins and polynucleotide sequences described herein.

Genes and toxins. The genes and toxins useful according to the subject invention include not only the full length sequences but also fragments of these sequences, variants, mutants, and fusion proteins which retain the characteristic pesticidal activity of the toxins specifically exemplified herein. Chimeric genes and toxins, produced by combining portions from more than one Bacillus toxin or gene, may also be utilized according to the teachings of the subject invention. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the exemplified toxins.

It is apparent to a person skilled in this art that genes encoding active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from Bacillus isolates and/or DNA libraries using the teachings provided herein. There are a number of methods for obtaining the pesticidal toxins of the instant invention. For example, antibodies to the pesticidal toxins disclosed and claimed herein can be used to identify and isolate toxins from a mixture of proteins. Specifically, antibodies may be raised to the portions of the toxins which are most constant and most distinct from other Bacillus toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins are within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying the toxins and genes of the subject invention is through the use of oligonucleotide probes. These probes are detectable nucleotide sequences. Probes provide a rapid method for identifying toxin-encoding genes of the subject invention. The nucleotide segments which are used as probes according to the invention can be synthesized using a DNA synthesizer and standard procedures.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid identity will typically be greater than 60%, preferably be greater than 75%, more preferably greater than 80%, more preferably greater than 90%, and can be greater than 95%. These identities are as determined using standard alignment techniques. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 2 provides a listing of examples of amino acids belonging to each class.

TABLE 2

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The δ-endotoxins of the subject invention can also be characterized in terms of the shape and location of toxin inclusions, which are described above.

As used herein, reference to "isolated" polynucleotides and/or "purified" toxins refers to these molecules when they are not associated with the other molecules with which they would be found in nature. Thus, reference to "isolated and purified" signifies the involvement of the "hand of man" as described herein. Chimeric toxins and genes also involve the "hand of man."

Recombinant hosts. The toxin-encoding genes of the subject invention can be introduced into a wide variety of microbial or plant hosts. Expression of the toxin gene results, directly or indirectly, in the production and maintenance of the pesticide. With suitable microbial hosts, e.g., Pseudomonas, the microbes can be applied to the situs of the pest, where they will proliferate and be ingested. The result is a control of the pest. Alternatively, the microbe hosting the toxin gene can be killed and treated under conditions that prolong the activity of the toxin and stabilize the cell. The treated cell, which retains the toxic activity, then can be applied to the environment of the target pest.

Where the Bacillus toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A wide variety of ways are available for introducing a Bacillus gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Synthetic genes which are functionally equivalent to the toxins of the subject invention can also be used to transform hosts. Methods for the production of synthetic genes can be found in, for example, U.S. Pat. No. 5,380,831.

Treatment of cells. As mentioned above, Bacillus or recombinant cells expressing a Bacillus toxin can be treated to prolong the toxin activity and stabilize the cell. The pesticide microcapsule that is formed comprises the Bacillus toxin within a cellular structure that has been stabilized and will protect the toxin when the microcapsule is applied to the environment of the target pest. Suitable host cells may include either prokaryotes or eukaryotes. As hosts, of particular interest will be the prokaryotes and the lower eukaryotes, such as fungi. The cell will usually be intact and be substantially in the proliferative form when treated, rather than in a spore form.

Treatment of the microbial cell, e.g., a microbe containing the Bacillus toxin gene, can be by chemical or physical means, or by a combination of chemical and/or physical means, so long as the technique does not deleteriously affect the properties of the toxin, nor diminish the cellular capability of protecting the toxin. Methods for treatment of microbial cells are disclosed in U.S. Pat. Nos. 4,695,455 and 4,695,462, which are incorporated herein by reference.

Methods and formulations for control of pests. Control of pests using the isolates, toxins, and genes of the subject invention can be accomplished by a variety of methods known to those skilled in the art. These methods include, for example, the application of Bacillus isolates to the pests (or their location), the application of recombinant microbes to the pests (or their locations), and the transformation of plants with genes which encode the pesticidal toxins of the subject invention. Transformations can be made by those skilled in the art using standard techniques. Materials necessary for these transformations are disclosed herein or are otherwise readily available to the skilled artisan.

Formulated bait granules containing an attractant and the toxins of the Bacillus isolates, or recombinant microbes comprising the genes obtainable from the Bacillus isolates disclosed herein, can be applied to the soil. Formulated product can also be applied as a seed-coating or root treatment or total plant treatment at later stages of the crop cycle. Plant and soil treatments of Bacillus cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations that contain cells will generally have from about $10^2$ to about $10^4$ cells/mg. These formulations will be administered at about 50 mg (liquid or dry) to 1 kg or more per hectare.

The formulations can be applied to the environment of the pest, e.g, soil and foliage, by spraying, dusting, sprinkling, or the like.

Polynucleotide probes. It is well known that DNA possesses a fundamental property called base complementarity. In nature, DNA ordinarily exists in the form of pairs of anti-parallel strands, the bases on each strand projecting from that strand toward the opposite strand. The base adenine (A) on one strand will always be opposed to the base thymine (T) on the other strand, and the base guanine (G) will be opposed to the base cytosine (C). The bases are held in apposition by their ability to hydrogen bond in this specific way. Though each individual bond is relatively weak, the net effect of many adjacent hydrogen bonded bases, together with base stacking effects, is a stable joining of the two complementary strands. These bonds can be broken by treatments such as high pH or high temperature, and these conditions result in the dissociation, or "denaturation," of the two strands. If the DNA is then placed in conditions which make hydrogen bonding of the bases thermodynamically favorable, the DNA strands will anneal, or "hybridize," and reform the original double stranded DNA. If carried out under appropriate conditions, this hybridization can be highly specific. That is, only strands with a high degree of base complementarity will be able to form stable double stranded structures. The relationship of the specificity of hybridization to reaction conditions is well known. Thus, hybridization may be used to test whether two pieces of DNA are complementary in their base sequences. It is this hybridization mechanism which facilitates the use of probes of the subject invention to readily detect and characterize DNA sequences of interest.

The probes may be RNA or DNA. The probe will normally have at least about 10 bases, more usually at least about 17 bases, and may have up to about 100 bases or more. Longer probes can readily be utilized, and such probes can be, for example, several kilobases in length. The probe sequence is designed to be at least substantially complementary to a portion of a gene encoding a toxin of interest. The probe need not have perfect complementarity to the sequence to which it hybridizes. The probes may be labelled utilizing techniques which are well known to those skilled in this art.

One approach for the use of the subject invention as probes entails first identifying by Southern blot analysis of a gene bank of the Bacillus isolate all DNA segments homologous with the disclosed nucleotide sequences. Thus, it is possible, without the aid of biological analysis, to know in advance the probable activity of many new Bacillus isolates, and of the individual gene products expressed by a given Bacillus isolate. Such a probe analysis provides a rapid method for identifying potentially commercially valuable insecticidal toxin genes within the multifarious subspecies of B.t.

One hybridization procedure useful according to the subject invention typically includes the initial steps of isolating the DNA sample of interest and purifying it chemically. Either lysed bacteria or total fractionated nucleic acid isolated from bacteria can be used. Cells can be treated using known techniques to liberate their DNA (and/or RNA). The DNA sample can be cut into pieces with an appropriate restriction enzyme. The pieces can be separated by size through electrophoresisin a gel, usually agarose or acrylamide. The pieces of interest can be transferred to an immobilizing membrane.

The particular hybridization technique is not essential to the subject invention. As improvements are made in hybridization techniques, they can be readily applied.

The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical. The probe's detectable label provides a means for determining in a known manner whether hybridization has occurred.

In the use of the nucleotide segments as probes, the particular probe is labeled with any suitable label known to those skilled in the art, including radioactive and non-radioactive labels. Typical radioactive labels include $^{32}P$, $^{35}S$, or the like. Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probes may be made inherently fluorescent as described in International Application No. WO 93/16094.

Various degrees of stringency of hybridization can be employed. The more severe the conditions, the greater the complementarity that is required for duplex formation. Severity can be controlled by temperature, probe concentration, probe length, ionic strength, time, and the like. Preferably, hybridization is conducted under moderate to high stringency conditions by techniques well known in the art, as described, for example, in Keller, G. H., M. M. Manak (1987) *DNA Probes*, Stockton Press, New York, N.Y., pp. 169–170.

As used herein "moderate to high stringency" conditions for hybridization refers to conditions which achieve the same, or about the same, degree of specificity of hybridization as the conditions employed by the current applicants. Examples of moderate and high stringency conditions are provided herein. Specifically, hybridization of emmobilized DNA on Southern blots with 32P-labeled gene-specific probes was performed by standard methods (Maniatis et al.). In general, hybridization and subsequent washes were carried out under moderate to high stringency conditions that allowed for detection of target sequences with homology to the exemplified toxin genes. For double-stranded DNA gene probes, hybridization was carried out overnight at 20–25° C. below the melting temperature (Tm) of the DNA hybrid in 6× SSPE, 5× Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology*, R. Wu, L. Grossman and K. Moldave [eds.] Academic Press, New York 100:266–285).

$$Tm=81.50° C.+16.6 \text{ Log } [Na+]+0.41(\%G+C)-0.61(\%formamide)-600/\text{length of duplex in base pairs.}$$

Washes are typically carried out as follows:

(1) Twice at room temperature for 15 minutes in 1× SSPE, 0.1% SDS (low stringency wash).

(2) Once at Tm-20° C. for 15 minutes in 0.2× SSPE, 0.1% SDS (moderate stringency wash).

For oligonucleotide probes, hybridization was carried out overnight at 10–20° C. below the melting temperature (Tm) of the hybrid in 6× SSPE, 5× Denhardt's solution, 0.1% SDS, 0.1 mg/ml denatured DNA. Tm for oligonucleotide probes was determined by the following formula:

Tm (°C.)=2(number T/A base pairs)+4(number G/C base pairs)

(Suggs, S. V., T. Miyake, E. H. Kawashime, M. J. Johnson, K. Itakura, and R. B. Wallace [1981] *ICN-UCLA Symp. Dev. Biol. Using Purified Genes*, D. D. Brown [ed.], Academic Press, New York, 23:683–693).

Washes were typically carried out as follows:
(1) Twice at room temperature for 15 minutes 1× SSPE, 0.1% SDS (low stringency wash).
(2) Once at the hybridization temperature for 15 minutes in 1× SSPE, 0.1% SDS (moderate stringency wash).

In general, salt and/or temperature can be altered to change stringency. With a labeled DNA fragment >70 or so bases in length, the following conditions can be used:
Low: 1 or 2× SSPE, room temperature
Low: 1 or 2× SSPE, 42° C.
Moderate: 0.2× or 1× SSPE, 65° C.
High: 0.1× SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

Thus, mutational, insertional, and deletional variants of the disclosed nucleotide sequences can be readily prepared by methods which are well known to those skilled in the art. These variants can be used in the same manner as the exemplified primer sequences so long as the variants have substantial sequence homology with the original sequence. As used herein, substantial sequence homology refers to homology which is sufficient to enable the variant probe to function in the same capacity as the original probe. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

PCR technology. Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of β-Globin Genomic Sequences and Restriction Site Analysis for Diagnosis of Sickle Cell Anemia," *Science* 230:1350–1354.). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thermus aquaticus*, the amplification process can be completely automated. Other enzymes which can be used are known to those skilled in the art.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions and deletions can be produced in a given primer by methods known to an ordinarily skilled artisan.

All of the U.S. patents cited herein are hereby incorporated by reference.

Following are examples which illustrate procedures for practicing the invention. These examples should not be construed as limiting. All percentages are by weight and all solvent mixture proportions are by volume unless otherwise noted.

EXAMPLE 1

Culturing of Bacillus Isolates Useful According to the Invention

Growth of cells. The cellular host containing the Bacillus insecticidal gene may be grown in any convenient nutrient medium. These cells may then be harvested in accordance with conventional ways. Alternatively, the cells can be treated prior to harvesting.

The Bacillus cells of the invention can be cultured using standard art media and fermentation techniques. During the fermentation cycle, the bacteria can be harvested by first separating the Bacillus vegetative cells, spores, crystals, and lysed cellular debris from the fermentation broth by means well known in the art. Any Bacillus spores or crystal δ-endotoxins formed can be recovered employing well-known techniques and used as a conventional δ-endotoxin B.t. preparation. The supernatant from the fermentation process contains the toxins of the present invention. The toxins are isolated and purified employing well-known techniques.

A subculture of Bacillus isolates, or mutants thereof, can be used to inoculate the following medium, known as TB broth:

| | |
|---|---|
| Tryptone | 12 g/l |
| Yeast Extract | 24 g/l |
| Glycerol | 4 g/l |
| $KH_2PO_4$ | 2.1 g/l |
| $K_2HPO_4$ | 14.7 g/l |
| pH 7.4 | |

The potassium phosphate was added to the autoclaved broth after cooling. Flasks were incubated at 30° C. on a rotary shaker at 250 rpm for 24–36 hours.

The above procedure can be readily scaled up to large fermentors by procedures well known in the art.

The Bacillus obtained in the above fermentation, can be isolated by procedures well known in the art. A frequently-used procedure is to subject the harvested fermentation broth to separation techniques, e.g., centrifugation. In a specific embodiment, Bacillus proteins useful according the present invention can be obtained from the supernatant. The culture supernatant containing the active protein(s) can be used in bioassays.

Alternatively, a subculture of Bacillus isolates, or mutants thereof, can be used to inoculate the following peptone, glucose, salts medium:

| Bacto Peptone | 7.5 g/l |
|---|---|
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| pH 7.2 | |
| Salts Solution (100 ml) | |
| $MgSO_4 \cdot 7H_2O$ | 2.46 g |
| $MnSO_4 \cdot H_2O$ | 0.04 g |
| $ZnSO_4 \cdot 7H_2O$ | 0.28 g |
| $FeSO_4 \cdot 7H_2O$ | 0.40 g |
| $CaCl_2$ Solution (100 ml) | |
| $CaCl_2 \cdot 2H_2O$ | 3.66 g |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The Bacillus spores and/or crystals, obtained in the above fermentation, can be isolated by procedures well known in the art. A frequently-used procedure is to subject the harvested fermentation broth to separation techniques, e.g., centrifugation.

EXAMPLE 2

Isolation and Preparation of Cellular DNA for PCR

DNA can be prepared from cells grown on Spizizen's agar, or other minimal or enriched agar known to those skilled in the art, for approximately 16 hours. Spizizen's casamino acid agar comprises 23.2 g/l Spizizen's minimal salts [$(NH_4)_2SO_4$, 120 g; $K_2HPO_4$, 840 g; $KH_2PO_4$, 360 g; sodium citrate, 60 g; $MgSO_4 \cdot 7H_2O$, 12 g. Total: 1392 g]; 1.0 g/l vitamin-free casamino acids; 15.0 g/l Difco agar. In preparing the agar, the mixture was autoclaved for 30 minutes, then a sterile, 50% glucose solution can be added to a final concentration of 0.5% (1/100 vol). Once the cells are grown for about 16 hours, an approximately 1 $cm^2$ patch of cells can be scraped from the agar into 300 µl of 10 mM Tris-HCl (pH 8.0)-1 mM EDTA. Proteinase K was added to 50 µg/ml and incubated at 55° C. for 15 minutes. Other suitable proteases lacking nuclease activity can be used. The samples were then placed in a boiling water bath for 15 minutes to inactivate the proteinase and denature the DNA. This also precipitates unwanted components. The samples are then centrifuged at 14,000×g in an Eppendorf microfuge at room temperature for 5 minutes to remove cellular debris. The supernatants containing crude DNA were transferred to fresh tubes and frozen at −20° C. until used in PCR reactions.

Alternatively, total cellular DNA may be prepared from plate-grown cells using the QIAamp Tissue Kit from Qiagen (Santa Clarita, Calif.) following instructions from the manufacturer.

EXAMPLE 3

Use of PCR Primers to Characterize and/or Identify Toxin Genes

Two primers useful in PCR procedures were designed to identify genes that encode pesticidal toxins. Preferably, these toxins are active against lepidopteran insects. The DNA from 95 B.t. strains was subjected to PCR using these primers. Two clearly distinguishable molecular weight bands were visible in "positive" strains, as outlined below. The frequency of strains yielding a 339 bp fragment was 29/95 (31%). This fragment is referred to herein as the "339 bp fragment" even though some small deviation in the exact number of base pairs may be observed.

GARCCRTGGA AAGCAAATAA TAARAATGC (SEQ ID NO. 1)

AAARTTATCT CCCCAWGCTT CATCTCCATT TTG (SEQ ID NO. 2)

The strains which were positive for the 339 bp fragment (29 strains) were: PS11 B, PS31G1,PS36A, PS49C, PS81A2, PS81F, PS81GG, PS81I, PS85A1, PS86BB1, PS86V1, PS86W1, PS89J3, PS91C2, PS94R1, PS101DD, PS158C2, PS185U2, PS192M4, PS202S, PS213E5, PS218G2, PS244A2, HD29, HD110, HD129, HD525, HD573a, and Javelin 1990.

The 24 strains which gave a larger (approximately 1.2 kb) fragment were: PS24J, PS33F2, PS45B1, PS52A1, PS62B1, PS80PP3, PS86A1, PS86Q3, PS88F16, PS92B, PS101Z2, PS123D1, PS157C1, PS169E, PS177F1, PS177G, PS185L2,PS201L1, PS204C3, PS204G4, PS242H10, PS242K17, PS244A2, PS244D1.

It was found that Bacillus strains producing lepidopteran-active proteins yielded only the 339 bp fragment. Few, if any, of the strains amplifying the approximately 1.2 kb fragment had known lepidopteran activity, but rather were coleopteran-, mite-, and/or nematode-active B.t. crystal protein producing strains.

EXAMPLE 4

DNA Sequencing of Toxin Genes Producing the 339 Fragment

PCR-amplified segments of toxin genes present in Bacillus strains can be readily sequenced. To accomplish this, amplified DNA fragments can be first cloned into the PCR DNA TA-cloning plasmid vector, pCRII, as described by the supplier (Invitrogen, San Diego, Calif.). Individual pCRII clones from the mixture of amplified DNA fragments from each Bacillus strain are chosen for sequencing. Colonies are lysed by boiling to release crude plasmid DNA. DNA templates for automated sequencing are amplified by PCR using vector-specific primers flanking the plasmid multiple cloning sites. These DNA templates are sequenced using Applied Biosystems (Foster City, Calif.) automated sequencing methodologies. The polypeptide sequences can be deduced from these nucleotide sequences.

DNA from three of the 29 B.t. strains which amplified the 339 bp fragments were sequenced. A DNA sequence encoding a toxin from strain PS36A is shown in SEQ ID NO. 3. An amino acid sequence for the 36A toxin is shown in SEQ ID. NO 4. A DNA sequence encoding a toxin from strain PS81F is shown in SEQ ID NO. 5. An amino acid sequence for the 81F toxin is shown in SEQ ID. NO 6. A DNA sequence encoding a toxin from strain Javelin 1990 is shown in SEQ ID NO. 7. An amino acid sequence for the Javelin 1990 toxin is shown in SEQ ID. NO 8.

EXAMPLE 5

Determination of DNA Sequences from Additional Genes Encoding Toxins from Strains PS158C2 and PS49C Genes encoding novel toxins were identified from isolates PS158C2 and PS49C as follows: Total cellular DNA was extracted from B.t. strains using Qiagen (Santa Clarita, Calif.) Genomic-tip 500/G DNA extraction kits according to the supplier and was subjected to PCR using the oligonucleotide primer pairs listed below. Amplified DNA fragments were purified on Qiagen PCR purification columns and were used as templates for sequencing.

For PS158C2, the primers used were as follows.
158C2 PRIMER A:
  GCTCTAGAAGGAGGTAACTTATGAACAA-GAATAATACTAAATTAAGC (SEQ ID NO. 9)
339 reverse:
  AAARTTATCT CCCCAWGCTT CATCTCCATT TTG (SEQ ID NO. 2)

The resulting PCR-amplified DNA fragment was approximately 2 kbp in size. This DNA was partially sequenced by dideoxy chain termination using automated DNA sequencing technology (Pekin Elmer/Applied Biosystems, Foster City, Calif.). A DNA sequence encoding a portion of a soluble toxin from PS158C2 is shown in SEQ ID NO. 10.

For PS49C, two separate DNA fragments encoding parts of a novel toxin gene were amplified and sequenced. The first fragment was amplified using the following primer pair:
49C PRIMER A:
  CATCCTCCCTACACTTTCTAA (SEQ ID NO. 11)
339 reverse:
  AAARTTATCT CCCCAWGCTT CATCTCCATT TTG (SEQ ID NO. 2)

The resulting approximately 1 kbp DNA fragment was used as a template for automated DNA sequence. A sequence of a portion of a toxin gene from strain PS49C is shown in SEQ ID NO. 12.

The second fragment was amplified using the following primer pair:
49C PRIMER B:
  AAATTATGCGCTAAGTCTGC (SEQ ID NO. 13)
49C PRIMER C:
  TTGATCCGGACATAATAAT (SEQ ID NO. 14)

The resulting approximately 0.57 kbp DNA fragment was used as a template for automated DNA sequencing. An additional sequence of a portion of the toxin gene from PS49C is shown in SEQ ID NO. 15.

EXAMPLE 6

Additional Primers Useful for Characterizing and/or Identifying Toxin Genes

The following primer pair can be used to identify and/or characterize genes of the SUP-1 family:
SUP-1A:
  GGATTCGTTATCAGAAA (SEQ ID NO. 53)
SUP-1B:
  CTGTYGCTAACAATGTC (SEQ ID NO. 54)

These primers can be used in PCR procedures to amplify a fragment having a predicted size of approximately 370 bp. A band of the predicted size was amplified from strains PS158C2 and PS49C.

EXAMPLE 7

Additional Primers Useful for Characterizing and/or Identifying Toxin Genes

Another set of PCR primers can be used to identify and/or characterize additional genes encoding pesticidal toxins. The sequences of these primers were as follows:
  GGRTTAMTTGGRTAYTATTT (SEQ ID NO. 16)
  ATATCKWAYATTKGCATTTA (SEQ ID NO. 17)

Redundant nucleotide codes used throughout the subject disclosure are in accordance with the IUPAC convention and include:
  R=A or G
  M=A or C
  Y=C or T
  K=G or T
  W=A or T

EXAMPLE 8

Identification and Sequencing of Genes Encoding Novel Soluble Protein Toxins from Bacillus Strains PCR using primers SEQ ID NO. 16 and SEQ ID NO. 17 was performed on total cellular genomic DNA isolated from a broad range of Bt strains. Those samples yielding an approximately 1 kb band were selected for characterization by DNA sequencing. Amplified DNA fragments were first cloned into the PCR DNA TA-cloning plasmid vector, pCR2. 1, as described by the supplier (Invitrogen, San Diego, Calif.). Plasmids were isolated from recombinant clones and tested for the presence of an approximately 1 kbp insert by PCR using the plasmid vector primers, T3 and T7.

The following strains yielded the expected band of approximately 1000 bp, thus indicating the presence of a MIS-type toxin gene: PS10E1, PS31J2, PS33D2, PS66D3, PS68F, PS69AA2, PS168G1, PS177C8, PS177I8, PS185AA2, PS196F3, PS196J4, PS197T1, PS197U2, PS202E1, KB33, and KB38.

Plasmids were then isolated for use as sequencing templates using QIAGEN (Santa Clarita, Calif.) miniprep kits as described by the supplier. Sequencing reactions were performed using the Dye TerminatorCycle Sequencing Ready Reaction Kit from PE Applied Biosystems. Sequencing reactions were run on a ABI PRISM 377 Automated Sequencer. Sequence data was collected, edited, and assembled using the ABI PRISM 377 Collection, Factura, and AutoAssembler software from PE ABI.

DNA sequences were determined for portions of novel toxin genes from the following isolates: PS10E1, PS31J2, PS33D2, PS66D3, PS68F, PS69AA2, PS168G1, PS177C8, PS177I8, PS185AA2, PS196F3, PS196J4, PS197T1, PS197U2, PS202E1, and KB38. Polypeptide sequences were deduced for portions of the encoded, novel soluble toxins from the following isolates: PS10E1, PS31J2, PS33D2, PS66D3, PS68F, PS69AA2, PS177C8, PS177I8, PS185AA2, PS196F3, PS196J4, PS197T1, PS197U2, and PS202E1. These nucleotide sequences and amino acid sequences are shown in SEQ ID NOS. 18 to 48.

EXAMPLE 9

Restriction Fragment Lenga Polymorphism (RFLP) of Toxins from Bacillus thuringiensis Strains Total cellular DNA was prepared from various Bacillus thuriengensis (B.t.) strains grown to an optical density of 0.5–0.8 at 600 nm visible light. DNA was extracted using the Qiagen Genomic-tip 500/G kit and Genomic DNA Buffer Set according to protocol for Gram positive bacteria (Qiagen Inc.; Valencia, Calif.).

Standard Southern hybridizations using $^{32}$P-lableled probes were used to identify and characterize novel toxin genes within the total genomic DNA preparations. Prepared total genomic DNA was digested with various restriction enzymes, electrophoresed on a 1% agarose gel, and immobilized on a supported nylon membrane using standard methods (Maniatis et al.).

PCR-amplified DNA fragments 1.0–1.1 kb in length were gel purified for use as probes. Approximately 25 ng of each DNA fragment was used as a template for priming nascent DNA synthesis using DNA polymerase I Klenow fragment (New England Biolabs), random hexanucleotide primers (Boehringer Mannheim) and $^{32}$PdCTP.

Each $^{32}$P-lableled fragment served as a specific probe to its corresponding genomic DNA blot. Hybridizations of immobilized DNA with randomly labeled $^{32}$P probes were performed in standard aqueous buffer consisting of 5× SSPE, 5× Denhardt's solution, 0.5% SDS, 0.1 mg/ml at 65° C. overnight. Blots were washed under moderate stringency in 0.2× SSC, 0.1% SDS at 65° C. and exposed to film. RFLP data showing specific hybridization bands containing all or part of the novel gene of interest was obtained for each strain.

| (Strain)/ Gene Name | Probe Seq I.D. Number | RFLP Data (approximate band sizes) |
|---|---|---|
| (PS)10E1* | 18 | EcoRI: 4 and 9 kbp, EcoRV: 4.5 and 6 kbp, KpnI: 12 and 24 kbp, SacI: 13 and 24 kbp, SalI: >23 kbp, XbaI: 5 and 15 kbp |
| (PS)31J2 | 20 | ApaI: >23 kbp, BglII: 6.5 kbp, PstI: >23 kbp, SacI: >23 kbp, SalI: >23 kbp, XbaI: 5 kbp |
| (PS)33D2 | 22 | EcoRI: 10 kbp, EcoRV: 15 kbp, HindIII: 18 kbp, KpnI: 9.5 kbp, PstI: 8 kbp |
| (PS)66D3 | 24 | BamHI: 4.5 kbp, HindIII: >23 kbp, KpnI: 23 kbp, PstI: 15 kbp, XbaI: >23 kbp |
| (PS)68F* | 26 | EcoRI: 8.5 and 15 kbp, EcoRV: 7 and 18 kbp, HindIII: 2.1 and 9.5 kbp, PstI: 3 and 18 kbp, XbaI: 10 and 15 kbp |
| (PS)69AA2 | 28 | EcoRV: 9.5 kbp, HindIII: 18 kbp, KpnI: 23 kbp, NheI: >23 kbp, PstI: 10 kbp, SalI: >23 kbp |
| (PS)168G1 | 30 | EcoRI: 10 kbp, EcoRV: 3.5 kbp, NheI: 20 kbp, PstI: 20 kbp, SalI: >23 kbp, XbaI: 15 kbp |
| (PS)177C8 | 31 | HindIII: 2 kbp, Xbal: 1, 9 and 11 kbp |
| (PS)17718 | 33 | BamHI: >23 kbp, EcoRI: 10 kbp, HindIII: 2 kbp, SalI: >23 kbp, XbaI:3.5 kbp |
| (PS)185AA2 | 35 | EcoRI: 7 kbp, EcoRV: 10 kbp (&3.5kbp?), NheI: 4 kbp, PstI: 3 kbp, SalI: >23 kbp, XbaI: 4 kbp |
| (PS)196F3 | 37 | EcoRI: 8 kbp, ECoRV: 9 kbp, NheI: 18 kbp, PstI: 18 kbp, SalI: 20 kbp, XbaI: 7 kbp |
| (PS)196J4* | 39 | BamHI: >23 kbp, EcoRI: 3.5 and 4.5 kbp, PstI: 9 and 24 kbp, SalI: >23 kbp, XbaI: 2.4 and 12 kbp |
| (PS)197T1 | 41 | HindIII: 10 kbp, KpnI: 20 kbp, PstI: 20 kbp, SacI: 20 kbp, SpeI: 15 kbp, XbaI: 5 kbp |
| (PS)197U2 | 43 | EcoRI: 5 kbp, EcoRV: 1.9 kbp, NheI: 20 kbp, PstI: 23 kbp, SalI: >23 kbp, XbaI: 7 kbp |
| (PS)202E1 | 45 | EcoRV: 7 kbp, KpnI: 12 kbp, NheI: 10 kbp, PstI: 15 kbp, SalI: 23 kbp, XbaI: 1.8 kbp |
| KB33 | 47 | EcoRI: 9 kbp, EcoRV: 6 kbp, HindIII: 8 kbp, KpnI: >23 kbp, NheI: 22 kbp, SalI: >23 kbp |
| KB38 | 48 | BamHI: 5.5 kbp, EcoRV: 22 kbp, HindIII: 2.2 kbp, NheI: 20 kbp, PstI: >23 kbp |

*Enzymes used in genomic DNA digests were chosen on the basis of lacking recognition sites within the sequence of the PCR fragments used as probes for each sample (except 177C8 for which the entire operon containing >1 XbaI site within the sequence was used). Strains indicated by asterisk contain more than one gene with high homology to the probe used, as indicated by the presence of multiple hybridizing bands.

EXAMPLE 10

Use of Additional PCR Primers for Characterizing and/or Identifying Novel Genes Another set of PCR primers can be used to identify additional novel genes encoding pesticidal toxins. The sequences of these primers were as follows:

ICON-forward:
CTTGAYTTTAAARATGATRTA (SEQ ID NO. 49)

ICON-reverse:
AATRGCSWATAAATAMGCACC (SEQ ID NO. 50)

These primers can be used in PCR procedures to amplify a fragment having a predicted size of about 450 bp.

Strains PS177C8, PS177I8, and PS66D3 were screened and were found to have genes amplifiable with these ICON primers. A sequence of a toxin gene from PS177C8 is shown in SEQ ID NO. 51. An amino acid sequence of the 177C8-ICON toxin is shown in SEQ ID NO. 52.

EXAMPLE 11

Use of Mixed Primer Pairs to Characterize and/or Identify Toxin Genes

Various combinations of the primers described herein can be used to identify and/or characterize toxin genes. PCR conditions can be used as indicated below:

|  | SEQ ID NO. 16/17 | SEQ ID NO. 49/50 | SEQ ID NO. 49/17 |
|---|---|---|---|
| Pre-denature | 94° C. 1 min. | 94° C. 1 min. | 94° C. 1 min. |
| Program | 94° C. 1 min. | 94° C. 1 min. | 94° C. 1 min. |
| Cycle | 42° C. 2 min. | 42° C. 2 min. | 42° C. 2 min. |
|  | 72° C. 3 min. + 5 sec/cycl | 72° C. 3 min. + 5 sec/cycl | 72° C. 3 min. + 5 sec/cycl |
|  | Repeat cycle 29 times | Repeat cycle 29 times | Repeat cycle 29 times |
|  | Hold 4° C. | Hold 4° C. | Hold 4° C. |

Using the above protocol, a strain harboring a MIS-type of toxin would be expected to yield a 1000 bp fragment with the SEQ ID NO. 16/17 primer pair. A strain harboring a WAR-type of toxin would be expected to amplify a fragment of about 475 bp with the SEQ ID NO. 49/50 primer pair, or a fragment of about 1800 bp with the SEQ ID NO. 49/17 primer pair. The amplified fragments of the expected size were found in four strains. The results are reported in Table 3.

TABLE 3

Approximate Amplified Fragment Sizes (bp)

| Strain | SEQ ID NO. 16/17 | SEQ ID NO. 49/50 | SEQ ID NO. 49/17 |
|---|---|---|---|
| PS66D3 | 1000 | 900, 475 | 1800 |
| PS177C8 | 1000 | 475 | 1800 |
| PS177I8 | 1000 | 900, 550, 475 | 1800 |
| PS217U2 | 1000 | 2500, 1500, 900, 475 | no band detected |

EXAMPLE 12

Characterization and/or Identification of WAR Toxins

In a further embodiment of the subject invention, pesticidal toxins can be characterized and/or identified by their level of reactivity with antibodies to pesticidal toxins exemplified herein. In a specific embodiment, antibodies can be raised to WAR toxins such as the toxin obtainable from PS177C8a. Other WAR toxins can then be identified and/or characterized by their reactivity with the antibodies. In a preferred embodiment, the antibodies are polyclonal antibodies. In this example, toxins with the greatest similarity to the 177C8a-WAR toxin would have the greatest reactivity with the polyclonal antibodies. WAR toxins with greater diversity react with the 177C8a polyclonal antibodies, but to a lesser extent. Toxins which immunoreact with polyclonal antibodies raised to the 177C8a WAR toxin can be obtained from, for example, the isolates designated PS177C8a, PS177I8, PS66D3, KB68B55-2, PS185Y2, PS146F, KB53A49-4, PS175I4, KB68B51-2, PS28K1, PS31F2, KB58B46-2, and PS146D. Such diverse WAR toxins can be further characterized by, for example, whether or not their genes can be amplified with ICON primers. For example, the following isolates do not have polynucleotide sequences which are amplified by ICON primers: PS177C8a, PS177I8, PS66D3, KB68B55-2, PS185Y2, PS146F, KB53A49-4, PS175I4, KB68B51-2, PS28K1, PS31F2, KB58B46-2, and PS146D. Of these, isolates PS28K1, PS31F2, KB68B46-2, and PS146D show the weakest antibody reactivity, suggesting advantageous diversity.

EXAMPLE 13

Bioassays for Activity Against Lepidopterans and Coleopterans

Biological activity of the toxins and isolates of the subject invention can be confined using standard bioassay procedures. One such assay is the budworm-bollworm (*Heliothis virescens* [Fabricius] and *Helicoverpa zea* [Boddie]) assay. Lepidoptera bioassays were conducted with either surface application to artificial insect diet or diet incorporation of samples. All Lepidopteran insects were tested from the neonate stage to the second instar. All assays were conducted with either toasted soy flour artificial diet or black cutworm artificial diet (BioServ, Frenchtown, N.J.).

Diet incorporation can be conducted by mixing the samples with artificial diet at a rate of 6 mL suspension plus 54 mL diet. After vortexing, this mixture is poured into plastic trays with compartmentalized 3-ml wells (Nutrend Container Corporation, Jacksonville, Fla.). A water blank containing no B.t. serves as the control. First instar larvae (USDA-ARS, Stoneville, Miss.) are placed onto the diet mixture. Wells are then sealed with Mylar sheeting (ClearLam Packaging, IL) using a tacking iron, and several pinholes are made in each well to provide gas exchange. Larvae were held at 25° C. for 6 days in a 14:10 (light:dark) holding room. Mortality and stunting are recorded after six days.

Bioassay by the top load method utilizes the same sample and diet preparations as listed above. The samples are applied to the surface of the insect diet. In a specific embodiment, surface area ranged from 0.3 to approximately 0.8 $cm^2$ depending on the tray size, 96 well tissue culture plates were used in addition to the format listed above. Following application, samples are allowed to air dry before insect infestation. A water blank containing no B.t. can serve as the control. Eggs are applied to each treated well and were then sealed with Mylar sheeting (ClearLam Packaging, IL) using a tacking iron, and pinholes are made in each well to provide gas exchange. Bioassays are held at 25° C. for 7 days in a 14:10 (light:dark) or 28° C. for 4 days in a 14:10 (light:dark) holding room. Mortality and insect stunting are recorded at the end of each bioassay.

Another assay useful according to the subject invention is the Western corn rootworm assay. Samples can be bioassayed against neonate western corn rootworm larvae (*Diabrotica virgifera virgifera*) via top-loading of sample onto an agar-based artificial diet at a rate of 160 ml/$cm^2$. Artificial diet can be dispensed into 0.78 $cm^2$ wells in 48-well tissue culture or similar plates and allowed to harden. After the diet solidifies, samples are dispensed by pipette onto the diet surface. Excess liquid is then evaporated from the surface prior to transferring approximately three neonate larvae per well onto the diet surface by camel's hair brush. To prevent insect escape while allowing gas exchange, wells are heat-sealed with 2 mil punched polyester film with 27HT adhesive (Oliver Products Company, Grand Rapids, Mich.). Bioassays are held in darkness at 25° C., and mortality scored after four days.

Analogous bioassays can be performed by those skilled in the art to assess activity against other pests, such as the black cutworm (*Agrotis epsilon*).

Results are shown in Table 4.

TABLE 4

Genetics and function of concentrated B.t. supernatants screened for lepidopteran and coleopteran activity

| Strain | Approx. 339 bp PCR fragment | Total Protein ($\mu g/cm^2$) | ca. 80–100 kDa protein ($\mu g/cm^2$) | H. virescens % mortality | Stunting | H. zen % mortality | Stunting | Diabrotica % mortality |
|---|---|---|---|---|---|---|---|---|
| PS31G1 | + | 8.3 | 2.1 | 70 | yes | 39 | yes | NT |
| PS49C | + | 13.6 | 1.5 | 8 | yes | 8 | no | NT |
| PS80JJ1 | – | 8.0 | NT | 18 | no | 13 | no | NT |
| PS80JJ1 (#2) | – | 3.5 | NT | — | — | — | — | 43 |
| PS81A2 (#1) | + | 30.3 | 2.3 | 100 | yes | 38 | yes | NT |
| PS81A2 (#2) | + | 18.8 | 1.6 | 38 | yes | 13 | no | NT |
| PS81F | ++ | 26 | 5.2 | 100 | yes | 92 | yes | NT |
| PS81I | + | 10.7 | 1.7 | 48 | yes | 13 | no | NT |
| PS86B1 (#1) | – | 23.2 | 4.5 | 17 | no | 13 | no | — |
| PS86B1 (#2) | – | 90 | 17.5 | — | — | — | — | 35 |
| PS86B1 (#3) | – | 35 | 6.8 | — | — | — | — | 10 |
| PS122D3 (#1) | – | 33.2 | 1.8 | 21 | no | 21 | No | — |
| PS122D3 (#2) | – | 124 | 6.7 | — | — | — | — | 45 |
| PS122D3 (#3) | – | 35 | 1.9 | — | — | — | — | 16 |
| PS123D1 (#1) | – | 10.7 | NT | 0 | no | 0 | no | — |
| PS123D1 (#2) | – | 69 | NT | — | — | — | — | 54 |
| PS123D1 (#3) | – | 35 | NT | — | — | — | — | 21 |
| PS123D1 (#4) | – | 17.8 | NT | 5 | no | 4 | no | NT |
| PS149B1 (#1) | NT | 9 | NT | 0 | no | 0 | yes | NT |
| PS149B1 (#2) | NT | 35 | NT | — | — | — | — | 50 |
| PS157C1 (#1) | – | 24 | 2 | 43 | yes | 13 | yes | — |
| PS157C1 (#2) | – | 93 | 8 | — | — | — | — | 40 |
| PS157C1 (#3) | – | 35 | 3 | — | — | — | — | 18 |
| PS185L2 (#1) | – | 2 | NT | 8 | no | 0 | no | NT |
| PS185L2 (#2) | – | 3 | NT | 10 | no | 25 | no | NT |
| PS185U2 | + | 23.4 | 2.9 | 100 | yes | 100 | yes | NT |
| PS192M4 | + | 10.7 | 2.0 | 9 | no | 4 | yes | NT |
| HD129 | + | 44.4 | 4.9 | 100 | yes | 50 | yes | NT |
| Javelin 1990 | ++ | 43.2 | 3.6 | 100 | yes | 96 | yes | NT |
| water | | | | 0–8 | — | 0–4 | — | 12 |

*NT = not tested

EXAMPLE 14
Results of Western Corn Rootworm Bioassays

Concentrated liquid supernatant solutions, obtained according to the subject invention, were tested for activity against Western corn rootworm (WCRW). Supernatants from the following isolates were found to cause mortality against WCRW: PS10E1, PS31F2, PS31J2, PS33D2, PS66D3, PS68F, PS80JJ1, PS146D, PS175I4, PS177I8, PS196J4, PS197T1, PS197U2, KB33, KB53A49-4, KB68B46-2, KB68B51-2, KB68B55, PS177C2, PS69AA2, KB38, PS196F3, PS168G1, PS202E1, PS217U2 and PS185AA2.

EXAMPLE 15
Results of Budworm/Bollworm Bioassays

Concentrated liquid supernatant solutions, obtained according to the subject invention, were tested for activity against *Heliothis virescens* (*H.v.*) and *Helicoverpa zea* (*H.z.*). Supernatants from the following isolates were tested and were found to cause mortality against *H.v.*: PS157C1, PS31G1, PS49C, PS81F, PS81I, Javelin 1990, PS158C2, PS202S, PS36A, HD110, and HD29. Supernatants from the following isolates were tested are were found to cause significant mortality against *H.z.*: PS31G1, PS49C, PS81F, PS81I, PS157C1, PS158C2, PS36A, HD110, and Javelin 1990.

EXAMPLE 16
Target Pests

Toxins of the subject invention can be used, alone or in combination with other toxins, to control one or more non-mammalian pests. These pests may be, for example, those listed in Table 5. Activity can readily be confirmed using the bioassays provided herein, adaptations of these bioassays, and/or other bioassays well known to those skilled in the art.

TABLE 5

Target pest species

| ORDER/Common Name | Latin Name |
|---|---|
| LEPIDOPTERA | |
| European Corn Borer | *Ostrinia nubilalis* |
| European Corn Borer resistant to Cry1Ab | *Ostrinia nubilalis* |
| Black Cutworm | *Agrotis ipsilon* |
| Fall Armyworm | *Spodoptera frugiperda* |
| Southwestern Corn Borer | *Diatraea grandiosella* |
| Corn Earworm/Bollworm | *Helicoverpa zea* |
| Tobacco Budworm | *Heliothis virescens* |
| Tobacco Budworm Rs | *Heliothis virescens* |
| Sunflower Head Moth | *Homeosoma ellectellum* |
| Banded Sunflower Moth | *Cochylis hospes* |
| Argentine Looper | *Rachiplusia nu* |
| Spilosoma | *Spilosoma virginica* |
| Bertha Armyworm | *Mamestra configurata* |
| Diamondback Moth | *Plutella xylostells* |
| COLEOPTERA | |
| Red Sunflower Seed Weevil | *Smicronyx fulvus* |
| Sunflower Stem Weevil | *Cylindrocopturus adspersus* |
| Sunflower Beetle | *Zygoramma exclamationis* |
| Canola Flea Beetle | *Phyllotreta cruciferae* |
| Western Corn Rootworm | *Diabrotica virgifera virgifera* |

TABLE 5-continued

| Target pest species | |
|---|---|
| ORDER/Common Name | Latin Name |
| DIPTERA | |
| Hessian Fly | *Mayetiola destructor* |
| HOMOPTERA | |
| Greenbug | *Schizaphis graminum* |
| HEMIPTERA | |
| Lygus Bug | *Lygus lineolaris* |
| NEMATODA | *Heterodera glycines* |

EXAMPLE 17

Insertion of Toxin Genes Into Plants

One aspect of the subject invention is the transformation of plants with genes encoding the insecticidal toxin of the present invention. The transformed plants are resistant to attack by the target pest.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the Bacillus toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978] *Mol. Gen. Genet.* 163:181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives. In biolistic transformation, plasmid DNA or linear DNA can be employed.

The transformed cells are regenerated into morphologically normal plants in the usual manner. If a transformation event involves a germ line cell, then the inserted DNA and corresponding phenotypic trait(s) will be transmitted to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831. Also, advantageously, plants encoding a truncated toxin will be used. The truncated toxin typically will encode about 55% to about 80% of the full length toxin. Methods for creating synthetic Bacillus genes for use in plants are known in the art.

It should be understood that the examples and embodiments described herein are for illustrative purposes only and that various modifications or changes in light thereof will be suggested to persons skilled in the art and are to be included within the spirit and purview of this application.

What is claimed is:

1. An isolated polynucleotide which encodes a pesticidally active protein wherein said polynucleotide hybridizes under conditions of 0.1× SSPE at 65° C. with the full complement of a nucleotide sequence selected from the group consisting of SEQ ID NO. 18, SEQ ID NO. 22, SEQ ID NO. 26, and SEQ ID NO. 47.

2. An isolated polynucleotide which encodes a pesticidally active protein wherein said polynucleotide comprises the nucleotide sequence of SEQ ID NO. 10.

3. An isolated polynucleotide which encodes a pesticidlly active protein wherein said polynucleotide comprises the nucleotide sequence of SEQ ID NO. 12.

4. The polynucleotide of claim 1, wherein said nucleotide sequence is SEQ ID NO. 18.

5. The polynucleotide of claim 1 wherein said nucleotide sequence is SEQ ID NO. 22.

6. The polynucleotide of claim 1 wherein said nucleotide sequence is SEQ ID NO. 26.

7. The polynucleotide of claim 1 wherein said nucleotide sequence is SEQ ID NO. 47.

8. An isolated polynucleotide which encodes a pesticidally active protein wherein said protein comprises an amino acid sequence selected from the group consisting of SEQ ID NO. 19, SEQ ID NO. 23, SEQ ID NO. 27, and SEQ ID NO. 44.

9. The polynucleotide of claim 8 wherein said amino acid sequcence is SEQ ID NO. 19.

10. The polynucleotide of claim 8 wherein said amino acid sequence is SEQ ID NO. 23.

11. The polynucleotide of claim 8 wherein said amino acid sequence is SEQ ID NO. 27.

12. The polynuclcotide of claim 8 wherein said amino acid sequence is SEQ ID NO. 44.

13. A recombinant host comprising an isolated polynucleotide which encodes a pesticidally active protein, wherein said host is a plant, and wherein said polynucleotide hybridizes under conditions of 0.1× SSPE at 65° C. with the full complement of a nucleotide sequence selected from the group consisting of SEQ ID NO. 18, SEQ ID NO. 22, SEQ ID NO. 26, and SEQ ID NO. 47.

14. A recombinant host comprising an isolated polynucleotide which encodes a pesticidally active protein, wherein said host is a plant, and wherein said polynucleotide comprises the nucleotide sequence of SEQ ID NO. 10.

15. A recombinant host comprising an isolated polynucleotide which encodes a pesticidally active protein, wherein said host is a plant, and wherein said polynucleotide comprises the nucleotide sequence of SEQ ID NO. 12.

16. The recombinant host of claim 13 wherein said nucleotide sequence is SEQ ID NO. 18.

17. The recombinant host of claim 13 wherein said nuelcotide sequence is SEQ ID NO. 22.

18. The recombinant host of claim 13 wherein said nucleotide sequence is SEQ ID NO. 26.

19. The recombinant host of claim 13 wherein said nucleotide sequence is SEQ ID NO. 47.

20. A recombinant host comprising a polynucleotide sequence which encodes a pesticidally active protein, wherein said host is a plant, and wherein said protein comprises an amino acid sequence selected from the group consisting of SEQ ID NO. 19, SEQ ID NO. 23, SEQ ID NO. 27, and SEQ ID NO. 44.

21. The recombinant host of claim 20 wherein said amino acid sequence is SEQ ID NO. 19.

22. The recombinant host of claim 20 wherein said amino acid sequence is SEQ ID NO. 23.

23. The recombinant host of claim 20 wherein said amino acid sequence is SEQ ID NO. 27.

24. The recombinant host of claim 20 wherein said amino acid sequence is SEQ ID NO. 44.

25. A recombinant host comprising an isolated polynucleotide which encodes a pesticidally active protein, wherein said host is a plant cell, and wherein said polynucleotide hybridizes under conditions of 0.1× SSPE at 65° C. with the full complement of a nucleotide sequence selected from the group consisting of SEQ ID NO:18, SEQ ID NO:22, SEQ ID NO:26, and SEQ ID NO:47.

26. A recombinant host comprising an isolated polynucleotide which encodes a pesticidally active protein, wherein said host is a microbial cell, and wherein said polynucleotide hybridizes under conditions of 0.1× SSPE at 65° C. with the full complement of a nucleotide sequence selected from the group consisting of SEQ ID NO:18, SEQ ID NO:22, SEQ ID NO:26, and SEQ ID NO:47.

27. The recombinant host of claim 25 wherein said nucleotide sequence is SEQ ID NO:18.

28. The recombinant host of claim 25 wherein said nucleotide sequence is SEQ ID NO:22.

29. The recombinant host of claim 25 wherein said nucleotide sequence is SEQ ID NO:26.

30. The recombinant host of claim 25 wherein said nucleotide sequence is SEQ ID NO:47.

31. The recombinant host of claim 26 wherein said nucleotide sequence is SEQ ID NO:18.

32. The recombinant host of claim 26 wherein said nucleotide sequence is SEQ ID NO:22.

33. The recombinant host of claim 26 wherein said nucleotide sequence is SEQ ID NO:26.

34. The recombinant host of claim 26 wherein said nucleotide sequence is SEQ ID NO:47.

35. A recombinant host comprising an isolated polynucleotide which encodes a pesticidally active protein, wherein said host is a plant cell, and wherein said polynucleotide comprises the nucleotide sequence of SEQ ID NO:10.

36. A recombinant host comprising an isolated polynucleotide which encodes a pesticidally active protein, wherein said host is a microbial cell, and wherein said polynucleotide comprises the nucleotide sequence of SEQ ID NO:10.

37. A recombinant host comprising an isolated polynucleotide which encodes a pesticidally active protein, wherein said host is a plant cell, and wherein said polynucleotide comprises the nucleotide sequence of SEQ ID NO:12.

38. A recombinant host comprising an isolated polynucleotide which encodes a pesticidally active protein, wherein said host is a microbial cell, and wherein said polynucleotide comprises the nucleotide sequence of SEQ ID NO:12.

39. A recombinant host comprising a polynucleotide sequence which encodes a pesticidally active protein, wherein said host is a plant cell, and wherein said protein comprises an amino acid sequence selected from the group consisting of SEQ ID NO:19, SEQ ID NO:23, SEQ ID NO:27, and SEQ ID NO:44.

40. The recombinant host of claim 39 wherein said amino acid sequence is SEQ ID NO:19.

41. The recombinant host of claim 39 wherein said amino acid sequence is SEQ ID NO:23.

42. The recombinant host of claim 39 wherein said amino acid sequence is SEQ ID NO:27.

43. The recombinant host of claim 39 wherein said amino acid sequence is SEQ ID NO:44.

44. A recombinant host comprising a polynucleotide sequence which encodes a pesticidally active protein, wherein said host is a microbial cell, and wherein said protein comprises an amino acid sequence selected from the group consisting of SEQ ID NO:19, SEQ ID NO:23, SEQ ID NO:27, and SEQ ID NO:44.

45. The recombinant host of claim 44 wherein said amino acid sequence is SEQ ID NO:19.

46. The recombinant host of claim 44 wherein said amino acid sequence is SEQ ID NO:23.

47. The recombinant host of claim 44 wherein said amino acid sequence is SEQ ID NO:27.

48. The recombinant host of claim 44 wherein said amino acid sequence is SEQ ID NO:44.

* * * * *

UNITED STATES PATENT AND TRADEMARK OFFICE
CERTIFICATE OF CORRECTION

PATENT NO.    : 6,204,435 B1
DATED         : March 20, 2001
INVENTOR(S)   : Feitelson et al.

It is certified that error appears in the above-identified patent and that said Letters Patent is hereby corrected as shown below:

Column 2,
Line 7, "FEBSLett." should read -- FEBS Lett. --.

Column 3,
Line 33, "MIS-4,MIS-5,MIS-6," should read -- MIS-4, MIS-5, MIS-6, --.

Column 4,
Line 37, "toxin" should read -- toxin. --.

Column 6,
Line 57, "108." should read -- 110. --.

Column 7,
Lines 3-4, "recombinanthosts" should read -- recombinant hosts --.
Line 28, "NRRL B-18450" should read -- NRRL B-18457 --.
Line 55, "25439" should read -- 21539 --.
Line 58, "March1 4, 1996" should read -- March 14, 1996 --.

Column 8,
Line 48, "subjectculture" should read -- subject culture --.

Column 9,
Line 15, "providedherein" should read -- provided herein --.
Lines 18-19, "identificationand" should read -- identification and --.

Column 10,
Line 8, "entry" should read -- entity --.

Column 11,
Line 60, "SUP1" should read -- SUP-1 --.

Column 13,
Line 1, "Natl. Acad" should read -- Natl. Acad. --.
Line 6, "Microbiol" should be -- Microbiol --.

Column 17,
Line 62, "electrophoresisin" should be -- electrophoresis in --.

Column 22,
Line 20, "PS11 B" should be -- PS11B --.

UNITED STATES PATENT AND TRADEMARK OFFICE
CERTIFICATE OF CORRECTION

PATENT NO. : 6,204,435 B1
DATED : March 20, 2001
INVENTOR(S) : Feitelson et al.

It is certified that error appears in the above-identified patent and that said Letters Patent is hereby corrected as shown below:

Column 24,
Line 24, "pCR2. 1," should be -- pCR2.1, --.
Line 48, "PS202E1, and KB38." should be -- PS202E1, KB33, and KB38. --.
Line 58, "Lenga" should be -- Length --.

Column 25, Table,
Line 21, (Probe Seq I.D. Number 33): "(PS)17718" should be -- (PS)17718 --.
Line 26, (Probe Seq I.D. Number 37): "ECoRV:" should be -- EcoRV: --.
Line 37, (Probe Seq I.D. Number 47): "SaII:" should be -- SalI --.

Column 28,
Line 11, "confined" should be -- confirmed --.
Line 67, "epsilon" should be -- ipsilon --.

Column 29 and 30, Table 4,
Line 13, (Strain PS80JJ1 (#2)): "3.5" should be -- 35 --.
Line 21, (Strain PS112D3 (#1)): "No" should be -- no --.

Column 29,
Line 47, "KB68B55, PS177C2" should be -- KB68B55-2, PS177C8 --.

Column 31,
Line 55, "EMBO J" should be -- EMBO J. --.

Signed and Sealed this

Twenty-sixth Day of February, 2002

Attest:

JAMES E. ROGAN
*Attesting Officer*     *Director of the United States Patent and Trademark Office*